(12) United States Patent
O'Brien et al.

(10) Patent No.: US 7,939,321 B2
(45) Date of Patent: May 10, 2011

(54) TADG-15: AN EXTRACELLULAR SERINE PROTEASE OVEREXPRESSED IN CARCINOMAS

(75) Inventors: Timothy J. O'Brien, Little Rock, AR (US); Hirotoshi Tanimoto, Kagawa (JP)

(73) Assignee: Board of Trustees of the University of Arkansas, Little Rock, AK (US)

(*) Notice: Subject to any disclaimer, the term of this patent is extended or adjusted under 35 U.S.C. 154(b) by 610 days.

(21) Appl. No.: 11/978,259

(22) Filed: Oct. 29, 2007

(65) Prior Publication Data

US 2009/0274618 A1    Nov. 5, 2009

Related U.S. Application Data

(60) Division of application No. 10/600,187, filed on Jun. 20, 2003, now Pat. No. 7,291,462, which is a division of application No. 09/654,600, filed on Sep. 1, 2000, now Pat. No. 6,649,741, which is a division of application No. 09/421,213, filed on Oct. 20, 1999, now Pat. No. 7,022,821, which is a continuation-in-part of application No. 09/027,337, filed on Feb. 20, 1998, now Pat. No. 5,972,616.

(51) Int. Cl.
C12N 5/00 (2006.01)
C12N 5/02 (2006.01)
C12N 5/06 (2006.01)
C12N 5/07 (2010.01)
C12N 5/071 (2010.01)
C12N 5/078 (2010.01)
C12N 5/0781 (2010.01)
C12N 5/0783 (2010.01)
C12N 5/0784 (2010.01)
C12N 5/08 (2006.01)
C12N 5/10 (2006.01)
G01N 1/00 (2006.01)

(52) U.S. Cl. ........ 435/377; 435/325; 435/363; 435/366; 435/372; 435/372.2; 435/372.3; 436/64; 436/86; 436/174

(58) Field of Classification Search .................. None
See application file for complete search history.

*Primary Examiner* — Alana M. Harris
(74) *Attorney, Agent, or Firm* — Benjamin Aaron Adler

(57) ABSTRACT

The present invention provides DNA encoding a TADG-15 protein as well as a TADG-15 protein. Also provided is a vector capable of expressing the DNA of the present invention adapted for expression in a recombinant cell and regulatory elements necessary for expression of the DNA in the cell. The present invention further provides for methods of inhibiting TADG-15 expression and/or protease activity, methods of detecting TADG-15 mRNA and/or protein and methods of screening for TADG-15 inhibitors. Additionally, the present invention provides for cell-specific targeting via TADG-15 and methods of vaccinating an individual against TADG-15. The methods described are useful in the diagnosis, treatment and prevention of cancer, particularly breast and ovarian cancer.

2 Claims, 20 Drawing Sheets

```
Heps    RIVGGRDTSL GRWPWQVSL. ....RYDG.A HLCGGSLLSG DWVLTAAHCF PE....RNRV
Tadg15  RVVGGTDADE GEWPWQVSL. .....HALGQG HICGASLISP NWLVSAAHCY IDDRGFRYSD
Scce    KIIDGAPCAR GSHPWQVAL. ....LSGNQL H.CGGVLVNE RWVLTAAHC. .........K
Try     KIVGGYNCEE NSVPYQVSL. .....NSGYHF ..CGGSLINE QWVVSAGHC. .........Y
Chymb   RIVNGEDAVP GSWPWQVSL. ....QDKTGF HFCGGSLISE DQVVTAAHC. ........GV
Fac7    RIVGGKVCPK GECPWQVLL. ....LVNG.A QLCGGTLINT IWVVSAAHCF DKIKNWRNLI
Tpa     RIKGGLFADI ASHPWQAAIF AKHRRSPGER FLCGGILISS CWILSAAHCF QERFPPHHL.
                                                        *

Heps    LSRWRVFAGA VAQASPHGLQ LGVQAVVYHG GYLPFRDPNS EENSNDIALV HLSS.PLPLT
Tadg15  PTWETAFLHL HDQSQRSAPG VQERRLKRII SHPFFNDFTF D...YDIALL ELEK.FAEYS
Scce    MNEYTVHLGS DTLG..DR.R AQRIKASKSF RHPGYSTQT. ..HVNDLMLV KLNS.QARLS
Try     KSRIQVRLGE HNIEVLEG.N EQFINAAKII RHPQYDRKT. .LNNDIMLI KLSS.RAVIN
Chymb   RTSDVVVAGE FDQGSDEE.N IQVLKIAKVF KNPKFSILT. ..VNNDITLL KLAT.PARFS
Fac7    ....AVLGE HDLSEHDGDE QSRRVAQVII P....STYVP GTTNHDIALL RLHQ.PVVLT
Tpa     ....TVILGR .TYRVVPGEE EQKFEVEKYI VHKEFDDDTY D...NDIALL QLKSDSSRCA
                                                                  *

Heps    EYIQPVCLPA ...AGQALVD GKICTVTGWG NTQYYGQQ.A GVLQEAAVPI ISNDVCNGAD
Tadg15  SMVRPICLPD ...ASHVFPA GKAIWVTGWG HTQYGGTG.A LILQKGEIRV INQTTCE..N
Scce    SMVKKVRLPS ...RCE..PP GTTCTVSGWG TTTSPDVTFP SDLMCVDVKL ISPQDCTKV.
Try     ARVSTISLPT ...APP..AT GTKCLISGWG NTASSGADYP DELQCLDAPV LSQAKCEAS.
Chymb   QTVSAVCLPS ...ADDDFPA GTLCATTGWG KTKYNANKTP DKLQQAALPL LSNAECKKS.
Fac7    DHVVPLCLPE RTFSERTLAF VRFSLVSGWG QLLDRGATAL ELMVLNVPRL NTQDCLQQSR
Tpa     QESSVVRTVC LPPADLQLPD WTECELSGYG KHEALSPFYS ERLKEAHVRL YPSSRCTSQH
```

Fig. 1A

| | | | | | | | |
|---|---|---|---|---|---|---|---|
| Heps | FYGN..QIKP | KMFCAGYPEG | G......IDA | CQGDSGGPFV | CEDSISRTPR | WRLCGIVSWG | |
| Tadg15 | LLPQ..QITP | RMMCVGFLSG | G......VDS | CQGDSGGPL. | ..SSVEADGR | IFQAGVVSWG | |
| Scce | .YKD..LLEN | SMLCAGIPDS | K......KNA | CNGDSGGPLV | C......R.. | GTLQGLVSWG | |
| Try | .YPG..KITS | NMFCVGFLEG | G......KDS | CQGDSGGPVV | C......M.. | GQLQGVVSWG | |
| Chymb | .WGR..RITD | VMICAG..AS | G......VSS | CMGDSGGPLV | C......QKDGA | WTLVGIVSWG | |
| Fac7 | KVGDSPNITE | YMFCAGYSDG | S......KDS | CKGDSGGP.. | ..HATHYRGT | WYLTGIVSWG | |
| Tpa | LLNRT..VTD | NMLCAGDTRS | GGPQANLHDA | CQGDSGGPLV | CLN....DGR | MTLVGIISWG | |
| | | | * | | | | |
| Heps | T.GCALAQKP | GVYTKVSDFR | EWIFQAIKTH | SEASGXVTQL | -- | -- | (SEQ ID NO: 3) |
| Tadg15 | D.GCAQRNKP | GVYTRLPLFR | DWIKENTGV- | -- | -- | -- | (SEQ ID NO: 14) |
| Scce | TFPCGQPNDP | GVYTQVCKFT | KWINDTMKKH | R-- | -- | -- | (SEQ ID NO: 4) |
| Try | D.GCAQKNKP | GVYTKVYNYV | KWIKNTIAAN | S-- | -- | -- | (SEQ ID NO: 5) |
| Chymb | DSTCS..TSSP | GVYARVTKLI | PWVQKILAAN | -- | -- | -- | (SEQ ID NO: 6) |
| Fac7 | Q.GCATVGHF | GVYTRVSQYI | EWLQKLMRSE | PRPGVLLRAP | FP | -- | (SEQ ID NO: 7) |
| Tpa | .LGCGQKDVP | GVYTKVTNYL | DWIRDNMRP- | -- | -- | -- | (SEQ ID NO: 8) |

Fig. 1B

```
  1 TCAAGAGCGGCCTCGGGGTACCATGGGGAGCGATCGGGCGAGCCCGCAAGGGCGGGAGGGCCCGAAGGACTTCGGCGC
                    M  G  S  D  R  A  R  K  G  G  G  P  K  D  F  G  A    18
 76 GGGACTCAAGTACAACTCCCGGCACGAGAAAGTGAATGGCTTGGAGGAAGGCGTTGAGTTCCTGCCAGTCAACAA
     G  L  K  Y  N  S  R  H  E  K  V  N  G  L  E  E  G  V  E  F  L  P  V  N  N     43
151 CGTCAAGAAGGTGGAAAAGCATGGCCCGGGGCGCTGGGTGGTGCTGGCAGCCGTGCTGATCGGCCTCCTCTTGGT
     V  K  K  V  E  K  H  G  P  G  R  W  V  V  L  A  A  V  L  I  G  L  L  L  V     68
226 CTTGCTGGGGATCGGCTTCCTGGTGTGGCATTTGCAGTACCGGGACGTGCGTGTCCAGAAGGTCTTCAATGGCTA
     L  L  G  I  G  F  L  V  W  H  L  Q  Y  R  D  V  R  V  Q  K  V  F  N  G  Y     93
301 CATGAGGATCACAAATGAGAATTTTGTGGATGCCTACGAGAACTCCAACTCGAGTTTGTAAGCCTGGCCAG
      M  R  I  T  N  E  N  F  V  D  A  Y  E  N  S  N  S  T  E  F  V  S  L  A  S   118
376 CAAGGTGAAGGACGCGCTGAAGCTGCTGTACAGCGGAGTCCCATTCCTGGGCCCCTACCACAAGGAGTCGGCTGT
     K  V  K  D  A  L  K  L  L  Y  S  G  V  P  F  L  G  P  Y  H  K  E  S  A  V    143
451 GACGGCCTTCAGCGAGGGCAGCGTCATCGCCTACTACTGGTCTGAGTTCAGCATCCCGCAGCACCTGGTGGAGGA
     T  A  F  S  E  G  S  V  I  A  Y  Y  W  S  E  F  S  I  P  Q  H  L  V  E  E    168
526 GGCCGAGCGCGTCATGGCCGAGGAGCGCGTAGTCATGCTGCCCCCGCGCGCTCCCTGAAGTCCTTTGTGGT
     A  E  R  V  M  A  E  E  R  V  V  M  L  P  P  R  A  R  S  L  K  S  F  V  V    193
601 CACCTCAGTGGTGGCCTTTCCCCACGACTCCAAAACAGTACAGAGGACCCAGGACAACAGCTGCAGCTTTGGCCT
     T  S  V  V  A  F  P  T  D  S  K  T  V  Q  R  T  Q  D  N  S  C  S  F  G  L    218
676 GCACGGCCCGCGTGGTGGAGCTGATGCGGACGACCCCAGGCCGTCCCTGACAGCCCTACCCCGCTCATGCCCG
      H  A  R  G  V  E  L  M  R  G  T  T  P  G  R  P  D  S  P  Y  P  A  H  A  R   243
```

Fig. 2A

```
 751  CTGCCAGTGGGCCCTGCGCGGGACGCCGACTCAGTGCTGAGCCTTCCGCAGCTTTGACCTTGCGTCCTG
       C  Q  W  A  L  R  G  D  A  D  S  V  L  S  L  T  F  R  S  F  D  L  A  S  C    268
 826  CGACGAGCGCGGCAGCGACCTGGTGACGGTGTACAACACCCTGAGCCCCATGGAGCCCCACGCCCTGGTGCAGTT
       D  E  R  G  S  D  L  V  T  V  Y  N  T  L  S  P  M  E  P  H  A  L  V  Q  L    293
 901  GTGTGGCACCTACCCTCCCTCCTACAACCTGACCTTCCACTCCTGCTCATCACACTGATAAAC
       C  G  T  Y  P  P  S  Y  N  L  T  F  H  S  Q  N  V  L  I  T  L  I  T         318
 976  CAACACTGAGCGGCGGCATCCCGGCTTTGAGGCCACCTTCTTCCAGCTGCCTAGGATGAGCAGCTGTGGAGGCCG
       N  T  E  F  F  H  P  G  F  E  A  T  F  F  Q  L  P  R  M  S  S  C  G  G  R    343
1051  CTTACGTAAAGCCCAGGGACATTCAACAGCCCACTACCACCAGGCCACTACCCAACATTGACTGACACATG
       L  R  K  A  Q  G  T  F  N  S  P  Y  Y  P  G  H  Y  P  P  N  I  D  C  T  W    368
1126  GAACATTGAGGTGCCCAACAACCAGCATGTGAAGGTGAGCTTCAAATTCTTCTACCTGCTGGAGCCCGGCGTGCC
       N  I  E  V  P  N  N  Q  H  V  K  V  S  F  K  F  F  Y  L  L  E  P  G  V  P    393
1201  TGCGGGCACCTGCCCCAAGGACTACGTGGAGATCAATGGGGAGAAATACTGCGGAGAGAGGTCCCAGTTCGTCGT
       A  G  T  C  P  K  D  Y  V  E  I  N  G  E  K  Y  C  G  E  R  S  Q  F  V  V    418
1276  CACCAGCAACAAGATCACAGTTCGCTTCCACTCAGATCAGTCCTACACCGACACCGGCTTCTTAGCTGA
       T  S  N  K  I  T  V  R  F  H  S  D  Q  S  Y  T  D  T  G  F  L  A  E         443
1351  ATACCTCTCCTACGACTCCAGTGACCCATGCCCGGGGCAGTTCACGTGCCGCACGGGGTGTATCCGGAAGGA
       Y  L  S  Y  D  S  D  P  C  P  G  Q  F  T  C  R  T  G  R  C  I  R  K  E      468
1426  GCTGCGCTGTGATGGCTGGGCCGACTGCACCGACCACAGCGATGAGCTCAACTGCAGTTGCCGACGCCGGCCACCA
       L  R  C  D  G  W  A  D  C  T  D  H  S  D  E  L  N  C  S  C  D  A  G  H  Q    493
```

Fig. 2B

```
1501 GTTCACGTGCAAGAACAAGTTCTGCAAGCCCCTCTTCTGGGTCTGCGACAGTGTGAACGACTGCGGAGACAACAG    518
       F  T  C  K  N  K  F  C  K  P  L  F  W  V  C  D  S  V  N  D  C  G  D  N  S
1576 CGACGAGCAGGGGTGCAGTTGTCCGGCCCAGACCTTCAGGTGTTCCAATGGGAAGTGCCTCTCGAAAAGCCAGCA    543
       D  E  Q  G  C  S  C  P  A  Q  T  F  R  C  S  N  G  K  C  L  S  K  S  Q  Q
1651 GTGCAATGGGAAGGACGACTGTGGGGACGGGTCCGACGAGGCCTCTGCCCCAAGTGAACGTCGTCACTTGTAC    568
       C  N  G  K  D  D  C  G  D  G  S  D  E  A  S  C  P  K  V  N  V  V  T  C  T
1726 CAAACACACCTACCGCTGCCTGAATGGGCTCTGCTTGAGCAAGGGCAACCCTGAGTGTGACGGGAAGGAGGACTG    593
       K  H  T  Y  R  C  L  N  G  L  C  L  S  K  G  N  P  E  C  D  G  K  E  D  C
1801 TAGCGACGGGCTCAGATGCGAGAAGGACTGCGACTGTGGGCCTCCGGTCATTCACGAGACAGGCTCGTGTGTGGGGG    618
       S  D  G  L  R  C  E  K  D  C  D  C  G  L  R  S  F  T  R  Q  A  R  V  G  G
1876 CACGGATGCGGAGGGCGAGTGGCCCTGGCAGGTAAGCCTGGCCATGCTCTGGCCCAGGCCCACATCTGCGGTGC    643
       H  G  C  G  G  E  W  P  W  Q  V  S  L  H  A  L  G  Q  G  H  I  C  G  A
1951 TTCCCTCATCTCTCCCAACTGGCTGGTCTCTGCCGCACACTGCTACATCGATGACAGAGATTCAGGTACTCAGA    668
       S  L  I  S  P  N  W  L  V  S  A  A  H  C  Y  I  D  D  R  G  F  R  Y  S  D
2026 CCCCACGACGTGGACAGCCTTGCACGACCAGCGCCAGCCCCTGGGGTGCAGGAGCGCAG    693
       P  P  T  Q  W  T  A  F  L  G  L  H  D  Q  S  Q  R  S  A  P  G  V  Q  E  R  R
2101 GCTCAAGCGGCATCATCTCCACCCCTTCTTCAATGACTTCACCTTCGACTATGACATCGCGCTGCTGGAGCTGGA    718
       L  K  R  I  I  S  H  P  F  F  N  D  F  T  F  D  Y  D  I  A  L  L  E  L  E
2176 GAAACCGGCAGAGTACAGCTCCCATGGTGCCGACGCCTCCCATGTCTTCCCTGCCGGCAA    743
       K  P  A  E  Y  S  S  M  V  R  P  I  C  L  P  D  A  S  H  V  F  P  A  G  K
```

Fig. 2C

```
2251 GGCCATCTGGGTCACGGGCTGGGGACACACCCAGTATGGAGGCACTGGCGCGCTGATCCTGCAAAAGGGTGAGAT
      A  I  W  V  T  G  W  G  H  T  Q  Y  G  G  T  G  A  L  I  L  Q  K  G  E  I    768
2326 CCGCGTCATCAACCAGACCACTTGCGAGAACCTCCTGCCGCAGATCACGCCGCATGATGTGCGTGGGCTT
      R  V  I  N  Q  T  T  C  E  N  L  L  P  Q  Q  I  T  P  R  M  M  C  V  G  F    793
2401 CCTCAGCGCGGCGTGGACTCCTGCCAGGGTGATTCCGGGGACCCCTGTCCAGCGTGGAGGCGTGGGGCGGAT
      L  S  G  G  V  D  S  C  Q  G  D  S  G  G  P  L  S  S  V  E  A  D  G  R  I    818
2476 CTTCCAGGCCGGTGTGTGTGAGCTGGGAGAGAGAAAGCCAGGCGTGTACACAAGGCTCCC
      F  Q  A  F  C  C  S  W  G  D  G  C  A  Q  R  N  K  P  G  V  Y  T  R  L  P    843
2551 TCTGTTTCGGGACTGGATCAAAGAGAACACTGGGGTATAGGGCCCACCCAAATGTGTACACCTGCGGGG
      L  F  R  D  W  I  K  E  N  T  G  V                                           855
                                                         (SEQ ID NO: 2)
2626 CCACCCATCGTCCACCCCAGTGTGCACGCTGCCGCTGAGACTGACTGCACCAGCGCCCCCAGAA
2701 CATACACTGTGAACTGAATCTCCAGGCTCTCCAAATCTGCTTACTGACCCAACTGGTGTTCTCAGCCTCCAAAGTGG
2776 AGCTGGAGGTAGAAGGGAGGACACTGGGCCAACTGGTGTTTGTATATCGCCTCCCCTGTCTGTAAGGAGCAGCGGGAA
2851 CCCCCGCCAGCCCAAGCTCGGAGCCCTCAGTGAAGGCCTGGCCCGATCTGGGCCCTTGGGCCACGCTCT
2926 CGGAGCTTCGGAGGCCCAGGCTCGGAGGACCCCTGAAATGGGTAAAACAATTTATTTCTTTTTAAAAAAAAAAAAAAA
3001 TGAGGAAGCCCAGGCTCGGAGGACCCCTGAGACTGAAATTGTTTTACCAGCTCCCAGGG
3076 TGGACTTCAGTGTGTGTATTTGTGTAAATGGGTAAACAATTTATTTCTTTTTAAAAAAAAAAAAAAA
                                                         (SEQ ID NO: 1)

: KOZAK'S CONSENSUS SEQUENCE
: TRANSMEMBRANE DOMAIN
: CONSERVED AMINO ACIDS OF CATALYTIC TRIAD H,D,S
```

Fig. 2D

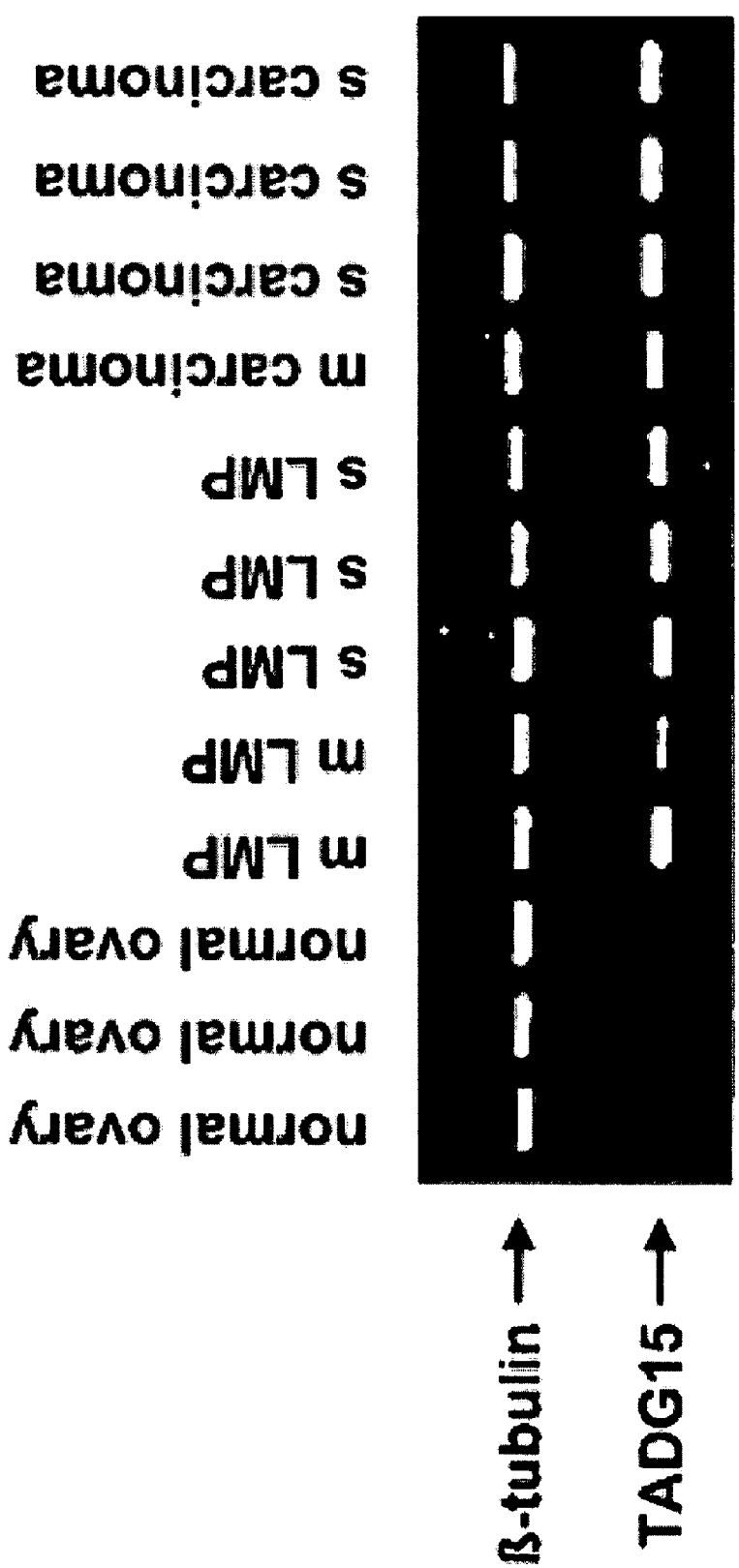

| | | | | | | |
|---|---|---|---|---|---|---|
| hTADG15 | MGSDRARKGG | GGPRDFGAGL | KYNSREEKVN | GLEEGVEELP | VNNVKVEKB | 50 |
| mEpithin | ---N-G--A- | --SQ------ | ---D--L-NM- | -F-------- | A--A----R | |
| hTADG15 | GPGRWVLAA | VLIGLLVLL | GIGELVWHLQ | YRDVRVQKVF | NGYMRITNEN | 100 |
| mEpithin | --R------V- | --FSF--LS- | MA-L----FH | --N------- | --HL-----I | |
| hTADG15 | FVDAYENSNS | TEFVSLASKV | KDALKLLYSG | VPFLGPYHKE | SAVTAFSEGS | 150 |
| mEpithin | -L------T- | ------I--- | -E------NE | --V------K | ---------- | |
| hTADG15 | VIAYYWSEFS | IPQHLVEEAE | RVMAEERVVM | LPPRARSLKS | FVVTSVVAFP | 200 |
| mEpithin | ---------- | --P-A---VD | -A--V----T | -------A-- | ---L------ | |
| hTADG15 | TDSKTVQRTQ | DNSCSEGLHA | RGVELMRFTI | PGFPDSPYPA | HARCQWALRG | 250 |
| mEpithin | I-PRML---- | ------A--- | H--AAVT--- | ----N----- | -------V-- | |
| hTADG15 | DADSVLSLTF | RSFDLASCDE | RGSDLVTVYN | TLSPMEPHAL | VQLCGTYPPS | 300 |
| mEpithin | ---------- | ---V-P---- | H-------D | S-------V | --R----FS- | |
| hTADG15 | YNLIFHSSQN | VLLITLITNT | ERRHPGFEAT | FFQLPRMSSC | GGRLRKAQGT | 350 |
| mEpithin | ------L--- | --F-V----- | ---G---L-- | -------K-- | --V-SDT--- | |
| hTADG15 | FNSPYYPGHY | PPNIDCTWNI | EVPNNQHVKV | SFKFFYLIEP | GVPAGTCPRD | 400 |
| mEpithin | -S-------- | ------N--- | ----K----- | R---L---VD- | N--V-S-T-- | |
| hTADG15 | YVEINGEKYC | GERSQFVVTS | NSNKITVRFH | SDQSYIDTGF | LAEYLSYDSS | 450 |
| mEpithin | -------GS | ----S---- | ---S---H-- | --H------- | ---------N | |

Fig. 11A

```
hTADG15    DPCPGQFTCR  TGRCIRKELR  CDGWADCTDH  SDELNCSCDA  GHQFTCKNKF  500
mEpithin   ---------- ----M-M-K-  ----------  ----P-Y---  -RY-R-N---  -------Q-- hTADG15    CKPLFWVCDS  VNDCGDNSDE  QGCSCPAQTF  RCSNGKCLSK  SQQCNGKDDC  550
mEpithin   ---------- ----------  -------G--  --E-------  -GS------PQ  --K-----N- hTADG15    GDGSDEASCP  KVNVTCTKH   TYRCLNGLCL  SKGNPECDGK  EDCSDGSDEK  600
mEpithin   ---------- -------D-S  ----S---Y-  ------Q---  ----------  -----T---- hTADG15    DCDCGLRSFT  RQARVVGGTD  ADEGEWPWQV  SLHALGQGHI  CGASLISPNW  650
mEpithin   ----N----- -------K--  -------N--  ----------  ----------  ------D--- hTADG15    LVSAAHCYID  DRGFRYSDPT  QWTAFLGLHD  QSQRSAPGVQ  ERRLKRIISH  700
mEpithin   ------FQ-- -RN-K--Y--  -------M--  ----K----S  ----------  --LK-----T- hTADG15    PFFNDFTFDY  DIALLELEKP  AEYSSMVRPI  CLPDASHVFP  AGKAIWVTGW  750
mEpithin   ----S----- ---------S  ----V----TV  -----T----  ----------  ---------- hTADG15    GHTQYGGTGA  LILQKGEIRV  INQTTCENLL  PQQITPRMWC  VGFLSGGVDS  800
mEpithin   ----KE---- ----------  -----D-M--  ----------  ----------  ---------- hTADG15    CQGDSGGPLS  SVEADGRIFQ  AGVVSWGDGC  AQRNKPGVYT  RLPLFRDWIK  850
mEpithin   ---------- ----A---M-  -------E--  ----------  ----------  ---CSSGLDQ hTADG15    ENTGV*                                                     900
mEpithin   RAHWGIAAWT  DSRPQTPTGM  PDMHTWIQER  NTDDIYAVAS  PPQHNPDCEL hTADG15    SEQ ID NO: 2                                               902
mEpithin   HP SEQ ID NO: 10
```

```
2771 AGTGGAGCTGGGA.GGTAGAAGGGGAGG..ACACTGGTGTTCTACTGACCCAACTGGGGGCAAAGGTTTGAAGACACAGCCTCCCCCGCCAGCCCCAAGC 2868
        ||||||||||||| ||||||||||||||  ||||||||||||||||||||||||||||||| ||||||||||||| ||||||
2568 AGTGGAGCTGGGAAGGGGAGTAGAAGGGGAGGAACACTGGTGGTTCTACTGACCCAACTGGGG..CAAGGTTTGAAG.CACAG....CTCCGGCAGCCC...AAG 2658

2869 TGGGCCGAGGCGCGTTTGTGTATATCTGCCTCCCCCTGTCTGTAAGGAGCAGCGGGAACGGAGCTTCGGAGCCTCCTCAGTGAAGGTGGTGGGCTGCCGG 2968
     |||||||||||||||||||| ||||| || ||  ||| |||||||||||  || ||||||||||||||||||||||||||||||
2659 TGGGCGAGGACGCGTTTGTGCATA..CTGCC..CTGCTCTATACACGGAAGACCTGGA..........TCTCTAGTGA......GTGTGACTGCCGG 2735

2969 ATCTGGGCTGTGTGGGGCCCTTGGGCCACGCTCTTGAGGAAGCCCAGGCTCGGAGGACCCTGAAAACAGACGGGTCTGAGACTGAAATTGTTTTACCAGCT 3068
     ||||||   ||||| |||||| ||||||||||||||| |||||||||||||||||||||||||||||||||||||||||||| |||||| ||||||||||
2736 ATCTGG...CTGTGGTCCTTGGCCACGCTTCTTGAGGAAGCCCAGGCTCGGAGGACCCTGAAAACAGACGGGTCTGAGACTGAAAATGGTTTACCAGCT 2832

3069 CCCAGGGGTGGACTTCAGTGTGTGTATTTGTGTAAATGGGTAAAACAATTTATTTCTTTTTAAAAAAAAAAAAA 3147 (SEQ ID NO: 1)
     ||||||  ||||||||||||||||||| ||||||||||||||||||||||||| |||||||| ||||||||||||
2833 CCCAGG..TGACTTCAGTGTGTGTGTA.TTGTGTAAATGAGTAAAACATTTTATTTCTTTTTAAAAAAAAAA......... 2900 (SEQ ID NO: 9)
```

Fig. 12E

SEQUENCE LISTING

<160> NUMBER OF SEQ ID NOS: 98

<210> SEQ ID NO 1
<211> LENGTH: 3147
<212> TYPE: DNA
<213> ORGANISM: Homo sapiens
<220> FEATURE:
<223> OTHER INFORMATION: TADG-15

<400> SEQUENCE: 1

| | | | | | |
|---|---|---|---|---|---|
| tcaagagcgg | cctcggggta | ccatggggag | cgatcgggcc | cgcaagggcg | gagggggccc | 60 |
| gaaggacttc | ggcgcgggac | tcaagtacaa | ctcccggcac | gagaaagtga | atggcttgga | 120 |
| ggaaggcgtg | gagttcctgc | cagtcaacaa | cgtcaagaag | gtggaaaagc | atggcccggg | 180 |
| gcgctgggtg | gtgctggcag | ccgtgctgat | cggcctcctc | ttggtcttgc | tggggatcgg | 240 |
| cttcctggtg | tggcatttgc | agtaccggga | cgtgcgtgtc | cagaaggtct | tcaatggcta | 300 |
| catgaggatc | acaaatgaga | attttgtgga | tgcctacgag | aactccaact | ccactgagtt | 360 |
| tgtaagcctg | gccagcaagg | tgaaggacgc | gctgaagctg | ctgtacagcg | gagtcccatt | 420 |
| cctgggcccc | taccacaagg | agtcggctgt | gacggccttc | agcgagggca | gcgtcatcgc | 480 |
| ctactactgg | tctgagttca | gcatcccgca | gcacctggtg | gaggaggccg | agcgcgtcat | 540 |
| ggccgaggag | cgcgtagtca | tgctgccccc | gcgggcgcgc | tccctgaagt | cctttgtggt | 600 |
| cacctcagtg | gtggctttcc | ccacggactc | caaaacagta | cagaggaccc | aggacaacag | 660 |
| ctgcagcttt | ggcctgcacg | cccgcggtgt | ggagctgatg | cgcttcacca | cgcccggctt | 720 |
| ccctgacagc | ccctacccg | ctcatgcccg | ctgccagtgg | gccctgcggg | gggacgccga | 780 |
| ctcagtgctg | agcctcacct | tccgcagctt | tgaccttgcg | cctgcgacg | agcgcggcag | 840 |
| cgacctggtg | acggtgtaca | acacccctgag | ccccatggag | ccccacgccc | tggtgcagtt | 900 |
| gtgtggcacc | taccctcccct | cctacaacct | gaccttccac | tcctcccaga | acgtcctgct | 960 |
| catcacactg | ataaccaaca | ctgagcggcg | gcatcccggc | tttgaggcca | ccttcttcca | 1020 |
| gctgccaagg | atgagcagct | gtggaggccg | cttacgtaaa | gcccagggga | cattcaacag | 1080 |
| cccctactac | ccaggccact | acccacccaa | cattgactgc | acatggaaca | ttgaggtgcc | 1140 |
| caacaaccag | catgtgaagg | tgagcttcaa | attcttctac | ctgctggagc | ccggcgtgcc | 1200 |
| tgcgggcacc | tgccccaagg | actacgtgga | gatcaatggg | gagaaatact | gcggagagag | 1260 |
| gtcccagttc | gtcgtcacca | gcaacagcaa | caagatcaca | gttcgcttcc | actcagatca | 1320 |
| gtcctacacc | gacaccggct | tcttagctga | atacctctcc | tacgactcca | gtgacccatg | 1380 |
| cccgggggcag | ttcacgtgcc | gcacggggcg | gtgtatccgg | aaggagctgc | gctgtgatgg | 1440 |
| ctgggccgac | tgcaccgacc | acagcgatga | gctcaactgc | agttgcgacg | ccggccacca | 1500 |
| gttcacgtgc | aagaacaagt | tctgcaagcc | cctcttctgg | gtctgcgaca | gtgtgaacga | 1560 |
| ctgcggagac | aacagcgacg | agcaggggtg | cagttgtccg | gcccagacct | tcaggtgttc | 1620 |
| caatgggaag | tgcctctcga | aaagccagca | gtgcaatggg | aaggacgact | gtggggacgg | 1680 |
| gtccgacgag | gcctcctgcc | ccaaggtgaa | cgtcgtcact | tgtaccaaac | acacctaccg | 1740 |
| ctgcctcaat | gggctctgct | tgagcaaggg | caacccgag | tgtgacggga | aggaggactg | 1800 |
| tagcgacggc | tcagatgaga | aggactgcga | ctgtgggctg | cggtcattca | cgagacaggc | 1860 |
| tcgtgttgtt | gggggcacgg | atgcggatga | gggcgagtgg | ccctggcagg | taagcctgca | 1920 |
| tgctctgggc | cagggccaca | tctgcggtgc | ttccctcatc | tctcccaact | ggctggtctc | 1980 |

```
tgccgcacac tgctacatcg atgacagagg attcaggtac tcagacccca cgcagtggac    2040
ggccttcctg ggcttgcacg accagagcca gcgcagcgcc cctggggtgc aggagcgcag    2100
gctcaagcgc atcatctccc acccccttctt caatgacttc accttcgact atgacatcgc   2160
gctgctggag ctggagaaac cggcagagta cagctccatg gtgcggccca tctgcctgcc   2220
ggacgcctcc catgtcttcc ctgccggcaa ggccatctgg gtcacgggct ggggacacac   2280
ccagtatgga ggcactggcg cgctgatcct gcaaaagggt gagatccgcg tcatcaacca   2340
gaccacctgc gagaacctcc tgccgcagca gatcacgccg cgcatgatgt gcgtgggctt   2400
cctcagcggc ggcgtggact cctgccaggg tgattccggg ggacccctgt ccagcgtgga   2460
ggcggatggg cggatcttcc aggccggtgt ggtgagctgg ggagacggct gcgctcagag   2520
gaacaagcca ggcgtgtaca caaggctccc tctgtttcgg gactggatca agagaaacac   2580
tggggtatag gggccggggc cacccaaatg tgtacacctg cggggccacc catcgtccac   2640
cccagtgtgc acgcctgcag gctggagact ggaccgctga ctgcaccagc gcccccagaa   2700
catacactgt gaactcaatc tccagggctc caaatctgcc tagaaaacct ctcgcttcct   2760
cagcctccaa agtggagctg ggaggtagaa ggggaggaca ctggtggttc tactgaccca   2820
actgggggca aaggtttgaa gacacagcct cccccgccag ccccaagctg ggccgaggcg   2880
cgtttgtgta tatctgcctc ccctgtctgt aaggagcagc gggaacggag cttcggagcc   2940
tcctcagtga aggtggtggg gctgccggat ctgggctgtg gggcccttgg gccacgctct   3000
tgaggaagcc caggctcgga ggaccctgga aaacagacgg gtctgagact gaaattgttt   3060
taccagctcc cagggtggac ttcagtgtgt gtatttgtgt aaatgggtaa aacaatttat   3120 ttcttttttaa aaaaaaaaa aaaaaaa                                        3147
```

```
<210> SEQ ID NO 2
<211> LENGTH: 855
<212> TYPE: PRT
<213> ORGANISM: Homo sapiens
<220> FEATURE:
<223> OTHER INFORMATION: TADG-15

<400> SEQUENCE: 2

Met Gly Ser Asp Arg Ala Arg Lys Gly Gly Gly Pro Lys Asp
                5                  10                  15

Phe Gly Ala Gly Leu Lys Tyr Asn Ser Arg His Glu Lys Val Asn
            20                  25                  30

Gly Leu Glu Glu Gly Val Glu Phe Leu Pro Val Asn Asn Val Lys
        35                  40                  45

Lys Val Glu Lys His Gly Pro Gly Arg Trp Val Val Leu Ala Ala
    50                  55                  60

Val Leu Ile Gly Leu Leu Leu Val Leu Leu Gly Ile Gly Phe Leu
65                  70                  75

Val Trp His Leu Gln Tyr Arg Asp Val Arg Val Gln Lys Val Phe
            80                  85                  90

Asn Gly Tyr Met Arg Ile Thr Asn Glu Asn Phe Val Asp Ala Tyr
        95                  100                 105

Glu Asn Ser Asn Ser Thr Glu Phe Val Ser Leu Ala Ser Lys Val
            110                 115                 120

Lys Asp Ala Leu Lys Leu Leu Tyr Ser Gly Val Pro Phe Leu Gly
        125                 130                 135

Pro Tyr His Lys Glu Ser Ala Val Thr Ala Phe Ser Glu Gly Ser
            140                 145                 150
```

```
Val Ile Ala Tyr Tyr Trp Ser Glu Phe Ser Ile Pro Gln His Leu
            155                 160                 165

Val Glu Glu Ala Glu Arg Val Met Ala Glu Arg Val Val Met
            170                 175                 180

Leu Pro Pro Arg Ala Arg Ser Leu Lys Ser Phe Val Val Thr Ser
            185                 190                 195

Val Val Ala Phe Pro Thr Asp Ser Lys Thr Val Gln Arg Thr Gln
            200                 205                 210

Asp Asn Ser Cys Ser Phe Gly Leu His Ala Arg Gly Val Glu Leu
            215                 220                 225

Met Arg Phe Thr Thr Pro Gly Phe Pro Asp Ser Pro Tyr Pro Ala
            230                 235                 240

His Ala Arg Cys Gln Trp Ala Leu Arg Gly Asp Ala Asp Ser Val
            245                 250                 255

Leu Ser Leu Thr Phe Arg Ser Phe Asp Leu Ala Ser Cys Asp Glu
            260                 265                 270

Arg Gly Ser Asp Leu Val Thr Val Tyr Asn Thr Leu Ser Pro Met
            275                 280                 285

Glu Pro His Ala Leu Val Gln Leu Cys Gly Thr Tyr Pro Pro Ser
            290                 295                 300

Tyr Asn Leu Thr Phe His Ser Ser Gln Asn Val Leu Leu Ile Thr
            305                 310                 315

Leu Ile Thr Asn Thr Glu Arg Arg His Pro Gly Phe Glu Ala Thr
            320                 325                 330

Phe Phe Gln Leu Pro Arg Met Ser Ser Cys Gly Gly Arg Leu Arg
            335                 340                 345

Lys Ala Gln Gly Thr Phe Asn Ser Pro Tyr Tyr Pro Gly His Tyr
            350                 355                 360

Pro Pro Asn Ile Asp Cys Thr Trp Asn Ile Glu Val Pro Asn Asn
            365                 370                 375

Gln His Val Lys Val Ser Phe Lys Phe Phe Tyr Leu Leu Glu Pro
            380                 385                 390

Gly Val Pro Ala Gly Thr Cys Pro Lys Asp Tyr Val Glu Ile Asn
            395                 400                 405

Gly Glu Lys Tyr Cys Gly Glu Arg Ser Gln Phe Val Val Thr Ser
            410                 415                 420

Asn Ser Asn Lys Ile Thr Val Arg Phe His Ser Asp Gln Ser Tyr
            425                 430                 435

Thr Asp Thr Gly Phe Leu Ala Glu Tyr Leu Ser Tyr Asp Ser Ser
            440                 445                 450

Asp Pro Cys Pro Gly Gln Phe Thr Cys Arg Thr Gly Arg Cys Ile
            455                 460                 465

Arg Lys Glu Leu Arg Cys Asp Gly Trp Ala Asp Cys Thr Asp His
            470                 475                 480

Ser Asp Glu Leu Asn Cys Ser Cys Asp Ala Gly His Gln Phe Thr
            485                 490                 495

Cys Lys Asn Lys Phe Cys Lys Pro Leu Phe Trp Val Cys Asp Ser
            500                 505                 510

Val Asn Asp Cys Gly Asp Asn Ser Asp Glu Gln Gly Cys Ser Cys
            515                 520                 525

Pro Ala Gln Thr Phe Arg Cys Ser Asn Gly Lys Cys Leu Ser Lys
            530                 535                 540

Ser Gln Gln Cys Asn Gly Lys Asp Asp Cys Gly Asp Gly Ser Asp
            545                 550                 555
```

```
Glu Ala Ser Cys Pro Lys Val Asn Val Val Thr Cys Thr Lys His
                560                 565                 570

Thr Tyr Arg Cys Leu Asn Gly Leu Cys Leu Ser Lys Gly Asn Pro
                575                 580                 585

Glu Cys Asp Gly Lys Glu Asp Cys Ser Asp Gly Ser Asp Glu Lys
                590                 595                 600

Asp Cys Asp Cys Gly Leu Arg Ser Phe Thr Arg Gln Ala Arg Val
                605                 610                 615

Val Gly Gly Thr Asp Ala Asp Glu Gly Glu Trp Pro Trp Gln Val
                620                 625                 630

Ser Leu His Ala Leu Gly Gln Gly His Ile Cys Gly Ala Ser Leu
                635                 640                 645

Ile Ser Pro Asn Trp Leu Val Ser Ala Ala His Cys Tyr Ile Asp
                650                 655                 660

Asp Arg Gly Phe Arg Tyr Ser Asp Pro Thr Gln Trp Thr Ala Phe
                665                 670                 675

Leu Gly Leu His Asp Gln Ser Gln Arg Ser Ala Pro Gly Val Gln
                680                 685                 690

Glu Arg Arg Leu Lys Arg Ile Ile Ser His Pro Phe Phe Asn Asp
                695                 700                 705

Phe Thr Phe Asp Tyr Asp Ile Ala Leu Leu Glu Leu Glu Lys Pro
                710                 715                 720

Ala Glu Tyr Ser Ser Met Val Arg Pro Ile Cys Leu Pro Asp Ala
                725                 730                 735

Ser His Val Phe Pro Ala Gly Lys Ala Ile Trp Val Thr Gly Trp
                740                 745                 750

Gly His Thr Gln Tyr Gly Gly Thr Gly Ala Leu Ile Leu Gln Lys
                755                 760                 765

Gly Glu Ile Arg Val Ile Asn Gln Thr Thr Cys Glu Asn Leu Leu
                770                 775                 780

Pro Gln Gln Ile Thr Pro Arg Met Met Cys Val Gly Phe Leu Ser
                785                 790                 795

Gly Gly Val Asp Ser Cys Gln Gly Asp Ser Gly Gly Pro Leu Ser
                800                 805                 810

Ser Val Glu Ala Asp Gly Arg Ile Phe Gln Ala Gly Val Val Ser
                815                 820                 825

Trp Gly Asp Gly Cys Ala Gln Arg Asn Lys Pro Gly Val Tyr Thr
                830                 835                 840

Arg Leu Pro Leu Phe Arg Asp Trp Ile Lys Glu Asn Thr Gly Val
                845                 850                 855

<210> SEQ ID NO 3
<211> LENGTH: 256
<212> TYPE: PRT
<213> ORGANISM: Homo sapiens
<220> FEATURE:
<223> OTHER INFORMATION: Hepsin

<400> SEQUENCE: 3

Arg Ile Val Gly Gly Arg Asp Thr Ser Leu Gly Arg Trp Pro Trp
                5                   10                  15

Gln Val Ser Leu Arg Tyr Asp Gly Ala His Leu Cys Gly Gly Ser
                20                  25                  30

Leu Leu Ser Gly Asp Trp Val Leu Thr Ala Ala His Cys Phe Pro
                35                  40                  45
```

```
Glu Arg Asn Arg Val Leu Ser Arg Trp Arg Val Phe Ala Gly Ala
                 50                  55                  60

Val Ala Gln Ala Ser Pro His Gly Leu Gln Leu Gly Val Gln Ala
             65                  70                  75

Val Val Tyr His Gly Gly Tyr Leu Pro Phe Arg Asp Pro Asn Ser
             80                  85                  90

Glu Glu Asn Ser Asn Asp Ile Ala Leu Val His Leu Ser Ser Pro
             95                 100                 105

Leu Pro Leu Thr Glu Tyr Ile Gln Pro Val Cys Leu Pro Ala Ala
            110                 115                 120

Gly Gln Ala Leu Val Asp Gly Lys Ile Cys Thr Val Thr Gly Trp
            125                 130                 135

Gly Asn Thr Gln Tyr Tyr Gly Gln Gln Ala Gly Val Leu Gln Glu
            140                 145                 150

Ala Arg Val Pro Ile Ile Ser Asn Asp Val Cys Asn Gly Ala Asp
            155                 160                 165

Phe Tyr Gly Asn Gln Ile Lys Pro Lys Met Phe Cys Ala Gly Tyr
            170                 175                 180

Pro Glu Gly Gly Ile Asp Ala Cys Gln Gly Asp Ser Gly Gly Pro
            185                 190                 195

Phe Val Cys Glu Asp Ser Ile Ser Arg Thr Pro Arg Trp Arg Leu
            200                 205                 210

Cys Gly Ile Val Ser Trp Gly Thr Gly Cys Ala Leu Ala Gln Lys
            215                 220                 225

Pro Gly Val Tyr Thr Lys Val Ser Asp Phe Arg Glu Trp Ile Phe
            230                 235                 240

Gln Ala Ile Lys Thr His Ser Glu Ala Ser Gly Met Val Thr Gln
            245                 250                 255

Leu

<210> SEQ ID NO 4
<211> LENGTH: 225
<212> TYPE: PRT
<213> ORGANISM: Homo sapiens
<220> FEATURE:
<223> OTHER INFORMATION: SCCE

<400> SEQUENCE: 4

Lys Ile Ile Asp Gly Ala Pro Cys Ala Arg Gly Ser His Pro Trp
                  5                  10                  15

Gln Val Ala Leu Leu Ser Gly Asn Gln Leu His Cys Gly Gly Val
             20                  25                  30

Leu Val Asn Glu Arg Trp Val Leu Thr Ala Ala His Cys Lys Met
             35                  40                  45

Asn Glu Tyr Thr Val His Leu Gly Ser Asp Thr Leu Gly Asp Arg
             50                  55                  60

Arg Ala Gln Arg Ile Lys Ala Ser Lys Ser Phe Arg His Pro Gly
             65                  70                  75

Tyr Ser Thr Gln Thr His Val Asn Asp Leu Met Leu Val Lys Leu
             80                  85                  90

Asn Ser Gln Ala Arg Leu Ser Ser Met Val Lys Lys Val Arg Leu
             95                 100                 105

Pro Ser Arg Cys Glu Pro Pro Gly Thr Thr Cys Thr Val Ser Gly
            110                 115                 120

Trp Gly Thr Thr Thr Ser Pro Asp Val Thr Phe Pro Ser Asp Leu
            125                 130                 135
```

```
Met Cys Val Asp Val Lys Leu Ile Ser Pro Gln Asp Cys Thr Lys
                140                 145                 150

Val Tyr Lys Asp Leu Leu Glu Asn Ser Met Leu Cys Ala Gly Ile
                155                 160                 165

Pro Asp Ser Lys Lys Asn Ala Cys Asn Gly Asp Ser Gly Gly Pro
                170                 175                 180

Leu Val Cys Arg Gly Thr Leu Gln Gly Leu Val Ser Trp Gly Thr
                185                 190                 195

Phe Pro Cys Gly Gln Pro Asn Asp Pro Gly Val Tyr Thr Gln Val
                200                 205                 210

Cys Lys Phe Thr Lys Trp Ile Asn Asp Thr Met Lys Lys His Arg
                215                 220                 225

<210> SEQ ID NO 5
<211> LENGTH: 225
<212> TYPE: PRT
<213> ORGANISM: Homo sapiens
<220> FEATURE:
<223> OTHER INFORMATION: Trypsin

<400> SEQUENCE: 5

Lys Ile Val Gly Gly Tyr Asn Cys Glu Glu Asn Ser Val Pro Tyr
                5                   10                  15

Gln Val Ser Leu Asn Ser Gly Tyr His Phe Cys Gly Gly Ser Leu
                20                  25                  30

Ile Asn Glu Gln Trp Val Val Ser Ala Gly His Cys Tyr Lys Ser
                35                  40                  45

Arg Ile Gln Val Arg Leu Gly Glu His Asn Ile Glu Val Leu Glu
                50                  55                  60

Gly Asn Glu Gln Phe Ile Asn Ala Ala Lys Ile Ile Arg His Pro
                65                  70                  75

Gln Tyr Asp Arg Lys Thr Leu Asn Asn Asp Ile Met Leu Ile Lys
                80                  85                  90

Leu Ser Ser Arg Ala Val Ile Asn Ala Arg Val Ser Thr Ile Ser
                95                  100                 105

Leu Pro Thr Ala Pro Pro Ala Thr Gly Thr Lys Cys Leu Ile Ser
                110                 115                 120

Gly Trp Gly Asn Thr Ala Ser Ser Gly Ala Asp Tyr Pro Asp Glu
                125                 130                 135

Leu Gln Cys Leu Asp Ala Pro Val Leu Ser Gln Ala Lys Cys Glu
                140                 145                 150

Ala Ser Tyr Pro Gly Lys Ile Thr Ser Asn Met Phe Cys Val Gly
                155                 160                 165

Phe Leu Glu Gly Gly Lys Asp Ser Cys Gln Gly Asp Ser Gly Gly
                170                 175                 180

Pro Val Val Cys Asn Gly Gln Leu Gln Gly Val Val Ser Trp Gly
                185                 190                 195

Asp Gly Cys Ala Gln Lys Asn Lys Pro Gly Val Tyr Thr Lys Val
                200                 205                 210

Tyr Asn Tyr Val Lys Trp Ile Lys Asn Thr Ile Ala Ala Asn Ser
                215                 220                 225

<210> SEQ ID NO 6
<211> LENGTH: 231
<212> TYPE: PRT
<213> ORGANISM: Homo sapiens
<220> FEATURE:
```

<223> OTHER INFORMATION: Chymotrypsin

<400> SEQUENCE: 6

```
Arg Ile Val Asn Gly Glu Asp Ala Val Pro Gly Ser Trp Pro Trp
                 5                  10                  15
Gln Val Ser Leu Gln Asp Lys Thr Gly Phe His Phe Cys Gly Gly
             20                  25                  30
Ser Leu Ile Ser Glu Asp Trp Val Val Thr Ala Ala His Cys Gly
             35                  40                  45
Val Arg Thr Ser Asp Val Val Val Ala Gly Glu Phe Asp Gln Gly
             50                  55                  60
Ser Asp Glu Glu Asn Ile Gln Val Leu Lys Ile Ala Lys Val Phe
             65                  70                  75
Lys Asn Pro Lys Phe Ser Ile Leu Thr Val Asn Asn Asp Ile Thr
             80                  85                  90
Leu Leu Lys Leu Ala Thr Pro Ala Arg Phe Ser Gln Thr Val Ser
             95                 100                 105
Ala Val Cys Leu Pro Ser Ala Asp Asp Phe Pro Ala Gly Thr
            110                 115                 120
Leu Cys Ala Thr Thr Gly Trp Gly Lys Thr Lys Tyr Asn Ala Asn
            125                 130                 135
Lys Thr Pro Asp Lys Leu Gln Gln Ala Ala Leu Pro Leu Leu Ser
            140                 145                 150
Asn Ala Glu Cys Lys Lys Ser Trp Gly Arg Arg Ile Thr Asp Val
            155                 160                 165
Met Ile Cys Ala Gly Ala Ser Gly Val Ser Ser Cys Met Gly Asp
            170                 175                 180
Ser Gly Gly Pro Leu Val Cys Gln Lys Asp Gly Ala Trp Thr Leu
            185                 190                 195
Val Gly Ile Val Ser Trp Gly Ser Asp Thr Cys Ser Thr Ser Ser
            200                 205                 210
Pro Gly Val Tyr Ala Arg Val Thr Lys Leu Ile Pro Trp Val Gln
            215                 220                 225
Lys Ile Leu Ala Ala Asn
            230
```

<210> SEQ ID NO 7
<211> LENGTH: 255
<212> TYPE: PRT
<213> ORGANISM: Homo sapiens
<220> FEATURE:
<223> OTHER INFORMATION: Factor 7

<400> SEQUENCE: 7

```
Arg Ile Val Gly Gly Lys Val Cys Pro Lys Gly Glu Cys Pro Trp
                 5                  10                  15
Gln Val Leu Leu Leu Val Asn Gly Ala Gln Leu Cys Gly Gly Thr
             20                  25                  30
Leu Ile Asn Thr Ile Trp Val Val Ser Ala Ala His Cys Phe Asp
             35                  40                  45
Lys Ile Lys Asn Trp Arg Asn Leu Ile Ala Val Leu Gly Glu His
             50                  55                  60
Asp Leu Ser Glu His Asp Gly Asp Glu Gln Ser Arg Arg Val Ala
             65                  70                  75
Gln Val Ile Ile Pro Ser Thr Tyr Val Pro Gly Thr Thr Asn His
             80                  85                  90
```

```
Asp Ile Ala Leu Leu Arg Leu His Gln Pro Val Val Leu Thr Asp
                95                 100                105

His Val Val Pro Leu Cys Leu Pro Glu Arg Thr Phe Ser Glu Arg
               110                 115                120

Thr Leu Ala Phe Val Arg Phe Ser Leu Val Ser Gly Trp Gly Gln
               125                 130                135

Leu Leu Asp Arg Gly Ala Thr Ala Leu Glu Leu Met Val Leu Asn
               140                 145                150

Val Pro Arg Leu Met Thr Gln Asp Cys Leu Gln Gln Ser Arg Lys
               155                 160                165

Val Gly Asp Ser Pro Asn Ile Thr Glu Tyr Met Phe Cys Ala Gly
               170                 175                180

Tyr Ser Asp Gly Ser Lys Asp Ser Cys Lys Gly Asp Ser Gly Gly
               185                 190                195

Pro His Ala Thr His Tyr Arg Gly Thr Trp Tyr Leu Thr Gly Ile
               200                 205                210

Val Ser Trp Gly Gln Gly Cys Ala Thr Val Gly His Phe Gly Val
               215                 220                225

Tyr Thr Arg Val Ser Gln Tyr Ile Glu Trp Leu Gln Lys Leu Met
               230                 235                240

Arg Ser Glu Pro Arg Pro Gly Val Leu Leu Arg Ala Pro Phe Pro
               245                 250                255

<210> SEQ ID NO 8
<211> LENGTH: 253
<212> TYPE: PRT
<213> ORGANISM: Homo sapiens
<220> FEATURE:
<223> OTHER INFORMATION: Tissue plasminogen activator

<400> SEQUENCE: 8

Arg Ile Lys Gly Gly Leu Phe Ala Asp Ile Ala Ser His Pro Trp
                 5                  10                 15

Gln Ala Ala Ile Phe Ala Lys His Arg Arg Ser Pro Gly Glu Arg
                20                  25                 30

Phe Leu Cys Gly Gly Ile Leu Ile Ser Ser Cys Trp Ile Leu Ser
                35                  40                 45

Ala Ala His Cys Phe Gln Glu Arg Phe Pro Pro His His Leu Thr
                50                  55                 60

Val Ile Leu Gly Arg Thr Tyr Arg Val Val Pro Gly Glu Glu Glu
                65                  70                 75

Gln Lys Phe Glu Val Glu Lys Tyr Ile Val His Lys Glu Phe Asp
                80                  85                 90

Asp Asp Thr Tyr Asp Asn Asp Ile Ala Leu Leu Gln Leu Lys Ser
                95                 100                105

Asp Ser Ser Arg Cys Ala Gln Glu Ser Ser Val Val Arg Thr Val
               110                 115                120

Cys Leu Pro Pro Ala Asp Leu Gln Leu Pro Asp Trp Thr Glu Cys
               125                 130                135

Glu Leu Ser Gly Tyr Gly Lys His Glu Ala Leu Ser Pro Phe Tyr
               140                 145                150

Ser Glu Arg Leu Lys Glu Ala His Val Arg Leu Tyr Pro Ser Ser
               155                 160                165

Arg Cys Thr Ser Gln His Leu Leu Asn Arg Thr Val Thr Asp Asn
               170                 175                180

Met Leu Cys Ala Gly Asp Thr Arg Ser Gly Gly Pro Gln Ala Asn
```

```
                185                 190                 195
Leu His Asp Ala Cys Gln Gly Asp Ser Gly Gly Pro Leu Val Cys
            200                 205                 210

Leu Asn Asp Gly Arg Met Thr Leu Val Gly Ile Ile Ser Trp Gly
            215                 220                 225

Leu Gly Cys Gly Gln Lys Asp Val Pro Gly Val Tyr Thr Lys Val
            230                 235                 240

Thr Asn Tyr Leu Asp Trp Ile Arg Asp Asn Met Arg Pro
            245                 250

<210> SEQ ID NO 9
<211> LENGTH: 2900
<212> TYPE: DNA
<213> ORGANISM: Homo sapiens
<220> FEATURE:
<223> OTHER INFORMATION: SNC-19; GeneBank Accession No. #U20428

<400> SEQUENCE: 9
cgctgggtgg tgctggcagc cgtgctgatc ggcctcctct tggtcttgct ggggatcggc      60
ttcctggtgt ggcatttgca gtaccgggac gtgcgtgtcc agaaggtctt caatggctac     120
atgaggatca caaatgagaa ttttgtggat gcctacgaga actccaactc cactgagttt     180
gtaagcctgg ccagcaaggt gaaggacgcg ctgaagctgc tgtacagcgg agtcccattc     240
ctgggcccct accacaagga gtcggctgtg acggccttca gcgagggcag cgtcatcgcc     300
tactactggt ctgagttcag catcccgcag cacctggttg aggaggccga gcgcgtcatg     360
gccaggagcg cgtagtcatg ctgcccccgc gggcgcgctc cctgaagtcc tttgtggtca     420
cctcagtggt ggctttcccc acggactcca aaacagtaca gaggacccag acaacagct     480 gcagctttgg cctgcacgcc gcggtgtgga gctgatgcgc ttcaccacgc cggcttccct     540
gacagcccct accccgctca tgcccgctgc cagtgggctg cggggacgcg acgcagtgct     600
gagctactcg agctgactcg cagcttgact gcgcctcgac gagcgcggca gcgacctggt     660
gacgtgtaca caccctgag ccccatggag ccccacgcct ggtgagtgtg tggcacctac     720 cctcccttcct acaacctgac cttccactcc ctcccacgaa cgtcctgctc atcacactga     780
taaccaacac tgacgcggca tcccggcttt gaggccacct tcttccagct gcctaggatg     840
agcagctgtg gaggccgctt acgtaaagcc caggggacat caacagccc ctactaccca     900 ggccactacc cacccaacat tgactgcaca tggaaaattg aggtgcccaa caaccagcat     960
gtgaaggtgc gcttcaaatt cttctacctg ctggagcccg cgtgcctgc gggcacctgc    1020 cccaaggact acgtggagat caatgggag aaatactgcg agagaggtc ccagttcgtc    1080 gtcaccagca cagcaacaa gatcacagtt cgcttccact cagatcagtc ctacaccgac    1140
accggcttct tagctgaata cctctcctac gactccagtg acccatgccc ggggcagttc    1200
acgtgccgca cggggcggtg tatccggaag gagctgcgct gtgatggctg ggcgactgca    1260
ccgaccacag cgatgagctc aactgcagtt gcgacgccgg ccaccagttc acgtgcaaga    1320
gcaagttctg caagctcttc tgggtctgcg acagtgtgaa cgagtgcgga cacaacagcg    1380
acgagcaggg ttgcatttgt ccggacccag accttcaggt gttccaatgg aagtgcctc    1440 tcgaaaagcc agcagtgcaa tggaaggac gactgtgggg acgggtccga cgaggcctcc    1500
tgccccaagg tgaacgtcgt cacttgtacc aaacacacct accgctgcct caatgggctc    1560
tgcttgagca gggcaaccc tgagtgtgac gggaaggagg actgtagcga cggctcagat    1620
gagaaggact gcgactgtgg gctgcggtca ttcacgagac aggctcgtgt tgttgggggc    1680
```

-continued

```
acggatgcgg atgagggcga gtggccctgg caggtaagcc tgcatgctct gggccagggc    1740
cacatctgcg gtgcttccct catctctccc aactggctgg tctctgccgc acactgctac    1800
atcgatgaca gaggattcag gtactcagac cccacgcagg acggccttcc tgggcttgca    1860
cgaccagagc cagcgcaggc cctggggtgc aggagcgcag gctcaagcgc atcatctccc    1920
accccttctt caatgacttc accttcgact atgacatcgc gctgctggag ctggagaaac    1980
cggcagagta cagctccatg gtgcggccca tctgcctgcc ggacgcctgc catgtcttcc    2040
ctgccggcaa ggccatctgg gtcacgggct ggggacacac ccagtatgga ggcactggcg    2100
cgctgatcct gcaaaagggt gagatccgcg tcatcaacca gaccacctgc gagaacctcc    2160
tgccgcagca gatcacgccg cgcatgatgt gcgtgggctt cctcagcggc ggcgtggact    2220
cctgccaggg tgattccggg ggaccccctgt ccagcgtgga ggcggatggg cggatcttcc    2280
aggccggtgt ggtgagctgg ggagacgctg cgctcagagg aacaagccag gcgtgtacac    2340
aaggctccct ctgtttcggg aatggatcaa agagaacact ggggtatagg gccggggcc     2400 acccaaatgt gtacacctgc ggggccaccc atcgtccacc ccagtgtgca cgcctgcagg    2460
ctggagactc gcgcaccgtg acctgcacca gcgccccaga acatacactg tgaactcatc    2520
tccaggctca aatctgctag aaaacctctc gcttcctcag cctccaaagt ggagctggga    2580
gggtagaagg ggaggaacac tggtggttct actgacccaa ctggggcaag gtttgaagca    2640
cagctccggc agcccaagtg ggcgaggacg cgtttgtgca tactgccctg ctctatacac    2700
ggaagacctg gatctctagt gagtgtgact gccggatctg gctgtggtcc ttggccacgc    2760
ttcttgagga agcccaggct cggaggaccc tggaaaacag acgggtctga gactgaaaat    2820
ggtttaccag ctcccaggtg acttcagtgt gtgtattgtg taaatgagta aacattttta    2880
tttcttttta aaaaaaaaa                                                 2900
```

<210> SEQ ID NO 10
<211> LENGTH: 902
<212> TYPE: PRT
<213> ORGANISM: Mus musculus
<220> FEATURE:
<223> OTHER INFORMATION: Epithin

<400> SEQUENCE: 10

```
Met Gly Ser Asn Arg Gly Arg Lys Ala Gly Gly Gly Ser Gln Asp
                5                   10                  15

Phe Gly Ala Gly Leu Lys Tyr Asp Ser Arg Leu Glu Asn Met Asn
                20                  25                  30

Gly Phe Glu Glu Gly Val Glu Phe Leu Pro Ala Asn Asn Ala Lys
                35                  40                  45

Lys Val Glu Lys Arg Gly Pro Arg Arg Trp Val Val Leu Val Ala
                50                  55                  60

Val Leu Phe Ser Phe Leu Leu Ser Leu Met Ala Gly Leu Leu
                65                  70                  75

Val Trp His Phe His Tyr Arg Asn Val Arg Val Gln Lys Val Phe
                80                  85                  90

Asn Gly His Leu Arg Ile Thr Asn Glu Ile Phe Leu Asp Ala Tyr
                95                  100                 105

Glu Asn Ser Thr Ser Thr Glu Phe Ile Ser Leu Ala Ser Gln Val
                110                 115                 120

Lys Glu Ala Leu Lys Leu Leu Tyr Asn Glu Val Pro Val Leu Gly
                125                 130                 135

Pro Tyr His Lys Lys Ser Ala Val Thr Ala Phe Ser Glu Gly Ser
```

```
                    140                 145                 150
Val Ile Ala Tyr Tyr Trp Ser Glu Phe Ser Ile Pro Pro His Leu
                155                 160                 165
Ala Glu Glu Val Asp Arg Ala Met Ala Val Glu Arg Val Val Thr
                170                 175                 180
Leu Pro Pro Arg Ala Arg Ala Leu Lys Ser Phe Val Leu Thr Ser
                185                 190                 195
Val Val Ala Phe Pro Ile Asp Pro Arg Met Leu Gln Arg Thr Gln
                200                 205                 210
Asp Asn Ser Cys Ser Phe Ala Leu His Ala His Gly Ala Ala Val
                215                 220                 225
Thr Arg Phe Thr Thr Pro Gly Phe Pro Asn Ser Pro Tyr Pro Ala
                230                 235                 240
His Ala Arg Cys Gln Trp Val Leu Arg Gly Asp Ala Asp Ser Val
                245                 250                 255
Leu Ser Leu Thr Phe Arg Ser Phe Asp Val Ala Pro Cys Asp Glu
                260                 265                 270
His Gly Ser Asp Leu Val Thr Val Tyr Asp Ser Leu Ser Pro Met
                275                 280                 285
Glu Pro His Ala Val Val Arg Leu Cys Gly Thr Phe Ser Pro Ser
                290                 295                 300
Tyr Asn Leu Thr Phe Leu Ser Ser Gln Asn Val Phe Leu Val Thr
                305                 310                 315
Leu Ile Thr Asn Thr Gly Arg Arg His Leu Gly Phe Glu Ala Thr
                320                 325                 330
Phe Phe Gln Leu Pro Lys Met Ser Ser Cys Gly Gly Val Leu Ser
                335                 340                 345
Asp Thr Gln Gly Thr Phe Ser Ser Pro Tyr Tyr Pro Gly His Tyr
                350                 355                 360
Pro Pro Asn Ile Asn Cys Thr Trp Asn Ile Lys Val Pro Asn Asn
                365                 370                 375
Arg Asn Val Lys Val Arg Phe Lys Leu Phe Tyr Leu Val Asp Pro
                380                 385                 390
Asn Val Pro Val Gly Ser Cys Thr Lys Asp Tyr Val Glu Ile Asn
                395                 400                 405
Gly Glu Lys Gly Ser Gly Glu Arg Ser Gln Phe Val Val Ser Ser
                410                 415                 420
Asn Ser Ser Lys Ile Thr Val His Phe His Ser Asp His Ser Tyr
                425                 430                 435
Thr Asp Thr Gly Phe Leu Ala Glu Tyr Leu Ser Tyr Asp Ser Asn
                440                 445                 450
Asp Pro Cys Pro Gly Met Phe Met Cys Lys Thr Gly Arg Cys Ile
                455                 460                 465
Arg Lys Glu Leu Arg Cys Asp Gly Trp Ala Asp Cys Pro Asp Tyr
                470                 475                 480
Ser Asp Glu Arg Tyr Cys Arg Cys Asn Ala Thr His Gln Phe Thr
                485                 490                 495
Cys Lys Asn Gln Phe Cys Lys Pro Leu Phe Trp Val Cys Asp Ser
                500                 505                 510
Val Asn Asp Cys Gly Asp Gly Ser Asp Glu Glu Gly Cys Ser Cys
                515                 520                 525
Pro Ala Gly Ser Phe Lys Cys Ser Asn Gly Lys Cys Leu Pro Gln
                530                 535                 540
```

```
Ser Gln Lys Cys Asn Gly Lys Asp Asn Cys Gly Asp Gly Ser Asp
                545                 550                 555
Glu Ala Ser Cys Asp Ser Val Asn Val Val Ser Cys Thr Lys Tyr
                560                 565                 570
Thr Tyr Arg Cys Gln Asn Gly Leu Cys Leu Ser Lys Gly Asn Pro
                575                 580                 585
Glu Cys Asp Gly Lys Thr Asp Cys Ser Asp Gly Ser Asp Glu Lys
                590                 595                 600
Asn Cys Asp Cys Gly Leu Arg Ser Phe Thr Lys Gln Ala Arg Val
                605                 610                 615
Val Gly Gly Thr Asn Ala Asp Glu Gly Glu Trp Pro Trp Gln Val
                620                 625                 630
Ser Leu His Ala Leu Gly Gln Gly His Leu Cys Gly Ala Ser Leu
                635                 640                 645
Ile Ser Pro Asp Trp Leu Val Ser Ala Ala His Cys Phe Gln Asp
                650                 655                 660
Asp Lys Asn Phe Lys Tyr Ser Asp Tyr Thr Met Trp Thr Ala Phe
                665                 670                 675
Leu Gly Leu Leu Asp Gln Ser Lys Arg Ser Ala Ser Gly Val Gln
                680                 685                 690
Glu Leu Lys Leu Lys Arg Ile Ile Thr His Pro Ser Phe Asn Asp
                695                 700                 705
Phe Thr Phe Asp Tyr Asp Ile Ala Leu Leu Glu Leu Glu Lys Ser
                710                 715                 720
Val Glu Tyr Ser Thr Val Val Arg Pro Ile Cys Leu Pro Asp Ala
                725                 730                 735
Thr His Val Phe Pro Ala Gly Lys Ala Ile Trp Val Thr Gly Trp
                740                 745                 750
Gly His Thr Lys Glu Gly Gly Thr Gly Ala Leu Ile Leu Gln Lys
                755                 760                 765
Gly Glu Ile Arg Val Ile Asn Gln Thr Thr Cys Glu Asp Leu Met
                770                 775                 780
Pro Gln Gln Ile Thr Pro Arg Met Met Cys Val Gly Phe Leu Ser
                785                 790                 795
Gly Gly Val Asp Ser Cys Gln Gly Asp Ser Gly Gly Pro Leu Ser
                800                 805                 810
Ser Ala Glu Lys Asp Gly Arg Met Phe Gln Ala Gly Val Val Ser
                815                 820                 825
Trp Gly Glu Gly Cys Ala Gln Arg Asn Lys Pro Gly Val Tyr Thr
                830                 835                 840
Arg Leu Pro Cys Ser Ser Gly Leu Asp Gln Arg Ala His Trp Gly
                845                 850                 855
Ile Ala Ala Trp Thr Asp Ser Arg Pro Gln Thr Pro Thr Gly Met
                860                 865                 870
Pro Asp Met His Thr Trp Ile Gln Glu Arg Asn Thr Asp Asp Ile
                875                 880                 885
Tyr Ala Val Ala Ser Pro Pro Gln His Asn Pro Asp Cys Glu Leu
                890                 895                 900
His Pro

<210> SEQ ID NO 11
<211> LENGTH: 23
<212> TYPE: DNA
<213> ORGANISM: Artificial sequence
<220> FEATURE:
```

```
<221> NAME/KEY: n=Inosine
<222> LOCATION: 6, 9, 12, 15, 18
<223> OTHER INFORMATION: Degenerate oligonucleotide primer

<400> SEQUENCE: 11
tgggtngtna cngcngcnca ytg                                       23

<210> SEQ ID NO 12
<211> LENGTH: 20
<212> TYPE: DNA
<213> ORGANISM: Artificial sequence
<220> FEATURE:
<221> NAME/KEY: n=Inosine
<222> LOCATION: 3, 6, 9, 12, 18
<223> OTHER INFORMATION: Degenerate oligonucleotide primer

<400> SEQUENCE: 12
arnggnccnc cnswrtcncc                                           20

<210> SEQ ID NO 13
<211> LENGTH: 12
<212> TYPE: PRT
<213> ORGANISM: Homo sapiens
<220> FEATURE:
<223> OTHER INFORMATION: Fragment of TADG-15

<400> SEQUENCE: 13

Leu Phe Arg Asp Trp Ile Lys Glu Asn Thr Gly Val
                5                   10

<210> SEQ ID NO 14
<211> LENGTH: 20
<212> TYPE: DNA
<213> ORGANISM: Artificial sequence
<220> FEATURE:
<223> OTHER INFORMATION: TADG-15 forward oligonucleotide primer

<400> SEQUENCE: 14
atgacagagg attcaggtac                                           20

<210> SEQ ID NO 15
<211> LENGTH: 20
<212> TYPE: DNA
<213> ORGANISM: Artificial sequence
<220> FEATURE:
<223> OTHER INFORMATION: TADG-15 reverse oligonucleotide primer

<400> SEQUENCE: 15
gaaggtgaag tcattgaaga                                           20

<210> SEQ ID NO 16
<211> LENGTH: 20
<212> TYPE: DNA
<213> ORGANISM: Artificial sequence
<220> FEATURE:
<223> OTHER INFORMATION: (-tubulin forward oligonucleotide primer

<400> SEQUENCE: 16
cgcatcaacg tgtactacaa                                           20

<210> SEQ ID NO 17
<211> LENGTH: 20
<212> TYPE: DNA
<213> ORGANISM: Artificial sequence
<220> FEATURE:
<223> OTHER INFORMATION: (-tubulin reverse oligonucleotide primer

<400> SEQUENCE: 17
```
tacgagctgg tggactgaga                                              20

<210> SEQ ID NO 18
<211> LENGTH: 3147
<212> TYPE: RNA
<213> ORGANISM: Artificial sequence
<220> FEATURE:
<223> OTHER INFORMATION: Antisense of TADG-15

<400> SEQUENCE: 18
uuuuuuuuuu uuuuuuuuua aaagaaaua aauuguuuua cccauuuaca           50
caaauacaca cacugaaguc cacccuggga gcugguaaaa caauuucagu          100
cucagacccg ucuguuuucc aggguccucc gagccugggc uuccucaaga          150
gcguggccca agggccccac agcccagauc cggcagcccc accaccuuca          200
cugaggaggc uccgaagcuc cguucccgcu gcuccuuaca gacaggggag          250
gcagauauac acaaacgcgc ucggcccag cuuggggcug gcggggggagg          300 cugugucuuc aaaccuuugc ccccaguugg gucaguagaa ccaccagugu          350 ccucccuuc uaccucccag cuccacuuug gaggcugagg aagcgagagg           400
uuuucuaggc agauuuggag cccuggagau ugaguucaca guguauguuc          450 uggggcgcu ggugcagucu gcguccagu uccagccug caggcgugca             500 cacuggggug gacgauggguu ggccccgcag guguacacau uugggguggcc        550 ccggccccua uacccagug uucucuuuga uccagcccg aaacagaggg            600 agccuugugu acacgccugg cuuguuccuc ugagcgcagc cgucuccca           650 gcucaccaca ccggccugga agauccgccc auccgccucc acgcuggaca          700 ggggucccc ggaaucaccc uggcaggagu ccacgccgcc gcugaggaag           750
cccacgcaca ucaugcgcgg cgugaucugc ugcggcagga gguucucgca          800 ggugguucugg uugaugacgc ggaucucacc cuuuugcagg aucagcgcgc         850
cagugccucc auacuggggug ugucccccagc ccgugaccca gauggccuug        900
ccggcaggga agacauggga ggcguccggc aggcagaugg gccgcaccau          950
ggagcuguac ucugccgguu ucuccagcuc cagcagcgcg augucauagu         1000
cgaaggugaa gucauugaag aaggggguggg agaugaugcg cuugagccug        1050
cgcuccugca cccagggggc gcugcgcugg cucuggucgu gcaagcccag         1100
gaaggccguc cacucgcugg ggucugagua ccugaauccu cugucaucga         1150
uguagcagug ugcggcagag accagccagu ugggagagau gagggaagca         1200
ccgcagaugu ggcccuggcc cagagcaugc aggcuuaccu gccagggcca         1250
cucgcccuca uccgcauccg ugcccccaac aacacgagcc ugucucguga         1300
augaccgcag cccacagucg caguccuucu caucugagcc gucgcuacag         1350
uccuccuucc cgucacacuc aggguugccc uugcucaagc agagcccauu         1400
gaggcagcgg uaggugug uggguacaagu gacgacguuc accuuggggc         1450
aggaggccuc gucggacccg uccccacagu cguccuuccc auugcacugc         1500
uggcuuuucg agaggcacuu cccauuggaa caccugaagg ucugggccgg         1550
acaacugcac cccugcucgu cgcuguuguc uccgcagucg uucacacugu         1600
cgcagaccca gaagaggggc uugcagaacu guucaucga cgugaacugg          1650 uggccggcgu cgcaacugca guugagcuca ucgcuguggu cggugcaguc         1700

```
ggcccagcca ucacagcgca gcuccuuccg gauacaccgc cccgugcggc      1750
acgugaacug ccccgggcau gggucacugg agucguagga gagguauuca      1800
gcuaagaagc cggugucggu guaggacuga ucugagugga agcgaacugu      1850
gaucuuguug cuguugcugg ugacgacgaa cuggaccuc ucuccgcagu       1900 auuucccccc auugaucucc acguaguccu ugggggcaggu gcccgcaggc     1950 acgccgggcu ccagcaggua gaagaauuug aagcucaccu ucacaugcug      2000 guuguuggc accucaaugu uccaugugca gucaauguug ggugggu agu      2050 ggccugggua guaggggcug uugaaugucc ccugggcuuu acguaagcgg      2100
ccuccacagc ugcucauccu aggcagcugg aagaaggugg ccucaaagcc      2150
gggaugccgc cgcucagugu ugguuaucag ugugaugagc aggacguucu      2200
gggaggagug gaaggucagg uuguaggagg gaggguaggu gccacacaac      2250
ugcaccaggg cgugggggcuc caugggggcuc agggguguugu acaccgucac   2300 cagguucgcug ccgcgcucgu cgcaggacgc aaggucaaag cugcggaagg     2350
ugaggcucag cacugagucg gcgucccccc gcagggccca cuggcagcgg      2400
gcaugagcgg gguaggggcu gucagggaag ccgggcgugg ugaagcgcau      2450
cagcuccaca ccgcgggcgu gcaggccaaa gcugcagcug uugucccuggg    2500 uccucuguac uguuuuggag uccguggga aagccaccac ugaggugacc       2550
acaaaggacu ucagggagcg cgcccgcggg ggcagcauga cuacgcgcuc      2600
cucggccaug acgcgcucgg ccuccuccac caggugcugc gggaugcuga     2650
acucagacca guaguaggcg augacgcugc ccucgcugaa ggccgucaca      2700
gccgacuccu ugugguaggg gcccaggaau gggacuccgc uguacagcag      2750
cuucagcgcg uccuucaccu ugcuggccag gcuuacaaac ucagguggagu   2800 uggaguucuc guaggcaucc acaaaauucu cauuugugau ccucauguag      2850
ccauugaaga ccuucuggac acgcacguc cgguacugca aaugccacac       2900
caggaagccg auccccagca agaccaagag gaggccgauc agcacggcug     2950
ccagcaccac ccagcgccc gggccaugcu uuuccaccuu cuugacguug      3000
uugacuggca ggaacuccac gccuuccucc aagccauuca cuuucucgug      3050
ccgggaguug uacuugaguc ccgcgccgaa gucuucggg ccccuccgc         3100 ccuugcgggc ccgaucgcuc cccaugguac cccgaggccg cucuuga        3147
```

<210> SEQ ID NO 19
<211> LENGTH: 9
<212> TYPE: PRT
<213> ORGANISM: Homo sapiens
<220> FEATURE:
<223> OTHER INFORMATION: Residues 68-76 of the TADG-15 protein

<400> SEQUENCE: 19

Val Leu Leu Gly Ile Gly Phe Leu Val
                5

<210> SEQ ID NO 20
<211> LENGTH: 9
<212> TYPE: PRT
<213> ORGANISM: Homo sapiens
<220> FEATURE:
<223> OTHER INFORMATION: Residues 126-134 of the TADG-15 protein

```
<400> SEQUENCE: 20

Leu Leu Tyr Ser Gly Val Pro Phe Leu
                5

<210> SEQ ID NO 21
<211> LENGTH: 9
<212> TYPE: PRT
<213> ORGANISM: Homo sapiens
<220> FEATURE:
<223> OTHER INFORMATION: Residues 644-652 of the TADG-15 protein

<400> SEQUENCE: 21

Ser Leu Ile Ser Pro Asn Trp Leu Val
                5

<210> SEQ ID NO 22
<211> LENGTH: 9
<212> TYPE: PRT
<213> ORGANISM: Homo sapiens
<220> FEATURE:
<223> OTHER INFORMATION: Residues 379-387 of the TADG-15 protein

<400> SEQUENCE: 22

Lys Val Ser Phe Lys Phe Phe Tyr Leu
                5

<210> SEQ ID NO 23
<211> LENGTH: 9
<212> TYPE: PRT
<213> ORGANISM: Homo sapiens
<220> FEATURE:
<223> OTHER INFORMATION: Residues 386-394 of the TADG-15 protein

<400> SEQUENCE: 23

Tyr Leu Leu Glu Pro Gly Val Pro Ala
                5

<210> SEQ ID NO 24
<211> LENGTH: 9
<212> TYPE: PRT
<213> ORGANISM: Homo sapiens
<220> FEATURE:
<223> OTHER INFORMATION: Residues 257-265 of the TADG-15 protein

<400> SEQUENCE: 24

Ser Leu Thr Phe Arg Ser Phe Asp Leu
                5

<210> SEQ ID NO 25
<211> LENGTH: 9
<212> TYPE: PRT
<213> ORGANISM: Homo sapiens
<220> FEATURE:
<223> OTHER INFORMATION: Residues 762-770 of the TADG-15 protein

<400> SEQUENCE: 25

Ile Leu Gln Lys Gly Glu Ile Arg Val
                5

<210> SEQ ID NO 26
<211> LENGTH: 9
<212> TYPE: PRT
<213> ORGANISM: Homo sapiens
<220> FEATURE:
<223> OTHER INFORMATION: Residues 841-849 of the TADG-15 protein

<400> SEQUENCE: 26
```

```
Arg Leu Pro Leu Phe Arg Asp Trp Ile
                5

<210> SEQ ID NO 27
<211> LENGTH: 9
<212> TYPE: PRT
<213> ORGANISM: Homo sapiens
<220> FEATURE:
<223> OTHER INFORMATION: Residues 64-72 of the TADG-15 protein

<400> SEQUENCE: 27

Gly Leu Leu Leu Val Leu Leu Gly Ile
                5

<210> SEQ ID NO 28
<211> LENGTH: 9
<212> TYPE: PRT
<213> ORGANISM: Homo sapiens
<220> FEATURE:
<223> OTHER INFORMATION: Residues 57-65 of the TADG-15 protein

<400> SEQUENCE: 28

Val Leu Ala Ala Val Leu Ile Gly Leu
                5

<210> SEQ ID NO 29
<211> LENGTH: 9
<212> TYPE: PRT
<213> ORGANISM: Homo sapiens
<220> FEATURE:
<223> OTHER INFORMATION: Residues 67-75 of the TADG-15 protein

<400> SEQUENCE: 29

Leu Val Leu Leu Gly Ile Gly Phe Leu
                5

<210> SEQ ID NO 30
<211> LENGTH: 9
<212> TYPE: PRT
<213> ORGANISM: Homo sapiens
<220> FEATURE:
<223> OTHER INFORMATION: Residues 379-387 of the TADG-15 protein

<400> SEQUENCE: 30

Lys Val Ser Phe Lys Phe Phe Tyr Leu
                5

<210> SEQ ID NO 31
<211> LENGTH: 9
<212> TYPE: PRT
<213> ORGANISM: Homo sapiens
<220> FEATURE:
<223> OTHER INFORMATION: Residues 126-134 of the TADG-15 protein

<400> SEQUENCE: 31

Leu Leu Tyr Ser Gly Val Pro Phe Leu
                5

<210> SEQ ID NO 32
<211> LENGTH: 9
<212> TYPE: PRT
<213> ORGANISM: Homo sapiens
<220> FEATURE:
<223> OTHER INFORMATION: Residues 88-96 of the TADG-15 protein

<400> SEQUENCE: 32

Lys Val Phe Asn Gly Tyr Met Arg Ile
                5
```

```
<210> SEQ ID NO 33
<211> LENGTH: 9
<212> TYPE: PRT
<213> ORGANISM: Homo sapiens
<220> FEATURE:
<223> OTHER INFORMATION: Residues 670-678 of the TADG-15 protein

<400> SEQUENCE: 33

Thr Gln Trp Thr Ala Phe Leu Gly Leu
                 5

<210> SEQ ID NO 34
<211> LENGTH: 9
<212> TYPE: PRT
<213> ORGANISM: Homo sapiens
<220> FEATURE:
<223> OTHER INFORMATION: Residues 119-127 of the TADG-15 protein

<400> SEQUENCE: 34

Lys Val Lys Asp Ala Leu Lys Leu Leu
                 5

<210> SEQ ID NO 35
<211> LENGTH: 9
<212> TYPE: PRT
<213> ORGANISM: Homo sapiens
<220> FEATURE:
<223> OTHER INFORMATION: Residues 60-68 of the TADG-15 protein

<400> SEQUENCE: 35

Ala Val Leu Ile Gly Leu Leu Leu Val
                 5

<210> SEQ ID NO 36
<211> LENGTH: 9
<212> TYPE: PRT
<213> ORGANISM: Homo sapiens
<220> FEATURE:
<223> OTHER INFORMATION: Residues 62-70 of the TADG-15 protein

<400> SEQUENCE: 36

Leu Ile Gly Leu Leu Leu Val Leu Leu
                 5

<210> SEQ ID NO 37
<211> LENGTH: 9
<212> TYPE: PRT
<213> ORGANISM: Homo sapiens
<220> FEATURE:
<223> OTHER INFORMATION: Residues 57-65 of the TADG-15 protein

<400> SEQUENCE: 37

Val Leu Ala Ala Val Leu Ile Gly Leu
                 5

<210> SEQ ID NO 38
<211> LENGTH: 9
<212> TYPE: PRT
<213> ORGANISM: Homo sapiens
<220> FEATURE:
<223> OTHER INFORMATION: Residues 61-69 of the TADG-15 protein

<400> SEQUENCE: 38

Val Leu Ile Gly Leu Leu Leu Val Leu
                 5
```

```
<210> SEQ ID NO 39
<211> LENGTH: 9
<212> TYPE: PRT
<213> ORGANISM: Homo sapiens
<220> FEATURE:
<223> OTHER INFORMATION: Residues 146-154 of the TADG-15 protein

<400> SEQUENCE: 39

Phe Ser Glu Gly Ser Val Ile Ala Tyr
                5

<210> SEQ ID NO 40
<211> LENGTH: 9
<212> TYPE: PRT
<213> ORGANISM: Homo sapiens
<220> FEATURE:
<223> OTHER INFORMATION: Residues 658-666 of the TADG-15 protein

<400> SEQUENCE: 40

Tyr Ile Asp Asp Arg Gly Phe Arg Tyr
                5

<210> SEQ ID NO 41
<211> LENGTH: 9
<212> TYPE: PRT
<213> ORGANISM: Homo sapiens
<220> FEATURE:
<223> OTHER INFORMATION: Residues 449-457 of the TADG-15 protein

<400> SEQUENCE: 41

Ser Ser Asp Pro Cys Pro Gly Gln Phe
                5

<210> SEQ ID NO 42
<211> LENGTH: 9
<212> TYPE: PRT
<213> ORGANISM: Homo sapiens
<220> FEATURE:
<223> OTHER INFORMATION: Residues 401-409 of the TADG-15 protein

<400> SEQUENCE: 42

Tyr Val Glu Ile Asn Gly Glu Lys Tyr
                5

<210> SEQ ID NO 43
<211> LENGTH: 9
<212> TYPE: PRT
<213> ORGANISM: Homo sapiens
<220> FEATURE:
<223> OTHER INFORMATION: Residues 387-395 of the TADG-15 protein

<400> SEQUENCE: 43

Leu Leu Glu Pro Gly Val Pro Ala Gly
                5

<210> SEQ ID NO 44
<211> LENGTH: 9
<212> TYPE: PRT
<213> ORGANISM: Homo sapiens
<220> FEATURE:
<223> OTHER INFORMATION: Residues 553-561 of the TADG-15 protein

<400> SEQUENCE: 44

Gly Ser Asp Glu Ala Ser Cys Pro Lys
                5

<210> SEQ ID NO 45
<211> LENGTH: 9
```

```
<212> TYPE: PRT
<213> ORGANISM: Homo sapiens
<220> FEATURE:
<223> OTHER INFORMATION: Residues 97-105 of the TADG-15 protein

<400> SEQUENCE: 45

Thr Asn Glu Asn Phe Val Asp Ala Tyr
                5

<210> SEQ ID NO 46
<211> LENGTH: 9
<212> TYPE: PRT
<213> ORGANISM: Homo sapiens
<220> FEATURE:
<223> OTHER INFORMATION: Residues 110-118 of the TADG-15 protein

<400> SEQUENCE: 46

Ser Thr Glu Phe Val Ser Leu Ala Ser
                5

<210> SEQ ID NO 47
<211> LENGTH: 9
<212> TYPE: PRT
<213> ORGANISM: Homo sapiens
<220> FEATURE:
<223> OTHER INFORMATION: Residues 811-819 of the TADG-15 protein

<400> SEQUENCE: 47

Ser Val Glu Ala Asp Gly Arg Ile Phe
                5

<210> SEQ ID NO 48
<211> LENGTH: 9
<212> TYPE: PRT
<213> ORGANISM: Homo sapiens
<220> FEATURE:
<223> OTHER INFORMATION: Residues 666-674 of the TADG-15 protein

<400> SEQUENCE: 48

Tyr Ser Asp Pro Thr Gln Trp Thr Ala
                5

<210> SEQ ID NO 49
<211> LENGTH: 9
<212> TYPE: PRT
<213> ORGANISM: Homo sapiens
<220> FEATURE:
<223> OTHER INFORMATION: Residues 709-717 of the TADG-15 protein

<400> SEQUENCE: 49

Asp Tyr Asp Ile Ala Leu Leu Glu Leu
                5

<210> SEQ ID NO 50
<211> LENGTH: 9
<212> TYPE: PRT
<213> ORGANISM: Homo sapiens
<220> FEATURE:
<223> OTHER INFORMATION: Residues 408-416 of the TADG-15 protein

<400> SEQUENCE: 50

Lys Tyr Cys Gly Glu Arg Ser Gln Phe
                5

<210> SEQ ID NO 51
<211> LENGTH: 9
<212> TYPE: PRT
<213> ORGANISM: Homo sapiens
```

```
<220> FEATURE:
<223> OTHER INFORMATION: Residues 754-762 of the TADG-15 protein

<400> SEQUENCE: 51

Gln Tyr Gly Gly Thr Gly Ala Leu Ile
                5

<210> SEQ ID NO 52
<211> LENGTH: 9
<212> TYPE: PRT
<213> ORGANISM: Homo sapiens
<220> FEATURE:
<223> OTHER INFORMATION: Residues 153-161 of the TADG-15 protein

<400> SEQUENCE: 52

Ala Tyr Tyr Trp Ser Glu Phe Ser Ile
                5

<210> SEQ ID NO 53
<211> LENGTH: 9
<212> TYPE: PRT
<213> ORGANISM: Homo sapiens
<220> FEATURE:
<223> OTHER INFORMATION: Residues 722-730 of the TADG-15 protein

<400> SEQUENCE: 53

Glu Tyr Ser Ser Met Val Arg Pro Ile
                5

<210> SEQ ID NO 54
<211> LENGTH: 9
<212> TYPE: PRT
<213> ORGANISM: Homo sapiens
<220> FEATURE:
<223> OTHER INFORMATION: Residues 326-334 of the TADG-15 protein

<400> SEQUENCE: 54

Gly Phe Glu Ala Thr Phe Phe Gln Leu
                5

<210> SEQ ID NO 55
<211> LENGTH: 9
<212> TYPE: PRT
<213> ORGANISM: Homo sapiens
<220> FEATURE:
<223> OTHER INFORMATION: Residues 304-312 of the TADG-15 protein

<400> SEQUENCE: 55

Thr Phe His Ser Ser Gln Asn Val Leu
                5

<210> SEQ ID NO 56
<211> LENGTH: 9
<212> TYPE: PRT
<213> ORGANISM: Homo sapiens
<220> FEATURE:
<223> OTHER INFORMATION: Residues 707-715 of the TADG-15 protein

<400> SEQUENCE: 56

Thr Phe Asp Tyr Asp Ile Ala Leu Leu
                5

<210> SEQ ID NO 57
<211> LENGTH: 9
<212> TYPE: PRT
<213> ORGANISM: Homo sapiens
<220> FEATURE:
<223> OTHER INFORMATION: Residues 21-29 of the TADG-15 protein
```

-continued

```
<400> SEQUENCE: 57

Lys Tyr Asn Ser Arg His Glu Lys Val
                5

<210> SEQ ID NO 58
<211> LENGTH: 9
<212> TYPE: PRT
<213> ORGANISM: Homo sapiens
<220> FEATURE:
<223> OTHER INFORMATION: Residues 665-673 of the TADG-15 protein

<400> SEQUENCE: 58

Arg Tyr Ser Asp Pro Thr Gln Trp Thr
                5

<210> SEQ ID NO 59
<211> LENGTH: 9
<212> TYPE: PRT
<213> ORGANISM: Homo sapiens
<220> FEATURE:
<223> OTHER INFORMATION: Residues 686-694 of the TADG-15 protein

<400> SEQUENCE: 59

Ala Pro Gly Val Gln Glu Arg Arg Leu
                5

<210> SEQ ID NO 60
<211> LENGTH: 9
<212> TYPE: PRT
<213> ORGANISM: Homo sapiens
<220> FEATURE:
<223> OTHER INFORMATION: Residues 12-20 of the TADG-15 protein

<400> SEQUENCE: 60

Gly Pro Lys Asp Phe Gly Ala Gly Leu
                5

<210> SEQ ID NO 61
<211> LENGTH: 9
<212> TYPE: PRT
<213> ORGANISM: Homo sapiens
<220> FEATURE:
<223> OTHER INFORMATION: Residues 668-676 of the TADG-15 protein

<400> SEQUENCE: 61

Asp Pro Thr Gln Trp Thr Ala Phe Leu
                5

<210> SEQ ID NO 62
<211> LENGTH: 9
<212> TYPE: PRT
<213> ORGANISM: Homo sapiens
<220> FEATURE:
<223> OTHER INFORMATION: Residues 461-469 of the TADG-15 protein

<400> SEQUENCE: 62

Thr Gly Arg Cys Ile Arg Lys Glu Leu
                5

<210> SEQ ID NO 63
<211> LENGTH: 9
<212> TYPE: PRT
<213> ORGANISM: Homo sapiens
<220> FEATURE:
<223> OTHER INFORMATION: Residues 59-67 of the TADG-15 protein

<400> SEQUENCE: 63
```

Ala Ala Val Leu Ile Gly Leu Leu Leu
                5

<210> SEQ ID NO 64
<211> LENGTH: 9
<212> TYPE: PRT
<213> ORGANISM: Homo sapiens
<220> FEATURE:
<223> OTHER INFORMATION: Residues 379-387 of the TADG-15 protein

<400> SEQUENCE: 64

Lys Val Ser Phe Lys Phe Phe Tyr Leu
                5

<210> SEQ ID NO 65
<211> LENGTH: 9
<212> TYPE: PRT
<213> ORGANISM: Homo sapiens
<220> FEATURE:
<223> OTHER INFORMATION: Residues 119-127 of the TADG-15 protein

<400> SEQUENCE: 65

Lys Val Lys Asp Ala Leu Lys Leu Leu
                5

<210> SEQ ID NO 66
<211> LENGTH: 9
<212> TYPE: PRT
<213> ORGANISM: Homo sapiens
<220> FEATURE:
<223> OTHER INFORMATION: Residues 780-788 of the TADG-15 protein

<400> SEQUENCE: 66

Leu Pro Gln Gln Ile Thr Pro Arg Met
                5

<210> SEQ ID NO 67
<211> LENGTH: 9
<212> TYPE: PRT
<213> ORGANISM: Homo sapiens
<220> FEATURE:
<223> OTHER INFORMATION: Residues 67-75 of the TADG-15 protein

<400> SEQUENCE: 67

Leu Val Leu Leu Gly Ile Gly Phe Leu
                5

<210> SEQ ID NO 68
<211> LENGTH: 9
<212> TYPE: PRT
<213> ORGANISM: Homo sapiens
<220> FEATURE:
<223> OTHER INFORMATION: Residues 283-291 of the TADG-15 protein

<400> SEQUENCE: 68

Ser Pro Met Glu Pro His Ala Leu Val
                5

<210> SEQ ID NO 69
<211> LENGTH: 9
<212> TYPE: PRT
<213> ORGANISM: Homo sapiens
<220> FEATURE:
<223> OTHER INFORMATION: Residues 12-20 of the TADG-15 protein

<400> SEQUENCE: 69

Gly Pro Lys Asp Phe Gly Ala Gly Leu

```
<210> SEQ ID NO 70
<211> LENGTH: 9
<212> TYPE: PRT
<213> ORGANISM: Homo sapiens
<220> FEATURE:
<223> OTHER INFORMATION: Residues 257-265 of the TADG-15 protein

<400> SEQUENCE: 70

Ser Leu Thr Phe Arg Ser Phe Asp Leu
                 5

<210> SEQ ID NO 71
<211> LENGTH: 9
<212> TYPE: PRT
<213> ORGANISM: Homo sapiens
<220> FEATURE:
<223> OTHER INFORMATION: Residues 180-188 of the TADG-15 protein

<400> SEQUENCE: 71

Met Leu Pro Pro Arg Ala Arg Ser Leu
                 5

<210> SEQ ID NO 72
<211> LENGTH: 9
<212> TYPE: PRT
<213> ORGANISM: Homo sapiens
<220> FEATURE:
<223> OTHER INFORMATION: Residues 217-225 of the TADG-15 protein

<400> SEQUENCE: 72

Gly Leu His Ala Arg Gly Val Glu Leu
                 5

<210> SEQ ID NO 73
<211> LENGTH: 9
<212> TYPE: PRT
<213> ORGANISM: Homo sapiens
<220> FEATURE:
<223> OTHER INFORMATION: Residues 173-181 of the TADG-15 protein

<400> SEQUENCE: 73

Met Ala Glu Glu Arg Val Val Met Leu
                 5

<210> SEQ ID NO 74
<211> LENGTH: 9
<212> TYPE: PRT
<213> ORGANISM: Homo sapiens
<220> FEATURE:
<223> OTHER INFORMATION: Residues 267-275 of the TADG-15 protein

<400> SEQUENCE: 74

Ser Cys Asp Glu Arg Gly Ser Asp Leu
                 5

<210> SEQ ID NO 75
<211> LENGTH: 9
<212> TYPE: PRT
<213> ORGANISM: Homo sapiens
<220> FEATURE:
<223> OTHER INFORMATION: Residues 567-575 of the TADG-15 protein

<400> SEQUENCE: 75

Cys Thr Lys His Thr Tyr Arg Cys Leu
                 5
```

```
<210> SEQ ID NO 76
<211> LENGTH: 9
<212> TYPE: PRT
<213> ORGANISM: Homo sapiens
<220> FEATURE:
<223> OTHER INFORMATION: Residues 724-732 of the TADG-15 protein

<400> SEQUENCE: 76

Ser Ser Met Val Arg Pro Ile Cys Leu
                 5

<210> SEQ ID NO 77
<211> LENGTH: 9
<212> TYPE: PRT
<213> ORGANISM: Homo sapiens
<220> FEATURE:
<223> OTHER INFORMATION: Residues 409-417 of the TADG-15 protein

<400> SEQUENCE: 77

Tyr Cys Gly Glu Arg Ser Gln Phe Val
                 5

<210> SEQ ID NO 78
<211> LENGTH: 9
<212> TYPE: PRT
<213> ORGANISM: Homo sapiens
<220> FEATURE:
<223> OTHER INFORMATION: Residues 495-503 of the TADG-15 protein

<400> SEQUENCE: 78

Thr Cys Lys Asn Lys Phe Cys Lys Pro
                 5

<210> SEQ ID NO 79
<211> LENGTH: 9
<212> TYPE: PRT
<213> ORGANISM: Homo sapiens
<220> FEATURE:
<223> OTHER INFORMATION: Residues 427-435 of the TADG-15 protein

<400> SEQUENCE: 79

Val Arg Phe His Ser Asp Gln Ser Tyr
                 5

<210> SEQ ID NO 80
<211> LENGTH: 9
<212> TYPE: PRT
<213> ORGANISM: Homo sapiens
<220> FEATURE:
<223> OTHER INFORMATION: Residues 695-703 of the TADG-15 protein

<400> SEQUENCE: 80

Lys Arg Ile Ile Ser His Pro Phe Phe
                 5

<210> SEQ ID NO 81
<211> LENGTH: 9
<212> TYPE: PRT
<213> ORGANISM: Homo sapiens
<220> FEATURE:
<223> OTHER INFORMATION: Residues 664-672 of the TADG-15 protein

<400> SEQUENCE: 81

Phe Arg Tyr Ser Asp Pro Thr Gln Trp
                 5

<210> SEQ ID NO 82
```

```
<211> LENGTH: 9
<212> TYPE: PRT
<213> ORGANISM: Homo sapiens
<220> FEATURE:
<223> OTHER INFORMATION: Residues 220-228 of the TADG-15 protein

<400> SEQUENCE: 82

Ala Arg Gly Val Glu Leu Met Arg Phe
                 5

<210> SEQ ID NO 83
<211> LENGTH: 9
<212> TYPE: PRT
<213> ORGANISM: Homo sapiens
<220> FEATURE:
<223> OTHER INFORMATION: Residues 492-500 of the TADG-15 protein

<400> SEQUENCE: 83

His Gln Phe Thr Cys Lys Asn Lys Phe
                 5

<210> SEQ ID NO 84
<211> LENGTH: 9
<212> TYPE: PRT
<213> ORGANISM: Homo sapiens
<220> FEATURE:
<223> OTHER INFORMATION: Residues 53-61 of the TADG-15 protein

<400> SEQUENCE: 84

Gly Arg Trp Val Val Leu Ala Ala Val
                 5

<210> SEQ ID NO 85
<211> LENGTH: 9
<212> TYPE: PRT
<213> ORGANISM: Homo sapiens
<220> FEATURE:
<223> OTHER INFORMATION: Residues 248-256 of the TADG-15 protein

<400> SEQUENCE: 85

Leu Arg Gly Asp Ala Asp Ser Val Leu
                 5

<210> SEQ ID NO 86
<211> LENGTH: 9
<212> TYPE: PRT
<213> ORGANISM: Homo sapiens
<220> FEATURE:
<223> OTHER INFORMATION: Residues 572-580 of the TADG-15 protein

<400> SEQUENCE: 86

Tyr Arg Cys Leu Asn Gly Leu Cys Leu
                 5

<210> SEQ ID NO 87
<211> LENGTH: 9
<212> TYPE: PRT
<213> ORGANISM: Homo sapiens
<220> FEATURE:
<223> OTHER INFORMATION: Residues 692-700 of the TADG-15 protein

<400> SEQUENCE: 87

Arg Arg Leu Lys Arg Ile Ile Ser His
                 5

<210> SEQ ID NO 88
<211> LENGTH: 9
<212> TYPE: PRT
```

```
<213> ORGANISM: Homo sapiens
<220> FEATURE:
<223> OTHER INFORMATION: Residues 24-32 of the TADG-15 protein

<400> SEQUENCE: 88

Ser Arg His Glu Lys Val Asn Gly Leu
                 5

<210> SEQ ID NO 89
<211> LENGTH: 9
<212> TYPE: PRT
<213> ORGANISM: Homo sapiens
<220> FEATURE:
<223> OTHER INFORMATION: Residues 147-155 of the TADG-15 protein

<400> SEQUENCE: 89

Ser Glu Gly Ser Val Ile Ala Tyr Tyr
                 5

<210> SEQ ID NO 90
<211> LENGTH: 9
<212> TYPE: PRT
<213> ORGANISM: Homo sapiens
<220> FEATURE:
<223> OTHER INFORMATION: Residues 715-723 of the TADG-15 protein

<400> SEQUENCE: 90

Leu Glu Leu Glu Lys Pro Ala Glu Tyr
                 5

<210> SEQ ID NO 91
<211> LENGTH: 9
<212> TYPE: PRT
<213> ORGANISM: Homo sapiens
<220> FEATURE:
<223> OTHER INFORMATION: Residues 105-113 of the TADG-15 protein

<400> SEQUENCE: 91

Tyr Glu Asn Ser Asn Ser Thr Glu Phe
                 5

<210> SEQ ID NO 92
<211> LENGTH: 9
<212> TYPE: PRT
<213> ORGANISM: Homo sapiens
<220> FEATURE:
<223> OTHER INFORMATION: Residues 14-22 of the TADG-15 protein

<400> SEQUENCE: 92

Lys Asp Phe Gly Ala Gly Leu Lys Tyr
                 5

<210> SEQ ID NO 93
<211> LENGTH: 9
<212> TYPE: PRT
<213> ORGANISM: Homo sapiens
<220> FEATURE:
<223> OTHER INFORMATION: Residues 129-137 of the TADG-15 protein

<400> SEQUENCE: 93

Ser Gly Val Pro Phe Leu Gly Pro Tyr
                 5

<210> SEQ ID NO 94
<211> LENGTH: 9
<212> TYPE: PRT
<213> ORGANISM: Homo sapiens
<220> FEATURE:
```

-continued

```
<223> OTHER INFORMATION: Residues 436-444 of the TADG-15 protein

<400> SEQUENCE: 94

Thr Asp Thr Gly Phe Leu Ala Glu Tyr
                5

<210> SEQ ID NO 95
<211> LENGTH: 9
<212> TYPE: PRT
<213> ORGANISM: Homo sapiens
<220> FEATURE:
<223> OTHER INFORMATION: Residues 766-774 of the TADG-15 protein

<400> SEQUENCE: 95

Gly Glu Ile Arg Val Ile Asn Gln Thr
                5

<210> SEQ ID NO 96
<211> LENGTH: 9
<212> TYPE: PRT
<213> ORGANISM: Homo sapiens
<220> FEATURE:
<223> OTHER INFORMATION: Residues 402-410 of the TADG-15 protein

<400> SEQUENCE: 96

Val Glu Ile Asn Gly Glu Lys Tyr Cys
                5

<210> SEQ ID NO 97
<211> LENGTH: 9
<212> TYPE: PRT
<213> ORGANISM: Homo sapiens
<220> FEATURE:
<223> OTHER INFORMATION: Residues 482-490 of the TADG-15 protein

<400> SEQUENCE: 97

Asp Glu Leu Asn Cys Ser Cys Asp Ala
                5

<210> SEQ ID NO 98
<211> LENGTH: 9
<212> TYPE: PRT
<213> ORGANISM: Homo sapiens
<220> FEATURE:
<223> OTHER INFORMATION: Residues 82-90 of the TADG-15 protein

<400> SEQUENCE: 98

Arg Asp Val Arg Val Gln Lys Val Phe
                5
```

TADG-15: AN EXTRACELLULAR SERINE PROTEASE OVEREXPRESSED IN CARCINOMAS

CROSS-REFERENCE TO RELATED APPLICATION

This application is a divisional of U.S. Ser. No. 10/600,187, filed Jun. 20, 2003, now U.S. Pat. No. 7,291,462 which is a divisional of U.S. Ser. No. 09/654,600, filed Sep. 1, 2000, now U.S. Pat. No. 6,649,741, which is a divisional of U.S. Ser. No. 09/421,213, filed Oct. 20, 1999, now U.S. Pat. No. 7,022,821, which is a continuation-in-part of U.S. Ser. No. 09/027,337, filed Feb. 20, 1998, now U.S. Pat. No. 5,972,616 and thereby claim the benefit of priority under 35 USC §120.

BACKGROUND OF THE INVENTION

1. Field of the Invention

The present invention relates generally to the fields of cellular biology and the diagnosis of neoplastic disease. More specifically, the present invention relates to an extracellular serine protease, termed tumor antigen-derived gene 15 (TADG-15), which is overexpressed in carcinomas.

2. Description of the Related Art

Extracellular proteases have been directly associated with tumor growth, shedding of tumor cells and invasion of target organs. Individual classes of proteases are involved in, but not limited to, (a) digestion of stroma surrounding the initial tumor area, (b) digestion of the cellular adhesion molecules to allow dissociation of tumor cells; and (c) invasion of the basement membrane for metastatic growth and activation of both tumor growth factors and angiogenic factors.

In the process of cancer progression and invasion, proteases mediate specific proteolysis and contribute to the removal of extracellular matrix components surrounding tumor cells, the digestion of intercellular adhesion molecules to allow dissociation of malignant cells and the activation of many growth and angiogenic factors.[1-3] Depending on the nature of their catalytic domain, proteases are classified into four families: serine proteases, metalloproteases, aspartic proteases and cysteine proteases.[3] Among these proteases, the metalloproteases have been well studied in relation to tumor growth and progression, and they are known to be capable of degrading the extracellular matrix, thereby enhancing the invasive potential of malignant cells.[1,4,5] For serine proteases, previous studies have demonstrated an increased production of plasminogen activator in tumor cells and a positive correlation between plasminogen activator activity and aggressiveness of cancer.[6,7] Prostate specific antigen (a serine protease) has also been widely used as an indicator of abnormal prostate growth.[8] More recently, several other serine proteases have been reported, viz. hepsin and the stratum corneum chymotryptic enzyme (SCCE), which are overexpressed in ovarian cancer and which may contribute to malignant progression by increasing the extracellular lytic activity of these tumor cells.[9]

The prior art is deficient in the lack of effective means of screening to identify proteases overexpressed in carcinoma. The present invention fulfills this longstanding need and desire in the art.

SUMMARY OF THE INVENTION

The present invention discloses a screening program to identify proteases overexpressed in carcinoma by examining PCR products amplified using differential display in early stage tumors and metastatic tumors compared to that of normal tissues. The approach herein to identify candidate genes overexpressed in tumor cells has been to utilize the well conserved domains surrounding the triad of amino acids (His-Asp-Ser) prototypical of the catalytic domain of serine proteases. Herein, evidence is presented for a unique form of serine protease not previously described in the literature which is highly expressed in ovarian carcinomas. Through the screening approach using differential PCR amplification of normal, low malignant potential and overt carcinomas, a PCR product present only in carcinoma was subcloned and sequenced, and was found to have a catalytic domain which was consistent with the serine protease family. Reported herein is the complete cloning and sequencing of this transcript and evidence for its expression in ovarian tumor cells.

In one embodiment of the present invention, there is provided a DNA encoding a tumor antigen-derived gene (TADG-15) protein, selected from the following: (a) an isolated DNA which encodes a TADG-15 protein; (b) an isolated DNA which hybridizes under high stringency conditions to the isolated DNA of (a) above and which encodes a TADG-15 protein; and (c) an isolated DNA differing from the isolated DNAs of (a) and (b) above in codon sequence due to the degeneracy of the genetic code, and which encodes a TADG-15 protein. The embodiment further includes a vector comprising the TADG-15 DNA and regulatory elements necessary for expression of the DNA in a cell. Additionally embodied is a vector in which the TADG-15 DNA is positioned in reverse orientation relative to the regulatory elements such that TADG-15 antisense mRNA is produced.

In another embodiment of the present invention, there is provided an isolated and purified TADG-15 protein coded for by DNA selected from the following: (a) an isolated DNA which encodes a TADG-15 protein; (b) an isolated DNA which hybridizes under high stringency conditions to isolated DNA of (a) above and which encodes a TADG-15 protein; and (c) an isolated DNA differing from the isolated DNAs of (a) and (b) above in codon sequence due to the degeneracy of the genetic code, and which encodes a TADG-15 protein.

In yet another embodiment of the present invention, there is provided a method for detecting TADG-15 mRNA in a sample, comprising the steps of: (a) contacting a sample with a probe which is specific for TADG-15; and (b) detecting binding of the probe to TADG-15 mRNA in the sample. In still yet another embodiment of the present invention, there is provided a kit for detecting TADG-15 mRNA, comprising: an oligonucleotide probe specific for TADG-15. A label for detection is further embodied in the kit.

The present invention additionally embodies a method of detecting TADG-15 protein in a sample, comprising the steps of: (a) contacting a sample with an antibody which is specific for TADG-15 or a fragment thereof; and (b) detecting binding of the antibody to TADG-15 protein in the sample. Similarly, the present invention also embodies a kit for detecting TADG-15 protein, comprising: an antibody specific for TADG-15 protein or a fragment thereof. Means for detection of the antibody is further embodied in the kit.

In another embodiment, the present invention provides an antibody specific for the TADG-15 protein or a fragment thereof.

In yet another embodiment, the present invention provides a method of screening for compounds that inhibit TADG-15, comprising the steps of: (a) contacting a sample comprising TADG-15 protein with a compound; and (b) assaying for TADG-15 protease activity. Typically, a decrease in the TADG-15 protease activity in the presence of the compound relative to TADG-15 protease activity in the absence of the compound is indicative of a compound that inhibits TADG-15.

In still yet another embodiment of the present invention, there is provided a method of inhibiting expression of TADG-15 in a cell, comprising the step of: (a) introducing a vector into a cell, whereupon expression of the vector produces TADG-15 antisense mRNA in the cell which hybridizes to endogenous TADG-15 mRNA, thereby inhibiting expression of TADG-15 in the cell.

Further embodied by the present invention, there is provided a method of inhibiting a TADG-15 protein in a cell, comprising the step of: (a) introducing an antibody specific for a TADG-15 protein or a fragment thereof into a cell, whereupon binding of the antibody to the TADG-15 protein inhibits the TADG-15 protein.

In an embodiment of the present invention, there is provided a method of targeted therapy to an individual, comprising the step of: (a) administering a compound containing a targeting moiety and a therapeutic moiety to an individual, wherein the targeting moiety is specific for TADG-15.

In an embodiment of the present invention, there is provided a method of diagnosing cancer in an individual, comprising the steps of: (a) obtaining a biological sample from an individual; and (b) detecting TADG-15 in the sample, wherein the presence of TADG-15 in the sample is indicative of the presence of carcinoma in the individual and the absence of TADG-15 in the sample is indicative of the absence of carcinoma in the individual.

In another embodiment of the present invention, there is provided a method of vaccinating an individual against TADG-15, comprising the steps of: (a) inoculating an individual with a TADG-15 protein or fragment thereof that lacks TADG-15 protease activity, wherein the inoculation with the TADG-15 protein or fragment thereof elicits an immune response in the individual, thereby vaccinating the individual against TADG-15.

In an embodiment of the present invention, there is provided a method of producing immune-activated cells directed toward TADG-15, comprising the steps of: exposing dendritic cells to a TADG-15 protein or fragment thereof that lacks TADG-15 protease activity, wherein the exposure to said TADG-15 protein or fragment thereof activates the dendritic cells, thereby producing immune-activated cells directed toward TADG-15.

In another embodiment of the present invention, there is provided an immunogenic composition, comprising an immunogenic fragment of a TADG-15 protein and an appropriate adjuvant.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIGS. 1A-1B show a comparison of the serine protease catalytic domain of TADG-15 with Hepsin (Heps, SEQ ID No. 3), SCCE (SEQ ID No. 4), Trypsin (Try, SEQ ID No. 5), Chymotrypsin (Chymb, SEQ ID No. 6), Factor 7 (Fac7, SEQ ID No. 7) and Tissue plasminogen activator (Tpa, SEQ ID No. 8). The asterisks indicate conserved amino acids of catalytic triad.

FIGS. 2A-2D show the nucleotide sequence of the TADG-15 cDNA and the derived amino acid sequence of the TADG-15 protein. The putative start codon is located at nucleotides 23-25. The potential transmembrane sequence is underlined. Possible N-linked glycosylation sites are indicated by a broken line. The asterisks indicate conserved cysteine residues of CUB domain. The SDE-motifs of the LDL receptor ligand binding repeat-like domain are boxed. The arrow shows the arginine-valine bond cleaved upon activation. The conserved amino acids of the catalytic triad; histidine, aspartic acid and serine residues are circled.

FIG. 6A shows quantitative PCR analysis of TADG-15 expression. Expression levels of TADG-15 relative to β-tubulin are significantly elevated in all LMP tumors and carcinomas compared to that of normal ovaries. m; mucinous, s; serous.

Figure 10A:
FIG. 10 shows that immunohistochemical staining of normal ovarian epithelium (FIG. 10A) with a polyclonal antibody to a TADG-15 protease peptide shows no staining of the stroma or epithelium. However, antibody staining of carcinomas confirms the presence of TADG-15 expression in the cytoplasm of a serous low malignant potential tumor (FIG. 10B); a mucinous low malignant potential tumor (FIG. 10C)
Figure 10B:
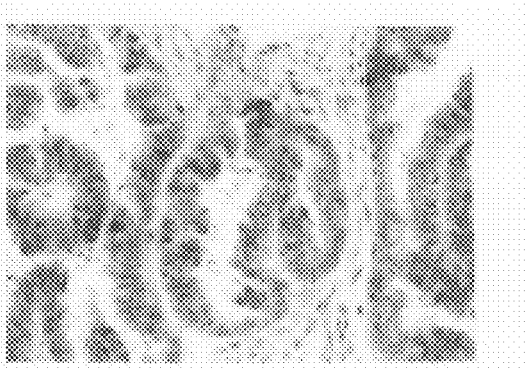
Figure 10C:
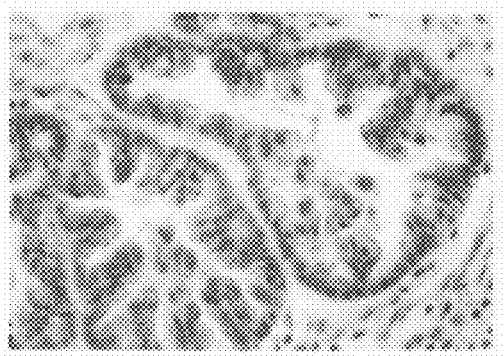
Figure 10D:
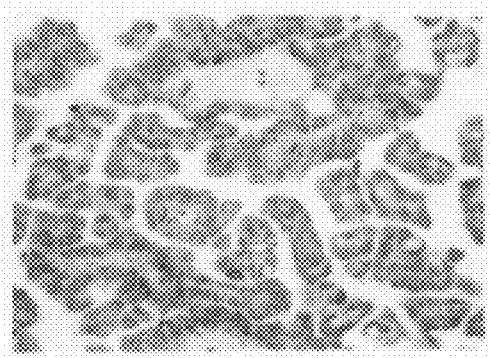
Figure 10E:
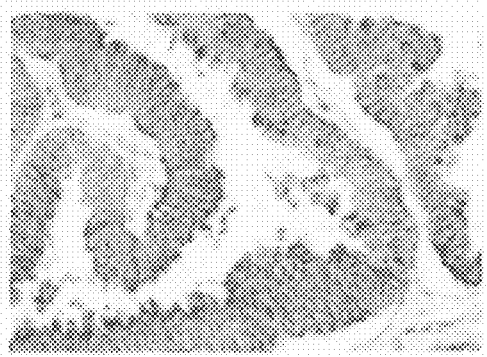

a serous carcinoma (FIG. 10D); and its presence in both the cytoplasm and cell surface of an endometrioid carcinoma (FIG. 10E).

FIGS. 11A-11B show an alignment of the human TADG15 protein sequence with that of mouse epithin which demonstrates that the proteins are 84% similar and 81% identical over 843 amino acids. Residues that are identical between the two proteins are indicated by a "-", while the "*" symbol represents the TADG15 translation termination. The most significant difference between these two proteins lies in the carboxy-termini, which for epithin, includes 47 amino acids that are not present in TADG15.

Figure 12A:
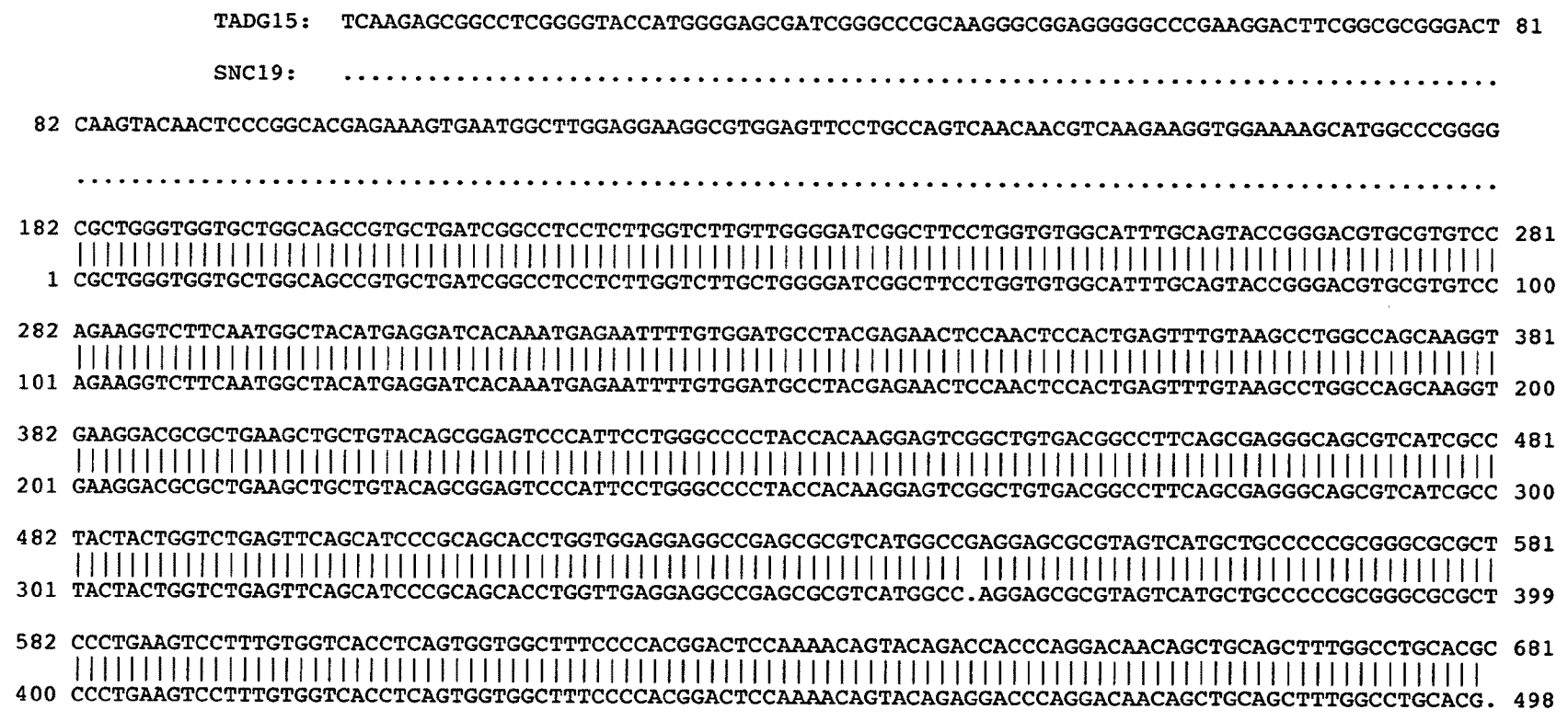
Figure 12B:
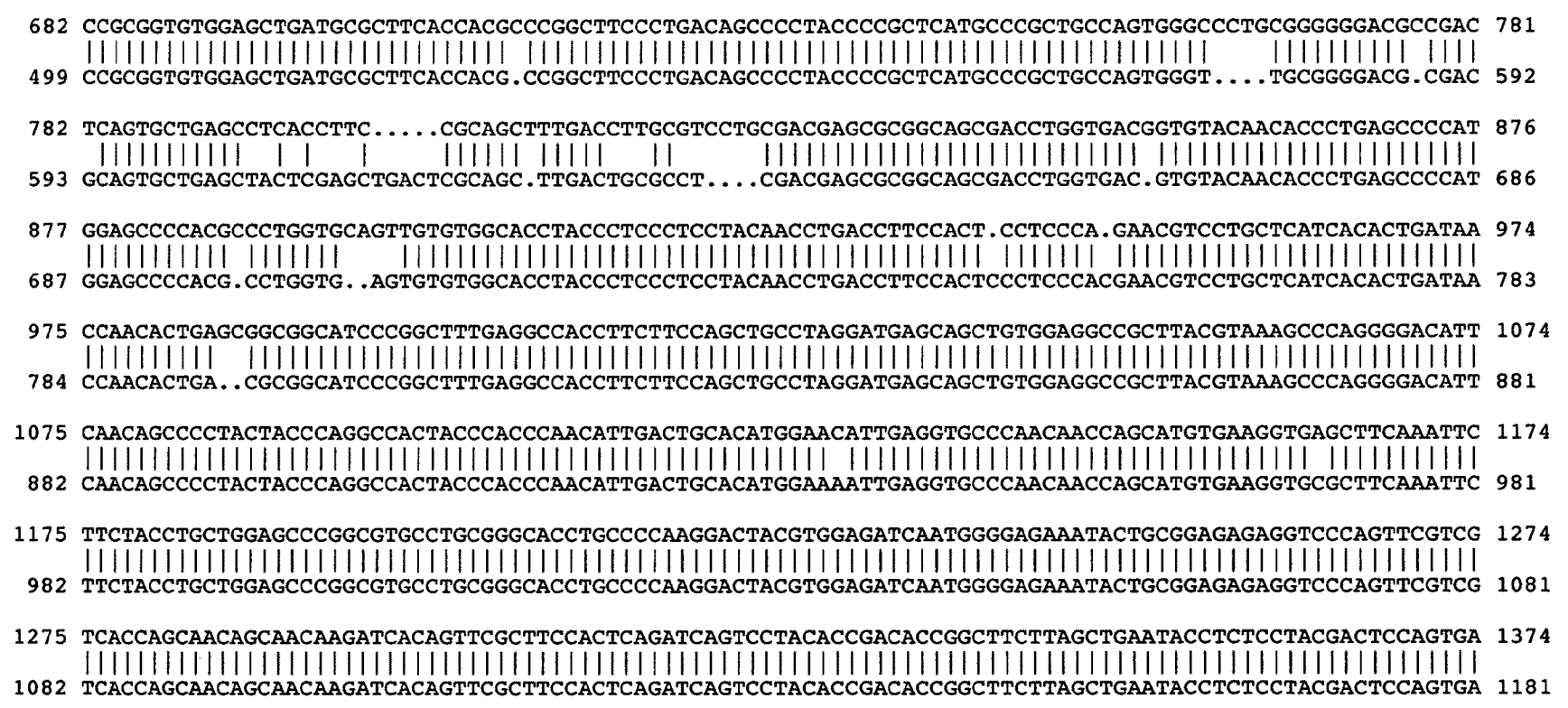
Figure 12C:
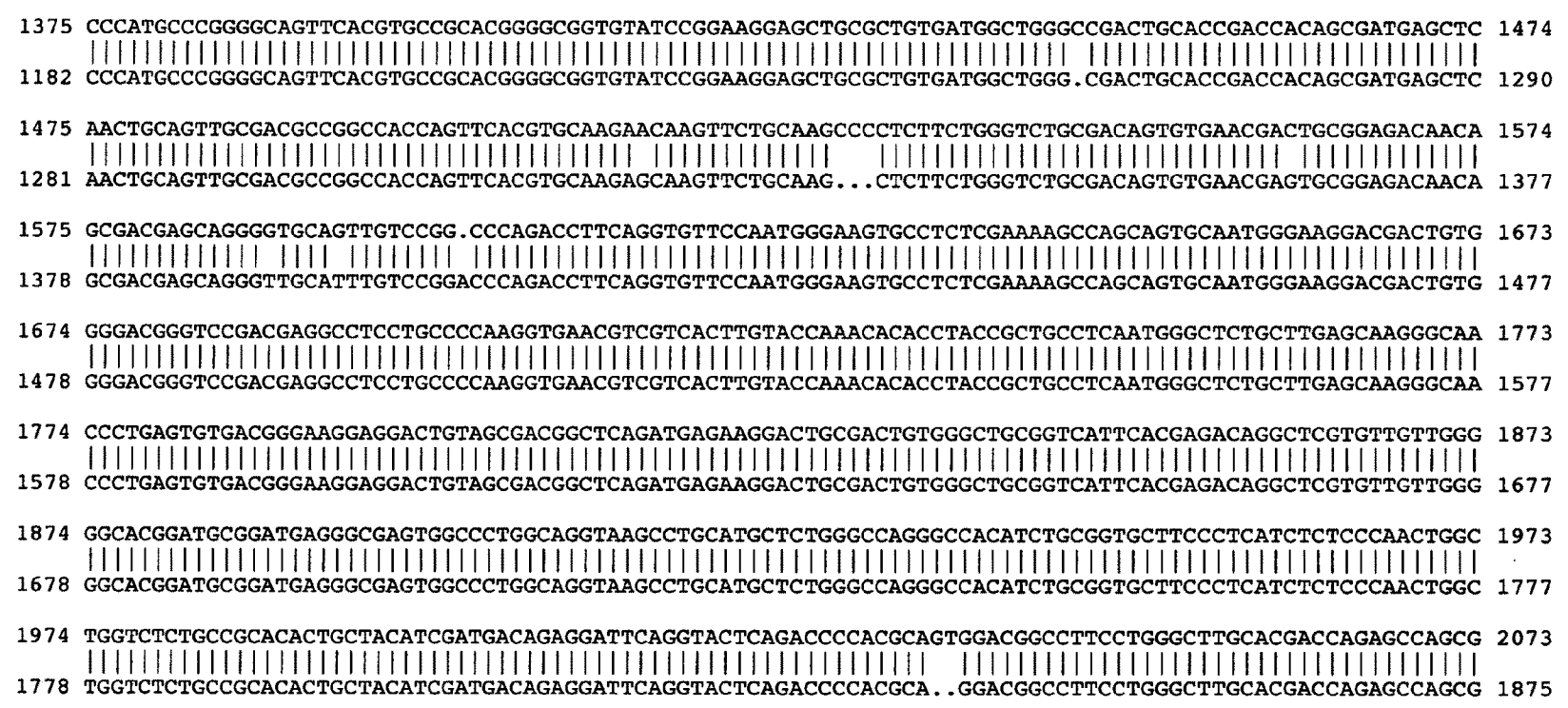
Figure 12D:
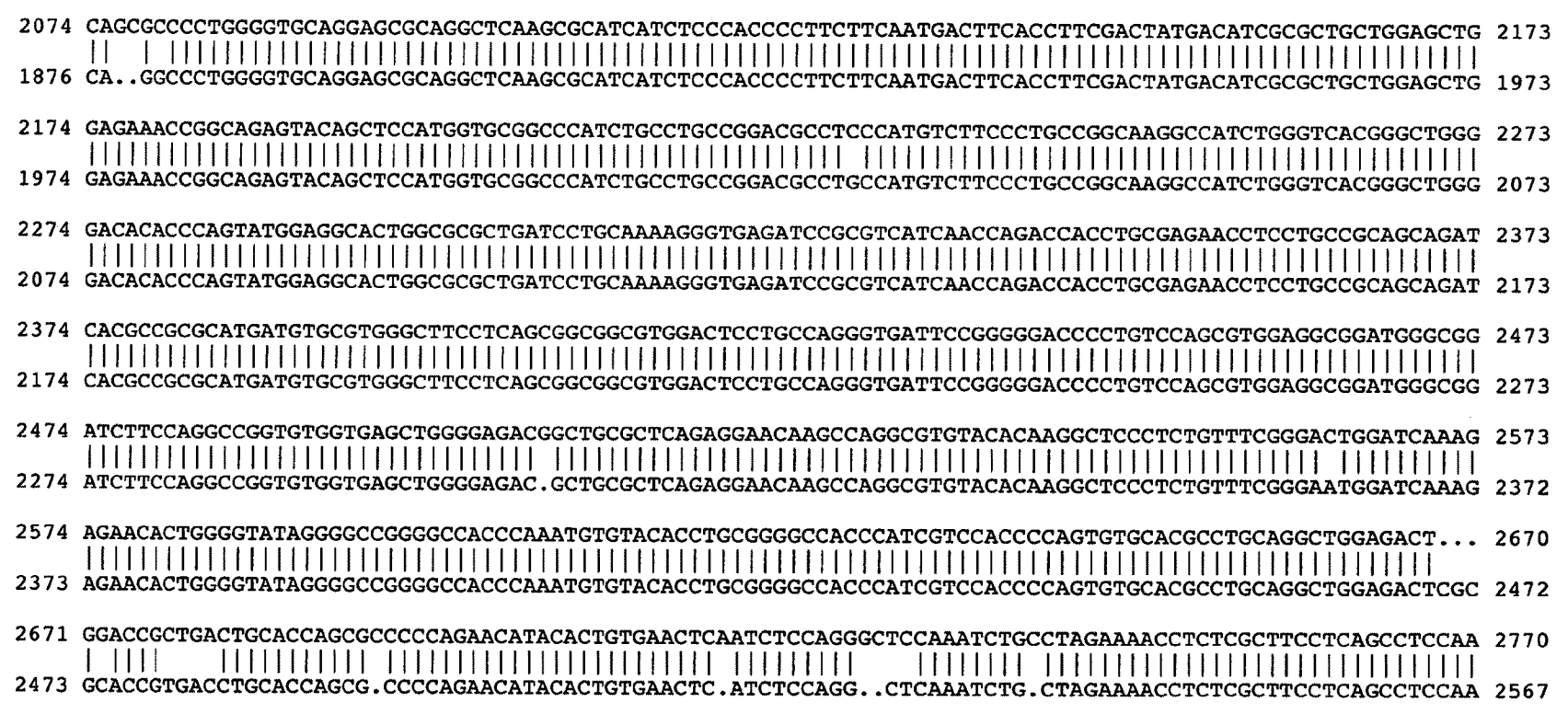

FIGS. 12A-12E show a nucleotide sequence comparison between TADG-15 and human SNC-19 (GeneBank Accession No. #U20428).

DETAILED DESCRIPTION OF THE INVENTION

Proteases have been implicated in the extracellular modulation required for tumor growth and invasion. In an effort to categorize those proteases contributing to ovarian carcinoma progression, redundant primers directed towards conserved amino acid domains surrounding the catalytic triad of His, Asp and Ser were utilized to amplify serine proteases differentially expressed in carcinomas. Using this method, a serine protease named TADG-15 (tumor antigen-derived gene 15) has been identified that is overexpressed in ovarian tumors. TADG-15 appears to be a transmembrane multidomain serine protease. TADG-15 is highly overexpressed in ovarian tumors based on PCR, Northern blot and immunolocalization.

The TADG-15 cDNA is 3147 base pairs long (SEQ ID No. 1) encoding for a 855 amino acid protein (SEQ ID No. 2). The availability of the TADG-15 gene provides numerous utilities. For example, the TADG-15 gene can be used as a diagnostic or therapeutic target in ovarian and other carcinomas, including breast, prostate, lung and colon.

The present invention is directed to DNA encoding a tumor antigen-derived gene (TADG-15) protein, selected from the following: (a) an isolated DNA which encodes a TADG-15 protein; (b) an isolated DNA which hybridizes under high stringency conditions to the isolated DNA of (a) above and which encodes a TADG-15 protein; and (c) an isolated DNA differing from the isolated DNAs of (a) and (b) above in codon sequence due to the degeneracy of the genetic code, and which encodes a TADG-15 protein. It is preferred that the DNA has the sequence shown in SEQ ID No. 1 and the TADG-15 protein has the amino acid sequence shown in SEQ ID No. 2.

The present invention is directed toward a vector comprising the TADG-15 DNA and regulatory elements necessary for expression of the DNA in a cell, or a vector in which the TADG-15 DNA is positioned in reverse orientation relative to the regulatory elements such that TADG-15 antisense mRNA is produced. Generally, the DNA encodes a TADG-15 protein having the amino acid sequence shown in SEQ ID No. 2. The invention is also directed toward host cells transfected with either of the above-described vector(s). Representative host cells are bacterial cells, mammalian cells, plant cells and insect cells. Preferably, the bacterial cell is E. coli.

The present invention is directed toward an isolated and purified TADG-15 protein coded for by DNA selected from the following: (a) an isolated DNA which encodes a TADG-15 protein; (b) an isolated DNA which hybridizes under high stringency conditions to isolated DNA of (a) above and which encodes a TADG-15 protein; and (c) an isolated DNA differing from the isolated DNAs of (a) and (b) above in codon sequence due to the degeneracy of the genetic code, and which encodes a TADG-15 protein. Preferably, the protein has the amino acid sequence shown in SEQ ID No. 2.

The present invention is directed toward a method for detecting TADG-15 mRNA in a sample, comprising the steps of: (a) contacting a sample with a probe which is specific for TADG-15; and (b) detecting binding of the probe to TADG-15 mRNA in the sample. The present invention is also directed toward a method of detecting TADG-15 protein in a sample, comprising the steps of: (a) contacting a sample with an antibody which is specific for TADG-15 or a fragment thereof; and (b) detecting binding of the antibody to TADG-15 protein in the sample. Generally, the sample is a biological sample; preferably, the biological sample is from an individual; and typically, the individual is suspected of having cancer.

The present invention is directed toward a kit for detecting TADG-15 mRNA, comprising: an oligonucleotide probe, wherein the probe is specific for TADG-15. The kit may further comprise: a label with which to label the probe; and means for detecting the label. The present invention is additionally directed toward a kit for detecting TADG-15 protein, comprising: an antibody which is specific for TADG-15 protein or a fragment thereof. The kit may further comprise: means to detect the antibody.

The present invention is directed toward a antibody which is specific for TADG-15 protein or a fragment thereof.

The present invention is directed toward a method of screening for compounds that inhibit TADG-15, comprising the steps of: (a) contacting a sample containing TADG-15 protein with a compound; and (b) assaying for TADG-15 protease activity. Typically, a decrease in the TADG-15 protease activity in the presence of the compound relative to TADG-15 protease activity in the absence of the compound is indicative of a compound that inhibits TADG-15.

The present invention is directed toward a method of inhibiting expression of TADG-15 in a cell, comprising the step of: (a) introducing a vector expressing TADG-15 antisense mRNA into a cell, which hybridizes to endogenous TADG-15 mRNA, thereby inhibiting expression of TADG-15 in the cell. Generally, the inhibition of TADG-15 expression is for treating cancer.

The present invention is directed toward a method of inhibiting a TADG-15 protein in a cell, comprising the step of: (a) introducing an antibody specific for a TADG-15 protein or a fragment thereof into a cell, which inhibits the TADG-15 protein. Generally, the inhibition of the TADG-15 protein is for treating cancer.

The present invention is directed toward a method of targeted therapy to an individual, comprising the step of: (a) administering a compound having a targeting moiety and a therapeutic moiety to an individual, wherein the targeting moiety is specific for TADG-15. Representative targeting moiety are an antibody specific for TADG-15 and a ligand or ligand binding domain (e.g., CUB, LDLR, protease and extracellular) that binds TADG-15. Likewise, a representative therapeutic moiety is a radioisotope, a toxin, a chemotherapeutic agent and immune stimulants. Typically, the above-described method is useful when the individual suffers from ovarian cancer, breast cancer or cancers of the prostate, lung, colon and cervix.

The present invention is directed toward a method of diagnosing cancer in an individual, comprising the steps of: (a) obtaining a biological sample from an individual; and (b) detecting TADG-15 in the sample. Generally, the presence of TADG-15 in the sample is indicative of the presence of carcinoma in the individual, and the absence of TADG-15 in the sample is indicative of the absence of carcinoma in the individual. Generally, the biological sample is blood, ascites fluid, urine, tears, saliva or interstitial fluid. Typical means of detecting TADG-15 are by Northern blot, Western blot, PCR, dot blot, ELIZA, radioimmunoassay, DNA chips or tumor cell labeling. This method may be useful in diagnosing cancers such as ovarian, breast and other cancers in which TADG-15 is overexpressed, such as lung, prostate and colon cancers.

The present invention is also directed to an antisense oligonucleotide having the nucleotide sequence complementary to a TADG-15 mRNA sequence. The present invention is also directed to a composition comprising such an antisense oligonucleotide according and a physiologically acceptable carrier therefore.

The present invention is also directed to a method of treating a neoplastic state in an individual syndrome in an individual in need of such treatment, comprising the step of administering to said individual an effective dose of an antisense oligonucleotide of. Preferably, the neoplastic state is selected from the group consisting of from ovarian cancer, breast cancer, lung cancer, prostate cancer, colon cancer and other cancers in which TADG-15 is overexpressed. For such therapy, the oligonucleotides alone or in combination with other anti-neoplastic agents can be formulated for a variety of modes of administration, including systemic, topical or localized administration. Techniques and formulations generally can be found in *Remington's Pharmaceutical Sciences*, Mack Publishing Co., Easton, Pa. The oligonucleotide active ingredient is generally combined with a pharamceutically acceptable carrier such as a diluent or excipient which can include fillers, extenders, binders, wetting agents, disintergrants, surface active agents or lubricants, depending on the nature of the mode of administration and dosage forms. Typical dosage forms include tablets, powders, liquid preparations including suspensions, emulsions, and solutions, granules, capsules and suppositories, as well as liquid preparations for injections, including liposome preparations.

For systemic administration, injection is preferred, including intramuscular, intravenous, intraperitoneal and subcutaneous. For injection, the oligonucleotides of the invention are formulated in liquid solutions, preferably in physiologically compatible buffers. In addition, the oligonucleotides can be formulated in solid form and redissolved or suspended immediately prior to use. Lyophilized forms are also included. Dosages that can be used for systemic administration preferably range from about 0.01 mg/kg to 50 mg/kg administered once or twice per day. However, different dosing schedules can be utilized depending on (1) the potency of an individual oligonucleotide at inhibiting the activity of its target DNA, (2) the severity or extent of the pathological disease state, or (3) the pharmacokinetic behavior of a given oligonucleotide.

The present invention is directed toward a method of vaccinating an individual against TADG-15 overexpression, comprising the steps of: (a) inoculating an individual with a TADG-15 protein or fragment thereof which lacks TADG-15 protease activity. The inoculation with the TADG-15 protein or fragment thereof elicits an immune response in the individual, thereby vaccinating the individual against TADG-15. The vaccination with TADG-15 described herein is intended for an individual who has cancer, is suspected of having cancer or is at risk of getting cancer. Generally, the TADG-15 fragment useful for vaccinating an individual are 9-residue fragments up to 20-residue fragments, with preferred 9-residue fragments shown in SEQ ID Nos. 2, 19, 20, 21, 29, 39, 49, 50, 59, 79, 80, 81, 82, 83, 84, 89 and 90.

The present invention is directed toward a method of producing immune-activated cells directed toward TADG-15, comprising the steps of: exposing dendritic cells to a TADG-15 protein or fragment thereof that lacks TADG-15 protease activity, wherein exposure to the TADG-15 protein or fragment thereof activates the dendritic cells, thereby producing immune-activated cells directed toward TADG-15. Representative immune-activated cells are B-cells, T-cells and dendrites. Generally, the TADG-15 fragment is a 9-residue fragment up to a 20-residue fragment, with preferable 9-residue fragments shown in SEQ ID Nos. 2, 19, 20, 21, 29, 39, 49, 50, 59, 79, 80, 81, 82, 83, 84, 89 and 90. Preferably, the dendritic cells are isolated from an individual prior to exposure, and the activated dendritic cells reintroduced into the individual subsequent to exposure. Typically, the individual for which this method may apply has cancer, is suspected of having cancer or is at risk of getting cancer.

The present invention is directed toward an immunogenic composition, comprising an immunogenic fragment of a TADG-15 protein and an appropriate adjuvant. Generally, the fragment is a 9-residue fragment up to a 20-residue fragment, with preferred 9-residue fragments shown in SEQ ID Nos. 2, 19, 20, 21, 29, 39, 49, 50, 59, 79, 80, 81, 82, 83, 84, 89 and 90.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. 1985); "Transcription and Translation" (B. D. Hames & S. J. Higgins eds. 1984); "Animal Cell Culture" (R. I. Freshney, ed. 1986); "Immobilized Cells And Enzymes" (IRL Press, 1986); B. Perbal, "A Practical Guide To Molecular Cloning" (1984). Therefore, if appearing herein, the following terms shall have the definitions set out below.

As used herein, the term "cDNA" shall refer to the DNA copy of the mRNA transcript of a gene.

As used herein, the term "derived amino acid sequence" shall mean the amino acid sequence determined by reading the triplet sequence of nucleotide bases in the cDNA.

As used herein the term "screening a library" shall refer to the process of using a labeled probe to check whether, under the appropriate conditions, there is a sequence complementary to the probe present in a particular DNA library. In addition, "screening a library" could be performed by PCR.

As used herein, the term "PCR" refers to the polymerase chain reaction that is the subject of U.S. Pat. Nos. 4,683,195 and 4,683,202 to Mullis, as well as other improvements now known in the art.

The amino acid described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are used as in customary in the art.

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment. A "vector" may further be defined as a replicable nucleic acid construct, e.g., a plasmid or viral nucleic acid.

A "DNA molecule" refers to the polymeric form of deoxyribonucleotides (adenine, guanine, thymine, or cytosine) in its either single-stranded form or as a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. The structure is discussed herein according to the normal convention of giving only the sequence in the 5' to 3' direction along the nontranscribed strand of DNA (i.e., the strand having a sequence homologous to the mRNA).

An expression vector is a replicable construct in which a nucleic acid sequence encoding a polypeptide is operably linked to suitable control sequences capable of effecting expression of the polypeptide in a cell. The need for such control sequences will vary depending upon the cell selected and the transformation method chosen. Generally, control sequences include a transcriptional promoter and/or enhancer, suitable mRNA ribosomal binding sites, and sequences which control the termination of transcription and translation. Methods which are well known to those skilled in the art can be used to construct expression vectors containing appropriate transcriptional and translational control signals. See, for example, techniques described in Sambrook et al., 1989, *Molecular Cloning: A Laboratory Manual* (2nd Ed.), Cold Spring Harbor Press, N.Y. A gene and its transcription control sequences are defined as being "operably linked" if the transcription control sequences effectively control transcription of the gene. Vectors of the invention include, but are not limited to, plasmid vectors and viral vectors. Preferred viral vectors of the invention are those derived from retroviruses, adenovirus, adeno-associated virus, SV40 virus, or herpes viruses. In general, expression vectors contain promoter sequences which facilitate the efficient transcription of the inserted DNA fragment and are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters typically contain Shine-Dalgarno ribosome-binding sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included near the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

As used herein, the terms "restriction endonucleases" and "restriction enzymes" refer to enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. Proteins can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$. Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, b-glucuronidase, b-D-glucosidase, b-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

A particular assay system developed and utilized in the art is known as a receptor assay. In a receptor assay, the material to be assayed is appropriately labeled and then certain cellular test colonies are inoculated with a quantity of both the label after which binding studies are conducted to determine the extent to which the labeled material binds to the cell receptors. In this way, differences in affinity between materials can be ascertained.

An assay useful in the art is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784.

As used herein, the term "host" is meant to include not only prokaryotes but also eukaryotes such as yeast, plant and animal cells. A recombinant DNA molecule or gene which encodes a human TADG-15 protein of the present invention can be used to transform a host using any of the techniques commonly known to those of ordinary skill in the art. Especially preferred is the use of a vector containing coding sequences for the gene which encodes a human TADG-15 protein of the present invention for purposes of prokaryote transformation. Prokaryotic hosts may include *E. coli, S. tymphimurium, Serratia marcescens* and *Bacillus subtilis*. Eukaryotic hosts include yeasts such as *Pichia pastoris*, mammalian cells and insect cells.

Figure 3:
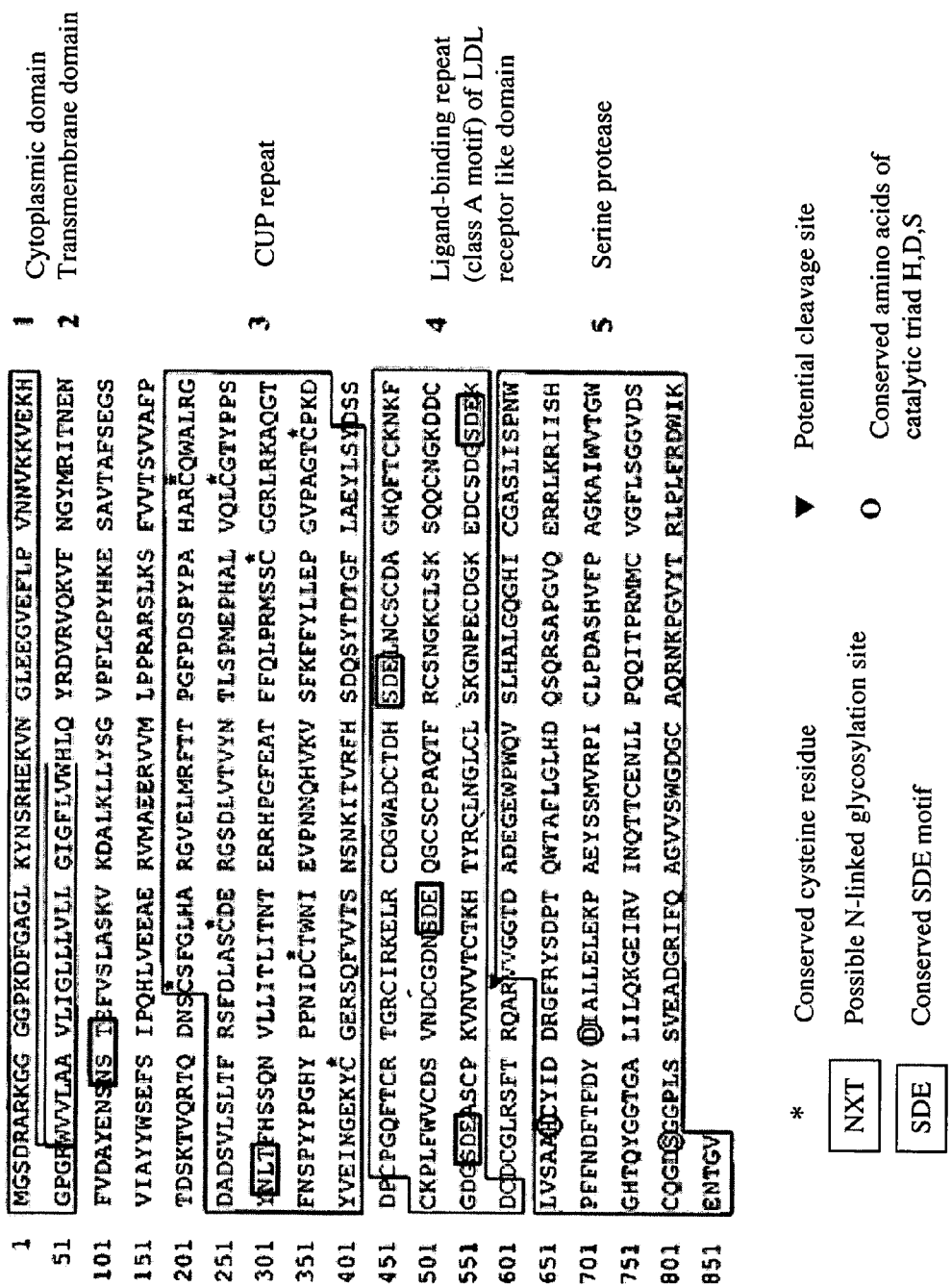
FIG. 3 shows the amino acid sequence of the TADG-15 protease, including functional sites and domains.
Figure 4:
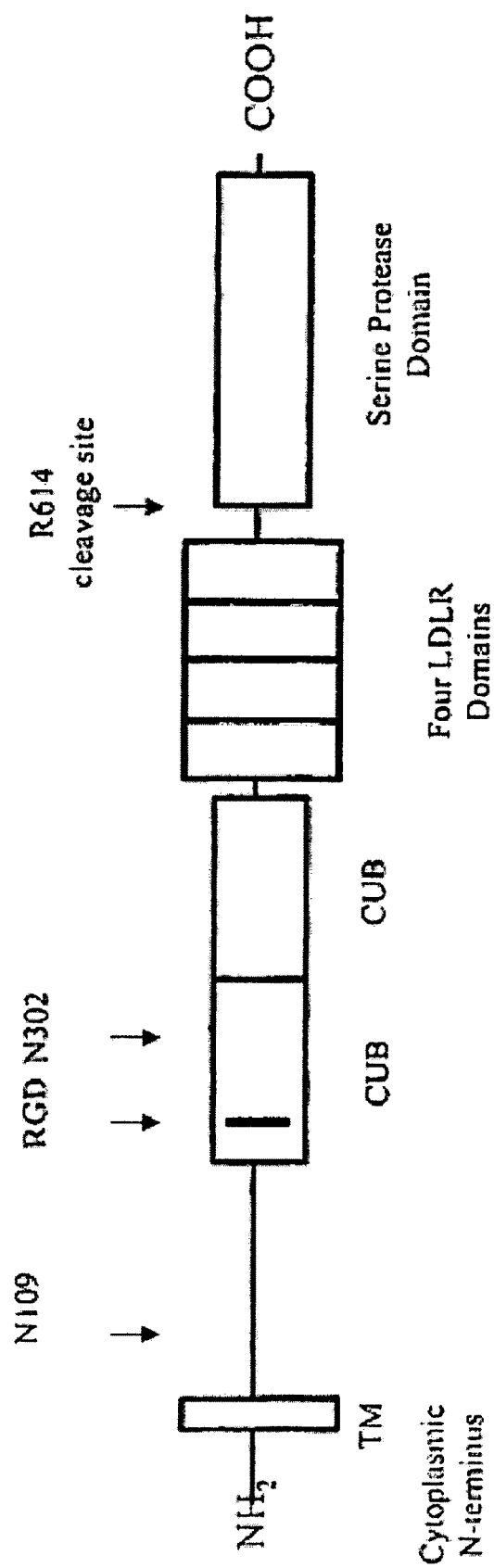
FIG. 4 shows a diagram of the TADG-15 protein. 1; cytoplasmic domain, (aa #1-54), 2; transmembrane domain (aa #55-57), 3; extracellular domain (aa #78-213), 4-5; CUB repeat (aa #214-447), 6-9; LDL receptor ligand binding repeat (class A motif) like domain (aa #453-602), 10; serine protease (aa #615-855).

The invention includes a substantially pure DNA encoding a TADG-15 protein, a DNA strand which will hybridize at high stringency to a probe containing a sequence of at least 15 consecutive nucleotides of (SEQ ID No. 1). The protein encoded by the DNA of this invention may share at least 80% sequence identity (preferably 85%, more preferably 90%, and most preferably 95%) with the amino acids listed in FIGS. 3 and 4 (SEQ ID No. 2). More preferably, the DNA includes the coding sequence of the nucleotides of FIG. 2 (SEQ ID No. 1), or a degenerate variant of such a sequence. This invention also includes a substantially pure DNA containing a sequence of at least 15 consecutive nucleotides (preferably 20, more preferably 30, even more preferably 50, and most preferably all) of the region from nucleotides 1 to 3147 of the nucleotides shown in FIGS. 2A-2D (SEQ ID No. 1).

By "substantially pure DNA" is meant DNA that is not part of a milieu in which the DNA naturally occurs, by virtue of separation (partial or total purification) of some or all of the molecules of that milieu, or by virtue of alteration of sequences that flank the claimed DNA. The term therefore includes, for example, a recombinant DNA which is incorporated into a vector, into an autonomously replicating plasmid or virus, or into the genomic DNA of a prokaryote or eukaryote; or which exists as a separate molecule (e.g., a cDNA or a genomic or cDNA fragment produced by polymerase chain reaction (PCR) or restriction endonuclease digestion) independent of other sequences. It also includes a recombinant DNA which is part of a hybrid gene encoding additional polypeptide sequence, e.g., a fusion protein. Also included is a recombinant DNA which includes a portion of the nucleotides listed in FIGS. 2A-2D (SEQ ID No. 1) and which encodes an alternative splice variant of TADG-15.

By a "substantially pure protein" is meant a protein which has been separated from at least some of those components which naturally accompany it. Typically, the protein is substantially pure when it is at least 60% (by weight) free from the proteins and other naturally-occurring organic molecules with which it is naturally associated in vivo. Preferably, the purity of the preparation (by weight) is at least 75%, more preferably at least 90%, and most preferably at least 99%. A substantially pure TADG-15 protein may be obtained, for example, by extraction from a natural source; by expression of a recombinant nucleic acid encoding a TADG-15 polypeptide; or by chemically synthesizing the protein. Purity can be measured by any appropriate method, e.g., column chromatography, such as immunoaffinity chromatography using an antibody specific for TADG-15, polyacrylamide gel electrophoresis, or HPLC analysis. A protein is substantially free of naturally associated components when it is separated from at least some of those contaminants which accompany it in its natural state. Thus, a protein which is chemically synthesized or produced in a cellular system different from the cell from which it naturally originates will be, by definition, substantially free from its naturally associated components. Accordingly, substantially pure proteins include eukaryotic proteins synthesized in E. coli, other prokaryotes, or any other organism in which they do not naturally occur.

The term "oligonucleotide", as used herein, is defined as a molecule comprised of two or more ribonucleotides, preferably more than three. Its exact size will depend upon many factors, which, in turn, depend upon the ultimate function and use of the oligonucleotide. The term "primer", as used herein, refers to an oligonucleotide, whether occurring naturally (as in a purified restriction digest) or produced synthetically, and which is capable of initiating synthesis of a strand complementary to a nucleic acid when placed under appropriate conditions, i.e., in the presence of nucleotides and an inducing agent, such as a DNA polymerase, and at a suitable temperature and pH. The primer may be either single-stranded or double-stranded and must be sufficiently long to prime the synthesis of the desired extension product in the presence of the inducing agent. The exact length of the primer will depend upon many factors, including temperature, sequence and/or homology of primer and the method used. For example, in diagnostic applications, the oligonucleotide primer typically contains 15-25 or more nucleotides, depending upon the complexity of the target sequence, although it may contain fewer nucleotides.

The primers herein are selected to be "substantially" complementary to particular target DNA sequences. This means that the primers must be sufficiently complementary to hybridize with their respective strands. Therefore, the primer sequence need not reflect the exact sequence of the template. For example, a non-complementary nucleotide fragment (i.e., containing a restriction site) may be attached to the 5' end of the primer, with the remainder of the primer sequence being complementary to the strand. Alternatively, non-complementary bases or longer sequences can be interspersed into the primer, provided that the primer sequence has sufficient complementary with the sequence to hybridize therewith and form the template for synthesis of the extension product.

The probe to which the DNA of the invention hybridizes preferably consists of a sequence of at least 20 consecutive nucleotides, more preferably 40 nucleotides, even more preferably 50 nucleotides, and most preferably 100 nucleotides or more (up to 100%) of the coding sequence of the nucleotides listed in FIGS. 2A-2D (SEQ ID No. 1) or the complement thereof. Such a probe is useful for detecting expression of TADG-15 in a cell by a method including the steps of (a) contacting mRNA obtained from the cell with a labeled TADG-15 hybridization probe; and (b) detecting hybridization of the probe with the mRNA.

By "high stringency" is meant DNA hybridization and wash conditions characterized by high temperature and low salt concentration, e.g., wash conditions of 65° C. at a salt concentration of approximately 0.1×SSC, or the functional equivalent thereof. For example, high stringency conditions may include hybridization at about 42° C. in the presence of about 50% formamide; a first wash at about 65° C. with about 2×SSC containing 1% SDS; followed by a second wash at about 65° C. with about 0.1×SSC.

The DNA may have at least about 70% sequence identity to the coding sequence of the nucleotides listed in FIGS. 2A-2D (SEQ ID No. 1), preferably at least 75% (e.g., at least 80%); and most preferably at least 90%. The identity between two sequences is a direct function of the number of matching or identical positions. When a position in both of the two sequences is occupied by the same monomeric subunit, e.g., if a given position is occupied by an adenine in each of two DNA molecules, then they are identical at that position. For example, if 7 positions in a sequence 10 nucleotides in length are identical to the corresponding positions in a second 10-nucleotide sequence, then the two sequences have 70% sequence identity. The length of comparison sequences will generally be at least 50 nucleotides, preferably at least 60 nucleotides, more preferably at least 75 nucleotides, and most preferably 100 nucleotides. Sequence identity is typically measured using sequence analysis software (e.g., Sequence Analysis Software Package of the Genetics Computer Group (GCG), University of Wisconsin Biotechnology Center, 1710 University Avenue, Madison, Wis. 53705).

The present invention comprises a vector comprising a DNA sequence which encodes a human TADG-15 protein, wherein said vector is capable of replication in a host, and comprises, in operable linkage: a) an origin of replication; b) a promoter; and c) a DNA sequence coding for said TADG-15 protein. Preferably, the vector of the present invention contains a portion of the DNA sequence shown in SEQ ID No. 1. Vectors may be used to amplify and/or express nucleic acid encoding a TADG-15 protein or fragment thereof.

In addition to substantially full-length proteins, the invention also includes fragments (e.g., antigenic fragments) of the TADG-15 protein (SEQ ID No. 2). As used herein, "fragment," as applied to a polypeptide, will ordinarily be at least 6 residues, more typically at least 9-12 residues, and preferably at least 13-20 residues in length, but less than the entire, intact sequence. Alternatively, a fragment may be an individual domain of 20-120 residues from SEQ ID No. 2. Fragments of the TADG-15 protein can be generated by methods known to those skilled in the art, e.g., by enzymatic digestion of naturally occurring or recombinant TADG-15 protein, by recombinant DNA techniques using an expression vector that encodes a defined fragment of TADG-15, or by chemical synthesis. The ability of a candidate fragment to exhibit a characteristic of TADG-15 (e.g., binding to an antibody specific for TADG-15) can be assessed by methods described herein. Purified TADG-15 or antigenic fragments of TADG-15 can be used to generate new antibodies or to test existing antibodies (e.g., as positive controls in a diagnostic assay) by employing standard protocols known to those skilled in the art. Included in this invention is polyclonal antisera generated by using TADG-15 or a fragment of TADG-15 as the immunogen in, e.g., rabbits. Standard protocols for monoclonal and polyclonal antibody production known to those skilled in this art are employed. The monoclonal antibodies generated by this procedure can be screened for the ability to identify recombinant TADG-15 cDNA clones, and to distinguish them from other cDNA clones.

Further included in this invention are TADG-15 proteins which are encoded, at least in part, by portions of SEQ ID No. 2, e.g., products of alternative mRNA splicing or alternative protein processing events, or in which a section of TADG-15 sequence has been deleted. The fragment, or the intact TADG-15 polypeptide, may be covalently linked to another polypeptide, e.g., one which acts as a label, a ligand or a means to increase antigenicity.

The invention also includes a polyclonal or monoclonal antibody which specifically binds to TADG-15. The invention encompasses not only an intact monoclonal antibody, but also an immunologically-active antibody fragment, e.g., a Fab or (Fab)$_2$ fragment; an engineered single chain Fv molecule; or a chimeric molecule, e.g., an antibody which contains the binding specificity of one antibody, e.g., of murine origin, and the remaining portions of another antibody, e.g., of human origin.

In one embodiment, the antibody, or a fragment thereof, may be linked to a toxin or to a detectable label, e.g., a radioactive label, non-radioactive isotopic label, fluorescent label, chemiluminescent label, paramagnetic label, enzyme label, or colorimetric label. Examples of suitable toxins include diphtheria toxin, *Pseudomonas* exotoxin A, ricin, and cholera toxin. Examples of suitable enzyme labels include malate hydrogenase, staphylococcal nuclease, delta-5-steroid isomerase, alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholinesterase, etc. Examples of suitable radioisotopic labels include $^3$H, $^{125}$I, $^{131}$I, $^{32}$P, $^{35}$S, $^{14}$C, etc.

Paramagnetic isotopes for purposes of in vivo diagnosis can also be used according to the methods of this invention. There are numerous examples of elements that are useful in magnetic resonance imaging. For discussions on in vivo nuclear magnetic resonance imaging, see, for example, Schaefer et al., (1989) *JACC* 14, 472-480; Shreve et al., (1986) *Magn. Reson. Med.* 3, 336-340; Wolf, G. L., (1984) *Physiol. Chem. Phys. Med. NMR* 16, 93-95; Wesbey et al., (1984) *Physiol. Chem. Phys. Med. NMR* 16, 145-155; Runge et al., (1984) *Invest. Radiol.* 19, 408-415. Examples of suitable fluorescent labels include a fluorescein label, an isothiocyalate label, a rhodamine label, a phycoerythrin label, a phycocyanin label, an allophycocyanin label, an ophthaldehyde label, a fluorescamine label, etc. Examples of chemiluminescent labels include a luminal label, an isoluminal label, an aromatic acridinium ester label, an imidazole label, an acridinium salt label, an oxalate ester label, a luciferin label, a luciferase label, an aequorin label, etc.

Those of ordinary skill in the art will know of other suitable labels which may be employed in accordance with the present invention. The binding of these labels to antibodies or fragments thereof can be accomplished using standard techniques commonly known and used by those of ordinary skill in the art. Typical techniques are described by Kennedy et al., (1976) *Clin. Chim. Acta* 70, 1-31; and Schurs et al., (1977) *Clin. Chim. Acta* 81, 1-40. Coupling techniques mentioned in the latter are the glutaraldehyde method, the periodate method, the dimaleimide method, the m-maleimidobenzyl-N-hydroxy-succinimide ester method. All of these methods are incorporated by reference herein.

Also within the invention is a method of detecting TADG-15 protein in a biological sample, which includes the steps of contacting the sample with the labeled antibody, e.g., radioactively tagged antibody specific for TADG-15, and determining whether the antibody binds to a component of the sample. Antibodies to the TADG-15 protein can be used in an immunoassay to detect increased levels of TADG-15 protein expression in tissues suspected of neoplastic transformation. These same uses can be achieved with Northern blot assays and analyses.

As described herein, the invention provides a number of diagnostic advantages and uses. For example, the TADG-15 protein is useful in diagnosing cancer in different tissues since this protein is highly overexpressed in tumor cells. Antibodies (or antigen-binding fragments thereof) which bind to an epitope specific for TADG-15, are useful in a method of detecting TADG-15 protein in a biological sample for diagnosis of cancerous or neoplastic transformation. This method includes the steps of obtaining a biological sample (e.g., cells, blood, plasma, tissue, etc.) from a patient suspected of having cancer, contacting the sample with a labeled antibody (e.g., radioactively tagged antibody) specific for TADG-15, and detecting the TADG-15 protein using standard immunoassay techniques such as an ELISA. Antibody binding to the biological sample indicates that the sample contains a component which specifically binds to an epitope within TADG-15.

Likewise, a standard Northern blot assay can be used to ascertain the relative amounts of TADG-15 mRNA in a cell or tissue obtained from a patient suspected of having cancer, in accordance with conventional Northern hybridization techniques known to those of ordinary skill in the art. This Northern assay uses a hybridization probe, e.g., radiolabelled TADG-15 cDNA, either containing the full-length, single stranded DNA having a sequence complementary to SEQ ID No. 1 (FIG. 2), or a fragment of that DNA sequence at least 20 (preferably at least 30, more preferably at least 50, and most preferably at least 100 consecutive nucleotides in length). The DNA hybridization probe can be labeled by any of the many different methods known to those skilled in this art.

The following examples are given for the purpose of illustrating various embodiments of the invention and are not meant to limit the present invention in any fashion.

EXAMPLE 1

Tissue Collection and Storage

Upon patient hysterectomy, bilateral salpingo-oophorectomy, or surgical removal of neoplastic tissue, the specimen is retrieved and placed on ice. The specimen was then taken to the resident pathologist for isolation and identification of specific tissue samples. Finally, the sample was frozen in liquid nitrogen, logged into the laboratory record and stored at −80° C.

Additional specimens were frequently obtained from the Cooperative Human Tissue Network (CHTN). These samples were prepared by the CHTN and shipped on dry ice. Upon arrival, these specimens (e.g., blood (serum), urine, saliva, tears and interstitial fluid) were logged into the laboratory record and stored at −80° C. Participation of the following divisions of the Cooperative Human Tissue Network (CHTN) in providing tumor tissues is acknowledged: Western Division, Case Western Reserve University, (Cleveland, Ohio); Midwestern Division, Ohio state University, (Columbus, Ohio); Eastern Division, NDRI, (Philadelphia, Pa.); Pediatric Division, Children's Hospital, (Columbus, Ohio); Southern Division, University of Alabama at Birmingham, (Birmingham, Ala.).

EXAMPLE 2 mRNA Isolation and cDNA Synthesis

Forty-one ovarian tumors (10 low malignant potential tumors and 31 carcinomas) and 10 normal ovaries were obtained from surgical specimens and frozen in liquid nitrogen. The human ovarian carcinoma cell lines SW626 and CAOV3, and the human breast carcinoma cell lines MDA-MB-231 and MDA-MB-435S, were purchased from the American Type Culture Collection (Rockville, Md.). Cells were cultured to sub-confluency in Dulbecco's modified Eagle's medium supplemented with 10% (v/v) fetal bovine serum and antibiotics.

Messenger RNA (mRNA) isolation was performed according to the manufacturer's instructions using the Mini RiboSep™ Ultra mRNA Isolation Kit purchased from Becton Dickinson. In this procedure, polyA$^+$ mRNA was isolated directly from the tissue lysate using the affinity chromatography media oligo(dT) cellulose. The amount of mRNA recovered was quantitated by UV spectrophotometry.

First-strand complementary DNA (cDNA) was synthesized using 5.0 µg of mRNA and either random hexamer or oligo(dT) primers according to the manufacturer's protocol utilizing a first strand synthesis kit obtained from CLONTECH (Palo Alto, Calif.). The purity of the cDNA was evaluated by PCR using primers specific for the p53 gene. These primers span an intron such that pure cDNA can be distinguished from cDNA that is contaminated with genomic DNA.

EXAMPLE 3

PCR with Redundant Primers, Cloning of TADG-15 cDNA, T-vector Ligation and Transformations and DNA Sequencing Redundant primers, forward 5'-TGGGTIGTI-ACIGCIGCICA(C/T)TG-3' (SEQ ID No. 11) and reverse 5'-A(A/G)IGGICCICCI(C/G)(T/A)(A/G)TCICC-3' (SEQ ID No. 12), corresponding to the amino acids surrounding the catalytic triad for serine proteases, were used to compare the PCR products from normal and carcinoma cDNAs.

The purified PCR products were ligated into the Promega T-vector plasmid and the ligation products used to transform JM109 competent cells according to the manufacturer's instructions (Promega). Positive colonies were cultured for amplification, the plasmid DNA isolated using the Wizard™ Minipreps DNA purification system (Promega), and the plasmids were digested with ApaI and SacI restriction enzymes to determine the size of the insert. Plasmids with inserts of the size(s) visualized by the previously described PCR product gel electrophoresis were sequenced.

Individual colonies were cultured and plasmid DNA was isolated using the Wizard Miniprep DNA purification system (Promega). Applied Biosystems Model 373A DNA sequencing system was used for direct cDNA sequence determination. Utilizing a plasmid-specific primer near the cloning site, sequencing reactions were carried out using PRISM™ Ready Reaction Dye Deoxy™ terminators (Applied Biosystems) according to the manufacturer's instructions. Residual dye terminators were removed from the completed sequencing reaction using a Centri-sep™ spin column (Princeton Separation). Based upon the determined sequence, primers that specifically amplify the gene of interest were designed and synthesized.

The original TADG-15 subclone (436 bp) was randomly labeled and used as a probe to screen an ovarian tumor cDNA library by standard hybridization techniques.[13] The library was constructed in 8ZAP using mRNA isolated from the tumor cells of a stage III/grade III ovarian adenocarcinoma patient. Three overlapping clones were obtained which spanned 3147 nucleotides.

EXAMPLE 4

Northern Blot Analysis 10 mg mRNAS were size separated by electrophoresis through a 1% formaldehyde-agarose gel in 0.02 M MOPS, 0.05 M sodium acetate (pH 7.0), and 0.001 M EDTA. The mRNAs were then blotted to Hybond-N$^+$ nylon membrane (Amersham) by capillary action in 20×SSPE. The RNAs are fixed to the membrane by baking for 2 hours at 80° C. $^{32}$P-labeled cDNA probes were made by Prime-a-Gene Labeling System (Promega). The PCR products amplified by the same primers described above were used for probes. The blots were prehybridized for 30 min and hybridized for 60 min at 68° C. with $^{32}$P-labeled cDNA probe in ExpressHyb Hybridization Solution (CLONTECH). Control hybridization to determine relative gel loading was performed with a β-tubulin probe.

Normal human tissues; spleen, thymus, prostate, testis, ovary, small intestine, colon and peripheral blood leukocyte, and normal human fetal tissues; brain, lung, liver and kidney (Human Multiple Tissue Northern Blot; CLONTECH) were also examined by the same hybridization procedure. Additional multiple tissue northern (MTN) blots from CLONTECH include the Human MTN blot, the Human MTN II blot, the Human Fetal MTN II blot, and the Human Brain MTN III blot.

EXAMPLE 5

Western Blot Analysis

Polyclonal rabbit antibody was generated by immunization with a poly-lysine linked multiple Ag peptide derived from the TADG-15 protein sequence 'LFRDWIKENTGV' (SEQ ID No. 13). Approximately 20 µg of cell lysates were separated on a 15% SDS-PAGE gel and electroblotted to PVDF at 100 V for 40 min at 4° C. The proteins were fixed to the membrane by incubation in 50% MeOH for 10 min. The membrane was blocked overnight in TBS (pH 7.8) containing 0.2% non-fat milk. Primary antibody was added to the membrane at a dilution of 1:100 in 0.2% milk/TBS and incubated for 2 h at room temperature. The blot was washed and incubated with a 1:3000 dilution of alkaline-phosphatase conjugated goat anti-rabbit IgG (BioRad) for 1 h at room temperature. The blot was washed and incubated with a chemiluminescent substrate before a 10 sec exposure to X-ray film for visualization.

EXAMPLE 6

Quantitative PCR

The mRNA overexpression of TADG-15 was determined using a quantitative PCR. Quantitative PCR was performed.[11,12] Oligonucleotide primers were used for TADG-15: forward 5'-ATGACAGAGGATTCAGGTAC-3' (SEQ ID No. 14) and reverse 5'-GAAGGTGAAGTCATTGAAGA-3' (SEQ ID No. 15); and for β-tubulin: forward 5'-CGCAT-CAACGTGTACTACAA-3' (SEQ ID No. 16) and reverse 5'-TACGAGCTGGTGGACTGAGA-3' (SEQ ID No. 17). β-tubulin was utilized as an internal control.

The PCR reaction mixture consists of cDNA derived from 50 ng of mRNA, 5 pmol of sense and antisense primers for both the TADG-15 gene and the β-tubulin gene, 200 µmol of dNTPs, 5 µCi of α-$^{32}$PdCTP and 0.25 units of Taq DNA polymerase with reaction buffer (Promega) in a final volume of 25 µl. The target sequences were amplified in parallel with the β-tubulin gene. Thirty cycles of PCR were carried out in a Thermal Cycler (Perkin Elmer Gene Amp 2400; Perkin-Elmer Cetus). Each cycle of PCR included 30 sec of denaturation at 94° C., 30 sec of annealing at 60° C. and 30 sec of extension at 72° C. The annealing temperature varies according to the primers that are used in the PCR reaction. For the reactions involving degenerate primers, an annealing temperature of 48° C. was used. The appropriate annealing temperature for the TADG-15- and b-tubulin-specific primers is 62° C.

A portion of the PCR products were separated on 2% agarose gels and the radioactivity of each PCR product was determined by using a PhosphoImager (Molecular Dynamics). In the present study, the expression ratio (TADG-15/β-tubulin) was used to evaluate gene expression and defined the value at mean±2SD of normal ovary as the cut-off value to determine overexpression. The student's t test was used for comparison of the mean values of normal ovary and tumors.

EXAMPLE 7

Immunohistochemistry

Immunohistochemical staining was performed using a Vectastain Elite ABC Kit (Vector). Formalin-fixed and paraffin-embedded specimens were routinely deparaffinized and processed using microwave heat treatment in 0.01 M sodium citrate buffer (pH 6.0). The specimens were incubated with normal goat serum in a moist chamber for 30 min. After incubation with biotinylated anti-rabbit IgG for 30 min, the sections were then incubated with ABC reagent (Vector) for 30 min. The final products were visualized using the AEC substrate system (DAKO) and sections were counterstained with hematoxylin before mounting. Negative controls were performed using normal serum instead of the primary antibody.

EXAMPLE 8

Antisense TADG-15

TADG-15 is cloned and expressed in the opposite orientation such that an antisense RNA molecule (SEQ ID No. 18) is produced. For example, the antisense RNA is used to hybridize to the complementary RNA in the cell and thereby inhibit translation of TADG-15 RNA into protein.

EXAMPLE 9

Peptide Ranking

For vaccine or immune stimulation, individual 9-mers to 11-mers were examined to rank the binding of individual peptides to the top 8 haplotypes in the general population (Parker et al., (1994)). The computer program used for this analyses can be found at <http://www-bimas.dcrt.nih.gov/molbio/hla_bind/>. Table 1 shows the peptide ranking based upon the predicted half-life of each peptide's binding to a particular HLA allele. A larger half-life indicates a stronger association with that peptide and the particular HLA molecule. The TADG-15 peptides that strongly bind to an HLA allele are putative immunogens, and are used to inoculate an individual against TADG-15.

TABLE 1

TADG-15 peptide ranking

| HLA Type & Ranking | Start | Peptide | Predicted Dissociation1/2 | SEQ ID No. |
|---|---|---|---|---|
| HLA A0201 | | | | |
| 1 | 68 | VLLGIGFLV | 2537.396 | 19 |
| 2 | 126 | LLYSGVPFL | 1470.075 | 20 |
| 3 | 644 | SLISPNWLV | 521.640 | 21 |
| 4 | 379 | KVSFKFFYL | 396.525 | 22 |
| 5 | 386 | YLLEPGVPA | 346.677 | 23 |
| 6 | 257 | SLTFRSFDL | 123.902 | 24 |
| 7 | 762 | ILQKGEIRV | 118.238 | 25 |
| 8 | 841 | RLPLFRDWI | 106.842 | 26 |
| 9 | 64 | GLLLVLLGI | 88,783 | 27 |
| 10 | 57 | VLAAVLIGL | 83.527 | 28 |
| HLA A0205 | | | | |
| 1 | 67 | LVLLGIGFL | 142.800 | 29 |
| 2 | 379 | KVSFKFFYL | 100.800 | 30 |
| 3 | 126 | LLYSGVPFL | 71.400 | 31 |
| 4 | 88 | KVFNGYMRI | 36.000 | 32 |
| 5 | 670 | TQWTAFLGL | 33.600 | 33 |
| 6 | 119 | KVKDALKLL | 25.200 | 34 |
| 7 | 60 | AVLIGLLLV | 24.000 | 35 |
| 8 | 62 | LIGLLLVLL | 23.800 | 36 |
| 9 | 57 | VLAAVLIGL | 23.800 | 37 |
| 10 | 61 | VLIGLLLVL | 23.800 | 38 |
| HLA A1 | | | | |
| 1 | 146 | FSEGSVIAY | 337.500 | 39 |
| 2 | 658 | YIDDRGFRY | 125.000 | 40 |
| 3 | 449 | SSDPCPGQF | 75.000 | 41 |
| 4 | 401 | YVEINGEKY | 45.000 | 42 |
| 5 | 387 | LLEPGVPAG | 18.000 | 43 |
| 6 | 553 | GSDEASCPK | 15.000 | 44 |
| 7 | 97 | TNENFVDAY | 11.250 | 45 |
| 8 | 110 | STEFVSLAS | 11.250 | 46 |
| 9 | 811 | SVEADGRIF | 9.000 | 47 |
| 10 | 666 | YSDPTQWTA | 7.500 | 48 |
| HLA A24 | | | | |
| 1 | 709 | DYDIALLEL | 220.000 | 49 |
| 2 | 408 | KYCGERSQF | 200.000 | 50 |
| 3 | 754 | QYGGTGALI | 50.000 | 51 |
| 4 | 153 | AYYWSEFSI | 50.000 | 52 |
| 5 | 722 | EYSSMVRPI | 50.000 | 53 |
| 6 | 326 | GFEATFFQL | 36.000 | 54 |
| 7 | 304 | TFHSSQNVL | 24.000 | 55 |
| 8 | 707 | TFDYDIALL | 20.000 | 56 |
| 9 | 21 | KYNSRHEKV | 16.500 | 57 |
| 10 | 665 | RYSDPTQWT | 14.400 | 58 |
| HLA B7 | | | | |
| 1 | 686 | APGVQERRL | 240.000 | 59 |
| 2 | 12 | GPKDFGAGL | 80.000 | 60 |
| 3 | 668 | DPTQWTAFL | 80.000 | 61 |
| 4 | 461 | TGRCIRKEL | 60.000 | 62 |
| 5 | 59 | AAVLIGLLL | 36.000 | 63 |
| 6 | 379 | KVSFKFFYL | 20.000 | 64 |
| 7 | 119 | KVKDALKLL | 20.000 | 65 |
| 8 | 780 | LPQQITPRM | 20.000 | 66 |
| 9 | 67 | LVLLGIGFL | 20.000 | 67 |
| 10 | 283 | SPMEPHALV | 18.000 | 68 |
| HLA B8 | | | | |
| 1 | 12 | GPKDFGAGL | 24.000 | 69 |
| 2 | 257 | SLTFRSFDL | 8.000 | 70 |
| 3 | 180 | MLPPRARSL | 8.000 | 71 |
| 4 | 217 | GLHARGVEL | 8.000 | 72 |
| 5 | 173 | MAEERVVML | 4.800 | 73 |
| 6 | 267 | SCDERGSDL | 4.800 | 74 |
| 7 | 567 | CTKHTYRCL | 4.000 | 75 |
| 8 | 724 | SSMVRPICL | 4.000 | 76 |
| 9 | 409 | YCGERSQFV | 3.600 | 77 |
| 10 | 495 | TCKNKFCKP | 3.200 | 78 |
| HLA B2702 | | | | |
| 1 | 427 | VRFHSDQSY | 1000.000 | 79 |
| 2 | 695 | KRIISHPFF | 600.000 | 80 |
| 3 | 664 | FRYSDPTQW | 500.000 | 81 |
| 4 | 220 | ARGVELMRF | 200.000 | 82 |
| 5 | 492 | HQFTCKNKF | 100.000 | 83 |
| 6 | 53 | GRWVVLAAV | 100.000 | 84 |
| 7 | 248 | LRGDADSVL | 60.000 | 85 |
| 8 | 572 | YRCLNGLCL | 60.000 | 86 |
| 9 | 692 | RRLKRIISH | 60.000 | 87 |
| 10 | 24 | SRHEKVNGL | 60.000 | 88 |
| HLA B4403 | | | | |
| 1 | 147 | SEGSVIAYY | 360.000 | 89 |
| 2 | 715 | LELEKPAEY | 360.000 | 90 |
| 3 | 105 | YENSNSTEF | 60.000 | 91 |
| 4 | 14 | KDFGAGLKY | 50.625 | 92 |
| 5 | 129 | SGVPFLGPY | 36.000 | 93 |

TABLE 1-continued

TADG-15 peptide ranking

| HLA Type & Ranking | Start | Peptide | Predicted Dissociation1/2 | SEQ ID No. |
|---|---|---|---|---|
| 6 | 436 | TDTGFLAEY | 33.750 | 94 |
| 7 | 766 | GEIRVINQT | 30.000 | 95 |
| 8 | 402 | VEINGEKYC | 30.000 | 96 |
| 9 | 482 | DELNCSCDA | 24.000 | 97 |
| 10 | 82 | RDVRVQKVF | 22.500 | 98 |

EXAMPLE 10

TADG-15 cDNA

A screening strategy to identify proteases which are overexpressed in human cancer has been developed in which RT-PCR products amplified specifically in tumors, as compared to normal tissue, are examined.[9] During this effort, candidate genes were identified using redundant sense primers to the conserved amino acid histidine domain at the $NH_3$ end of the catalytic domain and antisense primers to the downstream conserved amino acid serine domain. Subcloning and sequencing the appropriate 480 base pair band(s) amplified in such a PCR reaction provides the basis for identifying the gene(s) encoding proteases(s). Among these amplified catalytic domains, a new serine protease gene named TADG-15 (tumor antigen-derived gene 15) was identified. The catalytic domain of the newly identified TADG-15 protein is similar to other serine proteases and specifically contains conserved amino acids appropriate for the catalytic domain of the trypsin-like serine protease family.

A computerized search of GenEMBL databases using the FASTA program (Wisconsin Package Version 9.1, GCG, Madison, Wis.) for amino acid sequences homologous to the TADG-15 protease domain revealed that homologies with other known human proteases never exceeds 55%. FIGS. 1A-1B show the alignment of the protease domain of TADG-15 compared with other human serine proteases. Using the BESTFIT program available through GCG, the similarities between TADG-15 and trypsin, chymotrypsin, and tissue-type plasminogen activator are 51%, 46% and 52%, respectively.

From the sequence derived from the TADG-15 catalytic domain, specific primers were synthesized to amplify a TADG-15-specific probe for library screening. After screening an ovarian carcinoma library, one 1785 bp clone was obtained which included the 3' end of the TADG-15 transcript. Upon further screening using the 5' end of the newly detected clone, two additional clones were identified which provided another 1362 bp of the cDNA, including the 5' end of the TADG-15 transcript. The total length of the sequenced cDNA was approximately 3.15 kb. The total nucleotide sequence obtained includes a Kozak's consensus sequence preceding a single open reading frame encoding a predicted protein of 855 amino acids (FIG. 2).

The deduced open reading frame encoded by the TADG-15 nucleotide sequence (FIGS. 2, 3 and 4) contains several distinct domains as follows: an amino terminal cytoplasmic tail (amino acids (aa) #1-54), a potential transmembrane domain (aa #55-77), an extracellular membrane domain (aa #78-213), two complement subcomponents Clr/Cls, Uegf, and bone morphogenetic protein 1 (CUB) repeats (aa #214-447), four ligand binding repeats of the low density lipoprotein (LDL) receptor-like domain (aa #453-602) and a serine protease domain (aa #615-855). The TADG-15 protein also contains two potential N-linked glycosylation sites (aa #109 and 302) and a potential proteolytic cleavage site upstream from the protease domain (aa #614) which could release and/or activate the protease at the carboxy end of this protein. In addition, TADG-15 contains an RGD motif (aa #249-251) which is commonly found in proteins involved in cell-cell adhesion.

EXAMPLE 11

TADG-15 Expression

Figure 5:
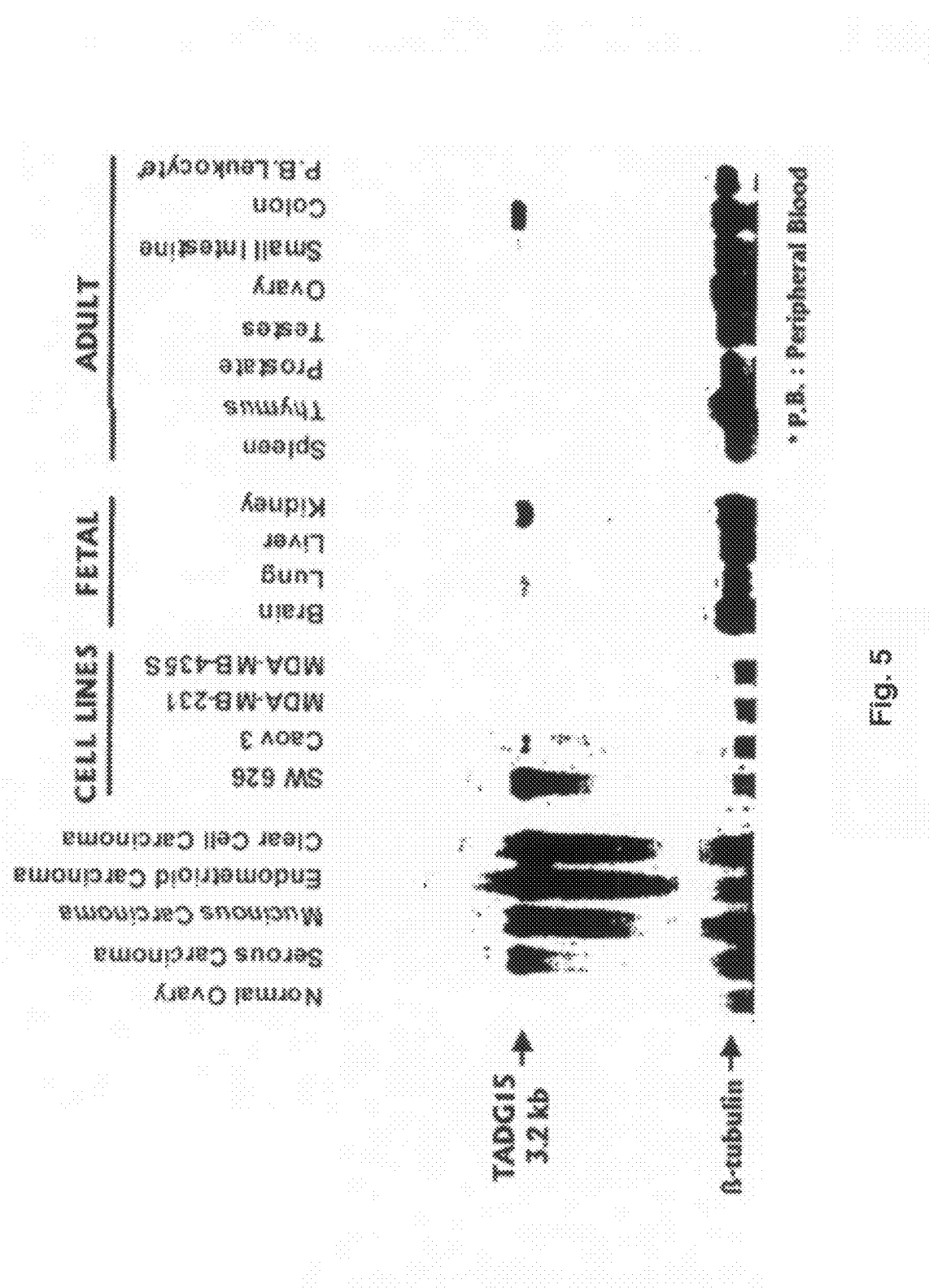
FIG. 5 shows Northern blot analysis of TADG-15 mRNA expression in normal ovary, ovarian carcinomas, carcinoma cell lines, normal fetal tissues and normal adult tissues. A single intense transcript of the TADG-15 was observed in every sub-type of carcinoma and the two ovarian carcinoma cell lines, SW626 and CAOV3, whereas no visible band was detected in normal ovary or the two breast cancer cell lines. In normal fetal tissues, fetal kidney showed increased transcript and faint expression was detected in fetal lung. In normal adult tissues, the TADG-15 was detected in colon with low expression in small intestine and prostate.

To examine the size of the transcript for TADG-15 and its pattern of expression in various tissues, Northern blot hybridization was performed for representative histological types of carcinoma and in a series of cell lines, fetal tissues and normal adult tissues (FIG. 5). The transcript size for the TADG-15 message was determined to be approximately 3.2 kb and a single intense transcript appeared to be present in all of the carcinomas examined, whereas no visible band was detected in normal ovary (FIG. 5). This transcript size is also in good agreement with the sequence data predicting a transcript size of 3.15 kb. The ovarian tumor cell lines, SW626 and CAOV3, also showed an abundance of transcript, however little or no transcript was detectable in the breast carcinoma cell lines MDA-MB-231 and MDA-MB-4355. Among normal human fetal tissues, fetal kidney showed an abundance of the TADG-15 transcript and low expression was also detected in fetal lung. In normal adult tissues, TADG-15 was detected in colon with low levels of expression in small intestine and prostate (FIG. 5).

Figure 6B:
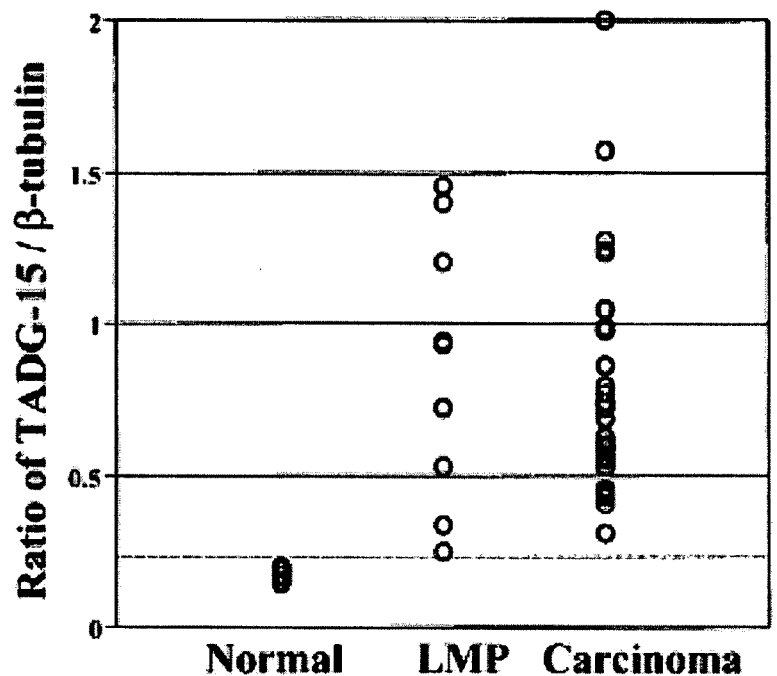
FIG. 6B shows the ratio of TADG-15 expression to expression of β-tubulin in normal ovary, LMP tumor and ovarian carcinoma. TADG-15 mRNA expression levels were significantly elevated in both LMP tumor (*; p<0.001) and carcinoma (**; p<0.0001) compared to that in normal ovary. All 10 samples of normal ovary showed a low level of TADG-15 expression.

To evaluate mRNA transcript expression of TADG-15 in ovarian tumors and normal ovary, semi-quantitative PCR (FIG. 6) was performed. In a preliminary study, the linearity of this assay[11,12] was confirmed and its efficacy correlated with both Northern blots and immunohistochemistry. The data was quantified using a phosphoimager and compared as a ratio of expression (TADG-15/β-tubulin). Results herein indicate that TADG-15 transcript expression is elevated above the cut-off value (mean for normal ovary±2 SD) in all of the tumor cases examined and is either not detected or detected at extremely low levels in normal ovaries (FIGS. 6A and B). Analysis of ovarian carcinoma subtypes, including early stage and late stage disease, confirms overexpression of TADG-15 in all carcinomas examined (Table 2). All of the carcinomas studied, which included 5 stage I and 3 stage II carcinomas, showed overexpression of the TADG-15 gene.

These data can also be examined with regard to tumor stage and histological sub-type, and results indicated that every carcinoma of every stage and histological sub-type overexpressed the TADG-15 gene. The expression ratio (mean value±SD) for normal ovary group was determined as 0.182±0.024, for LMP tumor group as 0.847±0.419 and for carcinoma group as 0.771±0.380 (Table 2). A comparison between the normal ovary group and tumor groups showed that overexpression of the TADG-15 gene is statistically significant in both the LMP tumor group and the carcinoma group (LMP tumor: $p<0.001$, carcinoma: $p<0.0001$).

Figure 7:
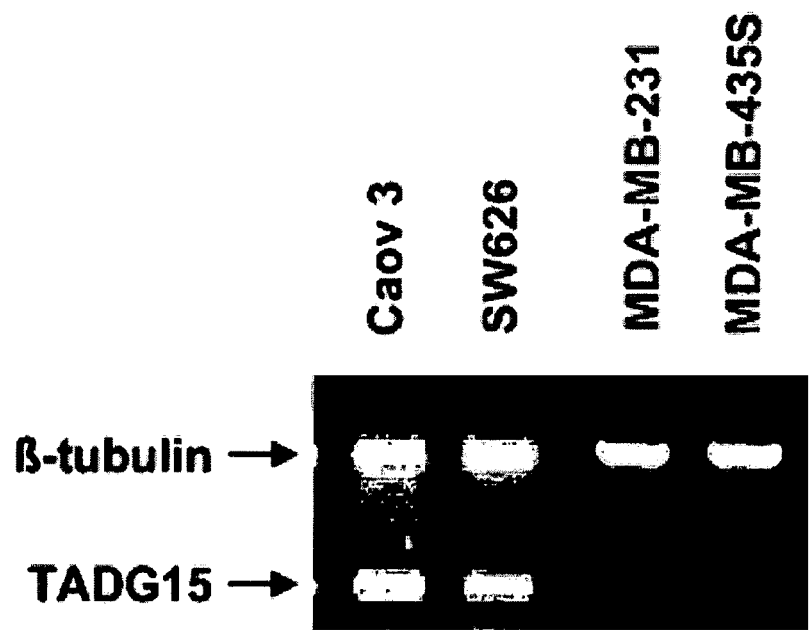
FIG. 7 shows the TADG-15 expression in tumor cell lines derived from both ovarian and breast carcinoma tissues.
Figure 8:
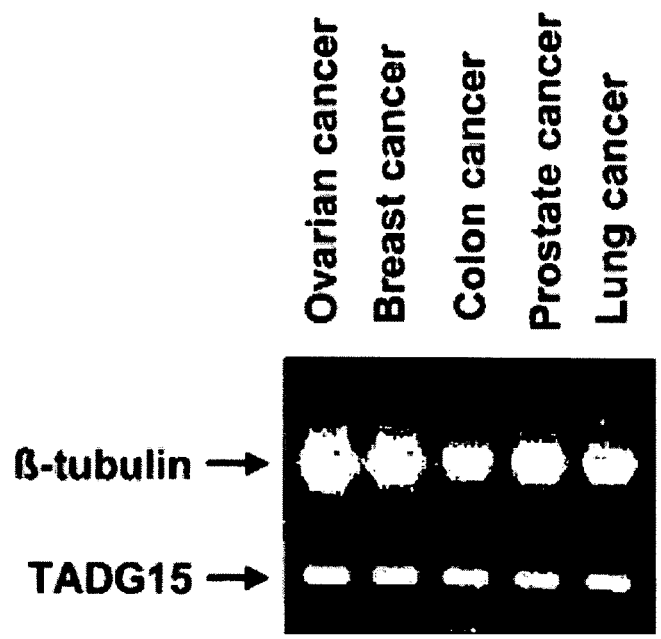
FIG. 8 shows the overexpression of TADG-15 in other tumor tissues.

As shown in FIG. 6, TADG-15 transcripts were noted in all ovarian carcinomas, but were not present at detectable levels in any of the following tissues: a) normal ovary, b) fetal liver and brain, c) adult spleen, thymus, testes, ovary and peripheral blood lymphocytes, d) skeletal muscle, liver, brain or heart. This evaluation was extended to a standard panel of about 40 tumors. Using TADG-15-specific primers, the expression was also examined in tumor cell lines derived from both ovarian and breast carcinoma tissues as shown in FIG. 7 and in other tumor tissues as shown in FIG. 8. Expression of TADG-15 was also observed in carcinomas of the breast, colon, prostate and lung.

Figure 9:
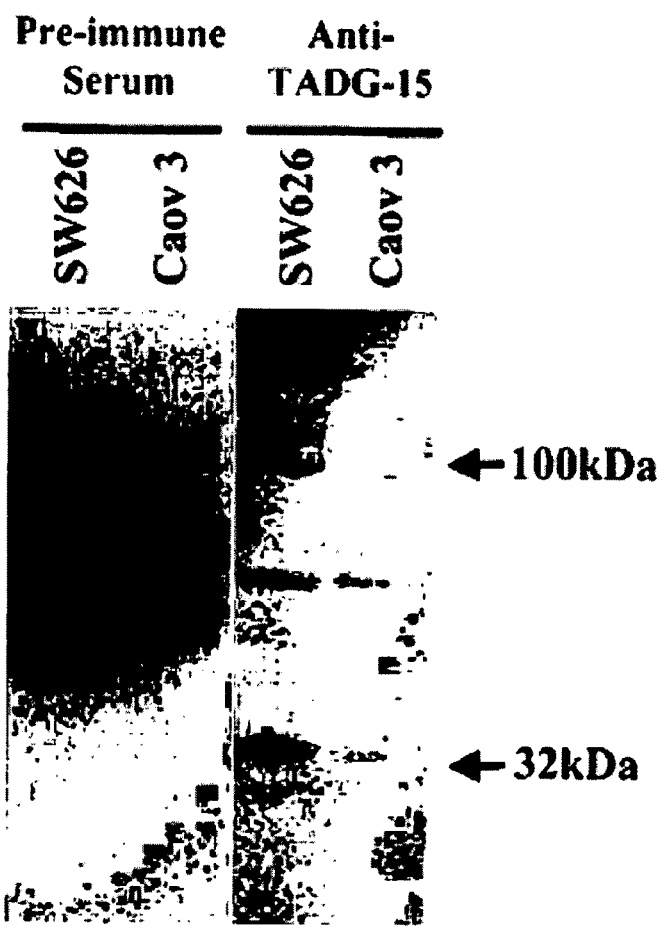
FIG. 9 shows SW626 and CAOV3 cell lysates that were separated by SDS-PAGE and immunoblotted. Lanes 1 and 2 were probed with rabbit pre-immune serum as a negative control. Lanes 3 and 4 were probed with polyclonal rabbit antibody generated to a carboxy terminal peptide from TADG-15 protein sequence.

Polyclonal antibodies developed to a synthetic peptide (a 12-mer) at the carboxy terminus of the protease domain were used to examine TADG-15 expression in cell lines by Western blot and by immunolocalization in normal ovary and ovarian tumors. Western blots of cell extracts from SW626 and CAOV3 cells were probed with both antibody and preimmune sera (FIG. 9). Several bands were detected with the antibody, including bands of approximately 100,000 daltons, approximately 60,000 daltons and 32,000 daltons. The anticipated molecular size of the complete TADG-15 molecule is estimated to be approximately 100,000 daltons, and the protease domain which may be released by proteolytic cleavage at aa #614 is estimated to be approximately 32,000 daltons. Some intermediate proteolytic product may be represented by the 60,000 dalton band.

Antibody staining of tumor cells confirms the presence of the TADG-15 protease in the cytoplasm of a serous LMP tumor, mucinous LMP tumor and serous carcinoma (FIGS. 10B, C & D, respectively). This diffuse staining pattern may be due to detection of TADG15 within the cell as it is being packaged and transported to the cell surface. In endometrioid carcinoma, the antigen is clearly detectable on the surface of tumor cells (FIG. 10E). No staining was detected in normal ovarian epithelium or stromal cells (FIG. 10A). Immunohistochemical staining of a series of 27 tumors indicates the presence of the TADG-15 protein in all the carcinoma subtypes examined, including the low malignant potential group. Strong staining was noted in 7 of 9 low malignant potential tumors and 13 of 18 carcinomas (Table 3).

TABLE 2

Number of cases with overexpression of TADG-15 in normal ovaries and ovarian tumors

|  | N | overexpression of TADG-15 |  | expression ratio$^a$ |
| --- | --- | --- | --- | --- |
| Normal | 10 | 0 | (0%) | 0.182 ± 0.024 |
| LMP | 10 | 10 | (100%) | 0.847 ± 0.419 |
| serous | 6 | 6 | (100%) | 0.862 ± 0.419 |
| mucinous | 4 | 4 | (100%) | 0.825 ± 0.483 |
| Carcinoma | 31 | 31 | (100%) | 0.771 ± 0.380 |
| serous | 18 | 18 | (100%) | 0.779 ± 0.332 |
| mucinous | 7 | 7 | (100%) | 0.907 ± 0.584 |
| endometrioid | 3 | 3 | (100%) | 0.502 ± 0.083 |
| clear cell | 3 | 3 | (100%) | 0.672 ± 0.077 |

$^a$The ratio of expression level of TADG-15 to β-tubulin (mean ± SD)

TABLE 3

Immunohistochemical staining using TADG-15

| Lab No. | Histology | TADG-15 |
| --- | --- | --- |
|  | Surface epithelium of the ovary | − |
| H-3194 | serous (LMP) | ++ |
| H-162 | serous (LMP) | ++ |
| H-1182 | serous (LMP) | ++ |
| H-4818 | serous (LMP) | ++ |
| H-4881 | serous (LMP) | ++ |
| H-675 | mucinous (LMP) | + |
| H-2446 | mucinous (LMP) | + |
| H-0707 | mucinous (LMP) | ++ |
| H-2042 | mucinous (LMP) | ++ |
| H-2555 | serous carcinoma | ++ |
| H-1858 | serous carcinoma | ++ |
| H-5266 | serous carcinoma | ++ |
| H-5316 | serous carcinoma | + |
| H-2597 | serous carcinoma | + |

TABLE 3-continued

Immunohistochemical staining using TADG-15

| Lab No. | Histology | TADG-15 |
| --- | --- | --- |
| H-4931 | mucinous carcinoma | ++ |
| H-1867 | mucinous carcinoma | ++ |
| H-5998 | mucinous carcinoma | ++ |
| H-2679 | endometrioid adenocarcinoma | + |
| H-5718 | endometrioid adenocarcinoma | ++ |
| H-3993 | endometrioid adenocarcinoma | + |
| H-2991 | endometrioid adenocarcinoma | ++ |
| H-2489 | endometrioid adenocarcinoma | ++ |
| H-5994 | clear cell carcinoma | ++ |
| H-6718 | clear cell carcinoma | ++ |
| H-1661 | clear cell carcinoma | ++ |
| H-6201 | clear cell carcinoma | ++ |
| H-5640 | clear cell carcinoma | + |

− Negative; + Weak Positive; ++ Strong Positive (more than 50% of cell staining)

EXAMPLE 12

TADG-15 Homology

Recently, a mouse protein named epithin (GenBank Accession No. AF042822) has been described.[14] Epithin is a 902 amino acid protein which contains a similar structure to TADG-15 in that it has a cytoplasmic domain, transmembrane domain, two CUB domains, four LDLR-like domains and a carboxy terminal serine protease domain. TADG-15 and epithin are 84% similar over 843 amino acids, suggesting that the proteins may be orthologous (FIGS. 11A-11B). The precise role of epithin remains to be elucidated.

A search of GeneBank for similar previously identified sequences yielded one such sequence with relatively high homology to a portion of the TADG-15 gene. The similarity between the portion of TADG-15 from nucleotide #182 to 3139 and SNC-19 GeneBank Accession No. #U20428) is approximately 97% (FIGS. 12A-12E). There are however significant differences between SNC-19 and TADG-15. For example, TADG-15 has an open reading frame of 855 amino acids whereas the longest open reading frame of SNC-19 is 173 amino acids. Additionally, SNC-19 does not include a proper start site for the initiation of translation, nor does it include the amino terminal portion of the protein encoded by TADG-15. Moreover, SNC-19 does not include an open reading frame for a functional serine protease because the His, Asp and Ser residues of the catalytic triad that are necessary for function are encoded in different reading frames.
Implications The overall structure of the TADG-15 protein is relatively similar to the members of the tolloid/BMP-1 family and the complement subcomponents, Clr/Cls. These proteins contain both CUB and protease domains, and complex formation through the ligand binding domain is essential for their function. Activation of the serine protease domains of Clr and Cls requires proteolytic cleavage of Arg-Gly and Arg-Ile bonds, respectively.[15] Similarly, it might be expected that the TADG-15 protein is synthesized as a zymogen, which is activated by cleavage between $Arg^{614}$ and $Val^{615}$ and analogous to the activation mechanism of other serine protease zymogens. Western blot analysis of cultured cell lysates confirmed both a 100 kDa and 32 kDa peptide, which correspond to the putative zymogen (whole molecule) and a cleaved protease product of TADG-15 (FIG. 9). These data support a model for proteolytic release and/or activation of TADG-15 as occurs for similar type II serine proteases.

CUB domains were first found in complement subcomponents Clr/Cls[16-18] and are known to be a widespread module in developmentally regulated proteins, such as the bone morphogenetic protein-1 (BMP-1) and the tolloid gene product.[18-20] The role of these repeats remains largely unknown. However, some models suggest that the CUB domain may be involved in protein-protein interactions. The CUB domain of C1r and C1s participates in the assembly of the C1s-C1r-C1r-C1s tetrameric complex in the activation of the classical pathway of complement by providing protein-protein interaction domains.[15] The *Drosophila* decapentaplegic (DPP) protein is essential for dorsal-ventral specification of the embryo, and the *Drosophila* tolloid (TLD) forms a complex with DPP to regulate its activity.[19,20] Missense mutations in the CUB domain of the tolloid protein results in a phenotype that does not allow a protein interaction with the DPP complex.[19]

The TADG-15 protein contains two tandem repeats of CUB-like domains between amino acid residues 214 and 447. Each of these is approximately 110 amino acids long and each has four conserved cysteine residues characteristic of other CUBs (amino acids 214, 244, 268, 294, 340, 366, 397, 410). By analogy, the CUB repeats of the TADG-15 protein may form an interactive domain capable of promoting multimeric complex formation and regulating the activity of the target protein or TADG-15 itself.

The TADG-15 protein also contains the LDL receptor ligand binding repeat (class A motif)-like domain, which consists of four contiguous cysteine-rich repeats (amino acid residues 453 to 602). Each cysteine-rich repeat is approximately 40 amino acids long and contains a conserved, negatively-charged sequence (Ser-Asp-Glu) with six cysteine residues. In the LDL receptor protein, this repeat is thought to function as a protein-binding domain which interacts with the lysine and arginine residues present in lipoproteins.[21,22] In addition, the first repeat of the LDL receptor appears to bind $Ca^{2+}$ and not the lipoproteins.[23] By analogy, it is possible that the LDL receptor-like repeat in TADG-15 may act in a similar fashion, interacting with positively charged regions of other proteins and/or as a $Ca^{2+}$ binding site. As a result of ligand binding and the formation of receptor-ligand complex, LDL receptor is internalized via clathrin-coated pits.[24] These types of plasma membrane receptors contain a characteristic amino acid sequence in their cytoplasmic domain for binding to clathrin-coated pits.[24] TADG-15 does not contain this motif in its cytosolic region, and furthermore, no similarities with other known protein sequences were found in the cytoplasmic domain of the TADG-15. This finding suggests that TADG-15 functions in a different manner from the endocytic receptors (such as the LDL receptor), although TADG-15 possesses similar ligand-binding repeats in the extracellular matrix.

Although the precise role of TADG-15 is unknown, this gene is clearly overexpressed in ovarian tumors. A variety of proteases, such as type IV collagenase and plasminogen activator, appear to be involved in the process of tumor invasion and are constituents of a protease cascade in malignant progression. TADG-15 may constitute such an activity and directly digest extracellular matrix components surrounding a tumor, or activate other proteases by cleavage of inactive precursors, indirectly enhancing tumor growth and invasion. It is also possible that TADG-15 may function like a member of the tolloid/BMP-1 family by forming complexes with other growth factors or signal transduction proteins to modulate their activities.

These data raise the possibility that the TADG-15 gene and its translated protein will be a useful marker for the early detection of ovarian carcinoma through release of the protease domain into the extracellular matrix and ultimately the circulation. These data also suggest the possibility of using TADG-15 as a target for therapeutic intervention through delivery systems directed at the CUB/LDLR ligand binding domains.

The following references were cited herein:

1. Liotta, L. A., et al. Cell, 64: 327-336, 1991.
2. Duffy, M. J. Clin. Exp. Metastasis, 10: 145-155, 1992.
3. Tryggvason, K., et al. Biochem. Biophys. Acta., 907: 191-217, 1987.
4. Levy, A. T., et al. Cancer Res., 51: 439-444, 1991.
5. Monsky, W. L. et al. Cancer Res., 53: 3159-3164, 1993.
6. Duffy, M. J. et al. Cancer, 62: 531-533, 1988.
7. Häckel, C., et al. Cancer, 79: 53-58, 1997.
8. Watt, K, et al. Proc. Natl. Acad. Sci. U.S.A., 83: 3166-3170, 1986.
9. Tanimoto, H. et al. Cancer Res., 57: 2884-2887, 1997.
11. Shigemasa, K. et al. J. Soc. Gynecol. Invest., 4: 95-102, 1997.
12. Tanimoto, H. et al. Gynecol. Oncol., 66: 308-312, 1997.
13. Maniatis, T., Fritsch, E. F. & Sambrook, J. Molecular Cloning, p. 309-361 Cold Spring Harbor Laboratory, New York, 1982.
14. Kim, M. G., et al. Immunogenetics, 49(5):420-428, 1999.
15. Arlaud et al. Method in Enzymology, 223: 61-82, 1993.
16. Journet, A. & Tosi, M. Biochem. J., 240: 783-787, 1986.
17. Mackinnon, C. M., et al. Eur. J. Biochem., 169: 547-553, 1987.
18. Bork, P. & Beckmann, G. J. Mol. Biol., 231: 539-545, 1993.
19. Childs, S. R. & O'Connor, M. B. Dev. Biol., 162: 209-220, 1994.
20. Blader, P L, et al. Science, 278: 1937-1940, 1997.
21. Yamamoto, T. et al. Cell, 39: 27-38, 1984.
22. Daly, N. L., et al. Proc. Natl. Acad. Sci., 92: 6334-6338, 1995.
23. van Driel, I. R., et al. J. Biol. Chem., 262: 17443-17449, 1987.
24. Lodish, H. et al. Sorting of membrane proteins internalized from the cell surface. In: Molecular Cell Biology, 3rd ed., p. 722-733 Scientific American Books, Inc., New York, 1995.
25. Parker, K C et al. J. Immunol. 152:163, 1994.

Any patents or publications mentioned in this specification are indicative of the levels of those skilled in the art to which the invention pertains. These patents and publications are herein incorporated by reference to the same extent as if each individual publication was specifically and individually indicated to be incorporated by reference. One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of producing immune-activated cells directed toward TADG-15, comprising the steps of:

exposing dendritic cells to the TADG-15 protein having the amino acid sequence shown in SEQ ID No. 2 or immunogenic fragment thereof, wherein the TADG-15 protein or immunogenic fragment thereof lacks TADG-15 protease activity, wherein the exposure to the TADG-15 protein or immunogenic fragment thereof activates the dendritic cells, thereby producing immune-activated cells directed toward TADG-15.

2. The method of claim 1, wherein the immune-activated cells are B-cells, T-cells or dendrites.

* * * * *